United States Patent
Palli et al.

(10) Patent No.: US 11,793,829 B2
(45) Date of Patent: Oct. 24, 2023

(54) DEVELOPMENT OF POLYLYSINE:EPIGALLOCATECHIN-3-O-GALLATE AND DSRNA POLYPLEXES FOR CONTROL OF MOSQUITOES

(71) Applicant: University of Kentucky Research Foundation, Lexington, KY (US)

(72) Inventors: Subba Reddy Palli, Lexington, KY (US); Ramesh Dhandapani, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 411 days.

(21) Appl. No.: 17/006,588

(22) Filed: Aug. 28, 2020

(65) Prior Publication Data

US 2021/0060053 A1 Mar. 4, 2021

Related U.S. Application Data

(60) Provisional application No. 62/893,012, filed on Aug. 28, 2019.

(51) Int. Cl.
| | |
|---|---|
| *A61K 31/713* | (2006.01) |
| *C12N 15/113* | (2010.01) |
| *A61K 47/69* | (2017.01) |
| *C12N 15/86* | (2006.01) |
| *A61K 47/32* | (2006.01) |
| *A61K 9/00* | (2006.01) |
| *A61K 9/08* | (2006.01) |

(52) U.S. Cl.
CPC ............ *A61K 31/713* (2013.01); *A61K 47/32* (2013.01); *A61K 47/6937* (2017.08); *C12N 15/113* (2013.01); *C12N 15/86* (2013.01); *A61K 9/0053* (2013.01); *A61K 9/08* (2013.01); *C12N 2310/14* (2013.01)

(58) Field of Classification Search
CPC .. C12N 15/113; C12N 15/86; C12N 2310/14; C12N 2310/3515; C12N 15/111; A61K 31/713; A61K 47/6937; A61K 9/0053; A61K 47/6455; A61K 47/6927
USPC ...... 424/9.1; 435/6.1, 91.1, 91.31, 455, 458; 514/44 A, 44 R; 536/23.1, 24.5
See application file for complete search history.

(56) References Cited

PUBLICATIONS

Zhu et al (Annu. Rev. Entomol., vol. 65, pp. 293-311 (2020)) (Year: 2020).*
Zhang et al (Insect Molec. Biol., vol. 19, No. 5, pp. 683-693 (2010)) (Year: 2010).*
Das et al (ACS Applied Materials and Interfaces, vol. 7, pp. 19530-19535 (2015)).*
Shen et al (ACS Cent. Sci., vol. 4, pp. 1326-1333 (2018)) (Year: 2018).*
Walker et al (Entomolgia Experimentalis et Applicata, vol. 138, pp. 83-92 (2011)) (Year: 2011).*
Kumar et al (Int'l J. Biol. Macromolecules, vol. 86, pp. 89-95 (2016)) (Year: 2016).*
Wang et al (Apoptosis, vol. 16, No. 3, pp. 235-248 (2011)) (Year: 2011).*
Dhandapani et al (Scientific Reports, vol. 9, p. 8775 (2019)) (Year: 2019).*
Das, S., et al., Chitosan, Carbon Quantum Dot, and Silica Nanoparticle Mediated dsRNA Delivery for Gene Silencing in Aedes aegypti: A Comparative Analysis. ACS Appl Mater Interfaces, 2015. 7(35): p. 19530-5.
Dhandapani, R.K., et al., Development of CS-TPP-dsRNA nanoparticles to enhance RNAi efficiency in the yellow fever mosquito, Aedes aegypti. Sci Rep, 2019. 9(1): p. 8775.
Kumar, D.R., Kumar, P.S., Gandhi, M.R., Al-Dhabi, N.A., Paulraj, M.G. & Ignacimuthu, S., 2016. Delivery of chitosan/dsRNA nanoparticles for silencing of wing development vestigial (vg) gene in Aedes aegypti mosquitoes. Int J Biol Macromol. 86, 89-95. doi: 10.1016/j.ijbiomac.2016.01.030 (2016).
Mysore, K., Flannery, E.M., Tomchaney, M., Severson, D.W. & Duman-Scheel, M. Disruption of Aedes aegypti olfactory system development through chitosan/siRNA nanoparticle targeting of semaphorin-1a. PLoS Negl Trop Dis. 7(5), 2215. doi: 10.1371/journal.pntd.0002215 (2013).
Palli, S.R. RNA interference in Colorado potato beetle: steps toward development of dsRNA as a commercial insecticide. Curr Opin Insect Sci. 6, 1-8. doi: 10.1016/j.cois.2014.09.011 (2014).
Zhang, X., J. Zhang, and K.Y. Zhu, Chitosan/double-stranded RNA nanoparticle-mediated RNA interference to silence chitin synthase genes through larval feeding in the African malaria mosquito (Anopheles gambiae). Insect Mol Biol, 2010. 19(5): p. 683-93.
Zhu, F., Xu, J., Palli, R., Ferguson, J. & Palli, S.R. Ingested RNA interference for managing the populations of the Colorado potato beetle, Leptinotarsa decemlineata. Pest Manag Sci. 67(2), 175-182. doi: 10.1002/ps.2048 (2011).
Zhu, K.Y. and S.R. Palli, Mechanisms, Applications, and Challenges of Insect RNA Interference. Annu Rev Entomol, 2020. 65: p. 293-311.

* cited by examiner

*Primary Examiner* — Jane J Zara
(74) *Attorney, Agent, or Firm* — Stites & Harbison PLLC; Mandy Wilson Decker

(57) ABSTRACT

The present invention relates to a polyplex composition for modulating expression of a gene-of-interest in an insect comprising: a crosslinker, a cation, and a molecule for initiating RNA interference (RNAi). The present invention further relates to polyplex compositions for modulating genes of interest in *Aedes aegypti*. The present invention further relates to methods of modulating a gene-of-interest in an insect, comprising: administering to an insect a polyplex composition for modulating expression of a gene-of-interest in an insect comprising: a crosslinker, a cation, and a molecule for initiating RNA interference (RNAi).

12 Claims, 52 Drawing Sheets

Specification includes a Sequence Listing.

FIG. 14A
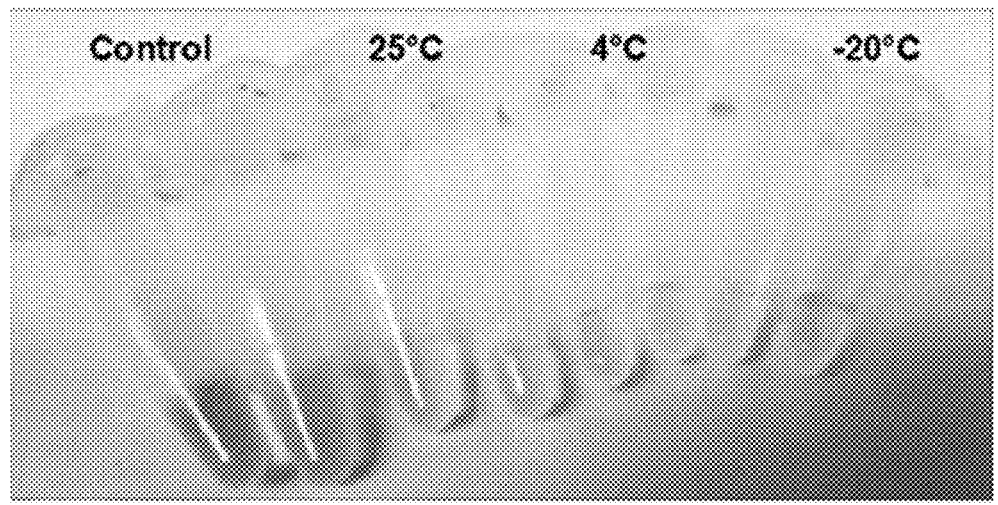
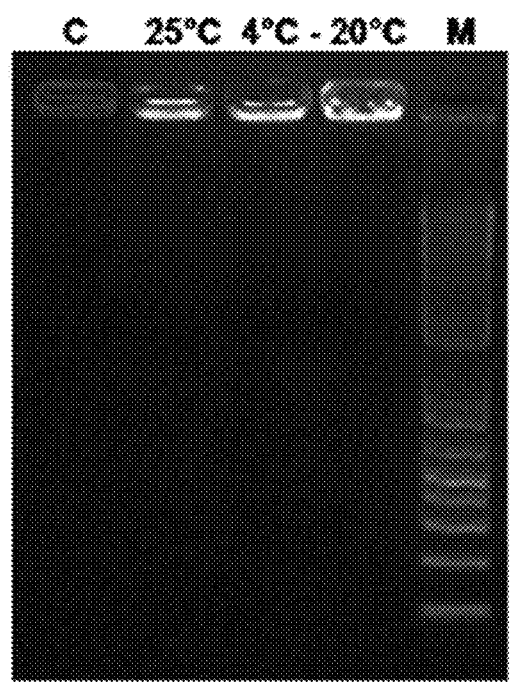
FIG. 14B

| S.No | Samples | Z size | Charge | PDI |
|---|---|---|---|---|
| 1 | PS:Cf:dsRNA | 174 | +30.8 | 0.28 |
| 2 | PLL:EGCG:dsRNA | 165 | +31.5 | 0.375 |
| 3 | PEI:dsRNA:PLGA | 136 | +33.4 | 0.187 |

DEVELOPMENT OF POLYLYSINE:EPIGALLOCATECHIN-3-O-GALLATE AND DSRNA POLYPLEXES FOR CONTROL OF MOSQUITOES

RELATED APPLICATIONS

This application claims priority from U.S. Provisional Patent Application No. 62/893,012 filed on Aug. 28, 2019 the entire disclosure of which is incorporated herein by this reference.

GOVERNMENT INTEREST

This invention was made with government support under grant numbers 3200001140, awarded by the National Institutes of Health and 3200000682, awarded by the United States Department of Agriculture. The government has certain rights in the invention.

SEQUENCE LISTING

This application contains a sequence listing submitted in accordance with 37 C.F.R. 1.821, named 13177N 2379US PALLI sequence listing.txt, created on Aug. 27, 2020, having a size of 2,255 bytes, which is incorporated herein by this reference.

TECHNICAL FIELD

The present invention relates to a polyplex composition for modulating expression of a gene-of-interest in an insect comprising: a cation, a crosslinker, and a molecule for initiating RNA interference (RNAi).

BACKGROUND

Mosquito-borne diseases remain a major threat to human health and continue to impede socioeconomic development. Increasing resistance of mosquitoes to chemical insecticides is a great public health concern. Therefore, new strategies are necessary to develop the next generation of vector control methods. Because of the target specificity of double-stranded RNA, the RNAi-based control measures are an attractive alternative to current insecticides used to control disease vectors. In the instant invention, polyplexes comprising a cation, a crosslinker, and a molecule for initiating RNAi; wherein the cation:crosslinker ratio is from about 1:0.1 to about 1:100.

In this invention polyplexes are designed for mosquito control by self-assembly of (−) epigallocatechin-3-o-gallate (EGCG) and dsRNA by employing poly-l-lysine (PLK) as a biodegradable polymer. The dsRNA polyplexes were prepared by entropy-driven complexation of dsRNA with catechin to yield a negatively charged core, followed by coating the core with PLK polymer. The polymer condensed dsRNA into uniform size, positively charged and spherical polyplexes. The PLK:EGCG:dsRNA polyplexes with entrapped dsRNA performed well as dsRNA delivery vehicles, possibly due to their high binding capacity and loading efficiency. The PLK:EGCG:dsRNA polyplexes showed the controlled release of dsRNA in neutral or alkaline pH. The PLK:EGCG:DNA polyplexes supported transfection of DNA into *Aedes aegypt*, Aag-2 cells. The PLK:EGCG:dsIAP (dsRNA targeting inhibitor of apoptosis) polyplexes knocked down target genes in cell lines as well as in *Ae. aegypti* larvae and induced mortality of larvae. These results showed that PLK:EGCG:dsRNA polyplexes could serve as safe and effective vehicles for delivery for dsRNA to control disease vectors such as the mosquito, *Aedes aegypt*, the fall army worm, and the Asian longhorned beetle.

In the instant invention polyplexes are designed for mosquito control by self-assembly of celfectin (Cf) and dsRNA by employing protamine sulfate (PS) as a biodegradable polymer. The dsRNA polyplexes were prepared by entropy-driven complexation of dsRNA with catechin to yield a negatively charged core, followed by coating the core with PS polymer. The polymer condensed dsRNA into uniform size, positively charged and spherical polyplexes. The PS:CF:dsRNA polyplexes with entrapped dsRNA performed well as dsRNA delivery vehicles, possibly due to their high binding capacity and loading efficiency. The PS:CF:dsRNA polyplexes showed the controlled release of dsRNA in neutral or alkaline pH. The PS:CF:dsRNA polyplexes supported transfection of DNA into *Aedes aegypt*, Aag-2 cells. The PS:CF:dsIAP (dsRNA targeting inhibitor of apoptosis) polyplexes knocked down target genes in cell lines as well as in *Ae. aegypti* larvae and induced mortality of larvae. These results showed that PS:CF:dsRNA polyplexes could serve as safe and effective vehicles for delivery for dsRNA to control disease vectors such as the mosquito, *Aedes aegypt*, the fall army worm, and the Asian longhorned beetle.

In this invention polyplexes are designed for mosquito control by self-assembly of PLGA and dsRNA by employing PEI as a biodegradable polymer. The dsRNA polyplexes were prepared by entropy-driven complexation of dsRNA with catechin to yield a negatively charged core, followed by coating the core with PEI polymer. The polymer condensed dsRNA into uniform size, positively charged and spherical polyplexes. The PEI:PLGA:dsRNA polyplexes with entrapped dsRNA performed well as dsRNA delivery vehicles, possibly due to their high binding capacity and loading efficiency. The PEI:PLGA:dsRNA polyplexes showed the controlled release of dsRNA in neutral or alkaline pH. The PEI:PLGA:dsRNA polyplexes supported transfection of DNA into *Aedes aegypt*, Aag-2 cells. The PEI:PLGA:dsIAP (dsRNA targeting inhibitor of apoptosis) polyplexes knocked down target genes in cell lines as well as in *Ae. aegypti* larvae and induced mortality of larvae. These results showed that PEI:PLGA:dsRNA polyplexes could serve as safe and effective vehicles for delivery for dsRNA to control disease vectors such as the mosquito, *Aedes aegypt*, the fall army worm, and the Asian longhorned beetle.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIG. 14A shows polyplexes stability assay. PLK-EGCG-dsRNA polyplexes stability was checked the different temperature (25° C., 4° C. and −20° C.).

FIG. 14B shows polyplexes stability assay. After 25 days polyplexes were checked 1% agarose gel electrophoresis. The polyplexes were more stable in −20° C. up to 25 days.

Figure 1A:
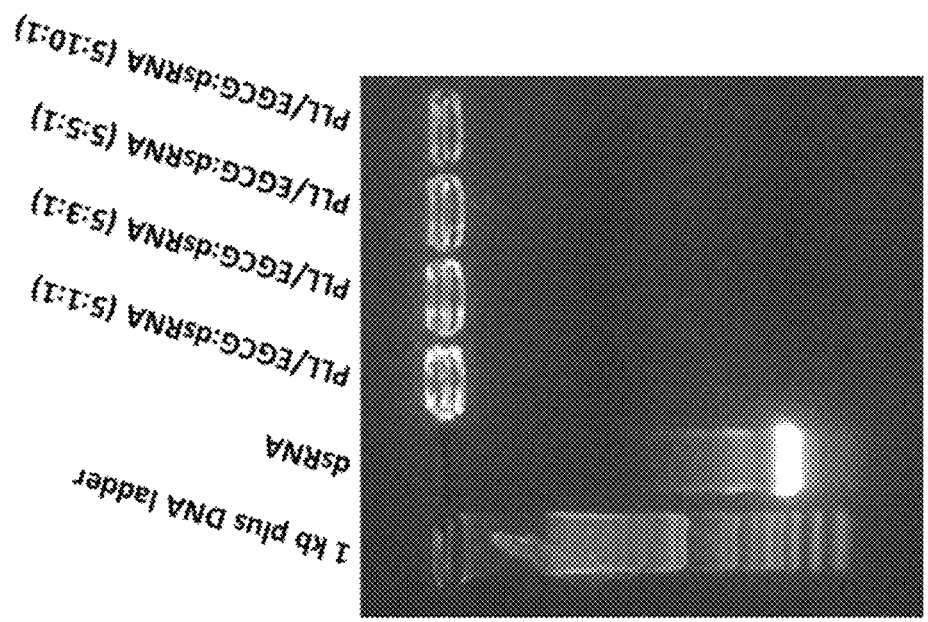
FIG. 1A shows synthesis and characterization of PLK:dsRNA polyplexes. Polyplexes prepared using 1 μg dsRNA and 1-10 μg PLK were evaluated by 1% agarose gel electrophoresis. The gel retardation assay of PLL:dsRNA and PLL:EGCG:dsRNA nanoparticles by agarose gel electrophoresis. Naked dsRNA, 1 kb plus DNA ladder, PLL:dsRNA and PLL:EGCG:dsRNA were resolved on 1% (W/V) agarose gel, stained with GelRed® and gel images were captured using Alpha Imager™ Gel Imagine System under a UV light.
Figure 1A:
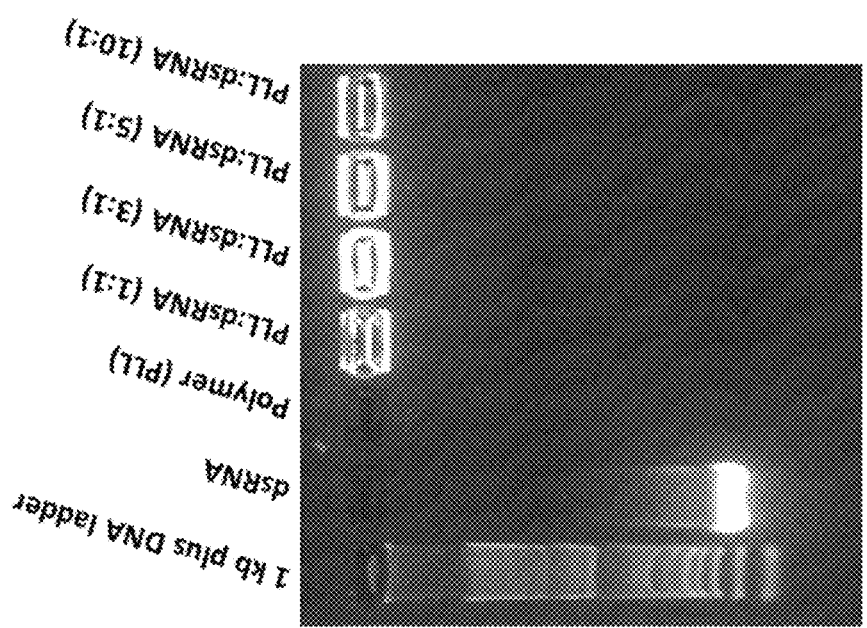

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

SUMMARY

In accordance with the purpose(s) of the invention, as embodied and broadly described herein, the invention, in one aspect, relates to methods

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

Definitions

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein.

As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "essential insect genes" refers to genes identified in the publication Christiaens, Olivier, et al. *Literature review of baseline information on RNAi to support the environmental risk assessment of RNAi-based GM plants*. EFSA Supporting Publications. 2018; 15(5):EN-1424, 173 pp. https://doi.org/10.2903/sp.efsa.2018.EN-1424. This publication is herein incorporated by reference in its entirety. Essential insect genes include but are not limited to: cactus, asnap, sinra, hsp, gw, srp, rop, pp1a, rpn7, rpt3, Mesh, HEL25E, Sec23, SAR1, SSK, Sam-S, VhaSFD, Sec61α, Nito, snRNP, Rpn11, Rpn12, Ebony, Surf4, Prosα1, Prosα6, Uba1, Chc, Shi, ATPsyn-β, Cas, Prosβ35, RpL6, Mam, unc-104, DSP1, Fkh1, He125E, Gcm, spt16, NCM, ROP, RPB7, DRE4, RP11140, snf7, Sac1, actin, IAP, SRC, Met, JHAMT and EcR.

As used herein, the term "subject" refers to a target of administration. The subject of the herein disclosed methods can be an insect. Thus, the subject of the herein disclosed methods can include an insect of the order Diptera and the genus *Aedes*. The term does not denote a particular age or sex.

As used herein, the terms "administering" and "administration" refer to any method of providing a pharmaceutical preparation to a subject. Such methods are well known to those skilled in the art and include, but are not limited to, oral administration, dermal administration via the cuticle, ophthalmic administration, intracerebral administration, and respiratory administration, and injectable administration. Administration can be continuous or intermittent.

As used herein, the term "effective amount" refers to an amount that is sufficient to achieve the desired result or to have an effect on an undesired condition. For example, a "effective amount" may refer to an amount that is sufficient to achieve the desired therapeutic result or to have an effect on undesired outcomes, but is generally insufficient to cause adverse side effects. In the instant invention a desired outcome is the inhibition of particular polypeptides in an insect following the administration of an effective amount of a composition described herein. In some aspects of the present invention, administration of 40 µg of RNA in a polyplex is an effective amount. In some aspects of the present invention, administration of 25 ng of nanoparticle is an effective amount, while in some aspects. 10 µg or 25 µg is an effective amount.

As used herein, the term "polyplex(es)" is used interchangeably with and carries the same meaning as understood by one of ordinary skill in the art as the term "nanoparticle(s)."

As used herein, the term "crosslinker" refers to molecules that are capable of bonding one molecule (molecule A) to another (molecule B). Molecule A may be the same molecule as molecule B. The crosslinking bonds may be covalent or ionic. In some embodiments of the instant invention, cross linkers include PLL/PLK, PS, and PEI.

As used herein, the term "cation" carries the normal meaning as understood by a person having ordinary skill in the art. Cation includes molecules that carry a positive, or partially positive, charge. Cation can include monomers and macromers including Cellfectin, chitosan (CS), Epigallocatechin gallate (ECGC), and poly(lactide-co-glycolide) (PLGA).

The following abbreviations are used herein: "PLL" and "PLK" are used interchangeably and refer to poly-L-lysine. "PEI" refers to polyethyleneimine. The term "PLGA" refers to poly(lactide-co-glycolide). The term "PS" refers to protamine sulfate. The term "Cf" refers to cellfectin. The term "CS" refers to chitosan.

EXAMPLES

The presently-disclosed subject matter is further illustrated by the following specific but non-limiting examples. The following examples may include compilations of data that are representative of data gathered at various times during the course of development and experimentation related to the present invention.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1—Materials & Methods

Preparation and Characterization of PLK:EGCG:dsRNA Polyplexes

The Natural polyphenol epigallocatechin-3-o-gallate (EGCG) was preincubated with dsRNA prior to mixing with the poly-l-lysine (PLK). The dsRNA was mixed with different amounts of EGCG for 30 min at room temperature. Then PLK was added to the solution and vortexed for 10 s, and incubated for 30 min with shaking 300 rpm at room temperature. The solution was centrifuged at 13,000 rpm for 10 min, the supernatant was discarded, and the pellet was washed three times with deionized water. The polyplexes were analyzed by 1% agarose gel electrophoresis. The size and zeta potential of the prepared polyplexes were determined by dynamic light scattering (Zetasizer Nano ZS90, Malvern). The morphology of polyplexes was determined by transmission electron microscopy.

Determination of dsRNA Loading Efficiency

To determine the dsRNA loading efficiency of polyplexes, after the formation of the PLK:EGCG:dsRNA polyplexes, free dsRNA in the supernatants was quantified by measuring absorbance at 260 nm wavelength using UV-vis spectrophotometer. The amount of incorporated dsRNA was calculated by the difference between the initial quantity of dsRNA (Total dsRNA) and the amount of dsRNA in the supernatant (Free dsRNA). The supernatant recovered from naked polyplexes was used as a blank. Entrapment efficiency was calculated using the following formula: Entrapment efficiency (EE %)=Total dsRNA−Free dsRNA/Total dsRNA×100.

Storage Stability of PLK:EGCG:dsRNA Polyplexes

PLK:EGCG:dsRNA polyplexes were resuspended in deionized water and stored at 25° C., 4° C., and −20° C. for 10 days. The storage stability of polyplexes was determined by 1% agarose gel electrophoresis and by measuring the size and charge of polyplexes at pre-determined time points. Degradation of EGCG in polyplexes was determined by visual observation.

Luciferase Assay

A luciferase assay was performed in order to test the efficiency of the PLK:EGCG:dsRNA polyplexes. Sf9 (a cell line developed from *Spodoptera frugiperda*) stable cells expressing the luciferase (Sf9_LUC) gene were seeded in 48-well plates at $0.05 \times 10^6$ cells/well. The cells were exposed to different ratios of PLK:EGCG:dsLUC (Batch I, II, III, and IV). After three days, the cells were washed with 1×PBS and 200 µl of lysis buffer was added to each well, and the plate was placed on a shaker for 10 min to induce lysis. Twenty microliters of cell lysate was used for measuring the luciferase activity and determining the protein concentration using Bradford's assay. The luciferase activity was measured using a SpectraMax® i3x multi-mode plate reader (Molecular Devices, Sunnyvale, Calif.). The protein content, which is an indicator of cell numbers and activity, was used to normalize the luciferase activity and expressed as RLU/mg protein. Endosomal escape study using CypHer-5E labeled dsRNA Sf9 cells ($1 \times 10^5$) were seeded into 8-well chamber slides. Twenty nanograms of CypHer-5E labeled dsGFP prepared as naked dsGFP, EGCG:dsGFP, PLK:dsGFP and PLK:EGCG:dsGFP complexes were mixed with 100 µl fresh SF900II SFM medium and exposed to the cells. At 4 h after adding complexes, the cells were washed twice with 1×PBS and fixed with 4% paraformaldehyde solution for 15 min at RT. The fixed cells were stained with EverBrite™ mounting medium containing DAPI (Biotium, Inc. Fremont, Calif.) and covered with coverslips. The cells were visualized under 63× magnification under a confocal laser scanning microscope (Leica, TCS SP8) using DAPI (for nuclei), Alexa 633 (for CypHer-5E_dsRNA) and bright field (BF) filters.

Transfection Studies

Aag-2 cells were seeded in 24-well plates at 50,000 cells/well and transfected with 1 µg of dsRed plasmid DNA prepared as PLK:EGCG:DNA polyplexes. The cells were photographed under a fluorescence microscope at 48 h after addition of polyplexes.

Knockdown Studied in Aag-2 Cells

For gene silencing study, $6 \times 10^5$ Aag-2 cells were seeded in each well of 6-well culture plates and treated with PLK:EGCG:dsIAP or PLK:EGCG:dsGFP at 24 h after plating. At 48 h after addition of polyplexes, the cells were harvested and the total RNA was isolated using TRI Reagent (Molecular Research Center Inc., Cincinnati, Ohio). The total RNA was then treated with DNase I (Ambion Inc., Austin, Tex.). Two micrograms of total RNA was used for cDNA synthesis using M-MLV Reverse Transcriptase (Invitrogen, USA). The cDNA was used as a template for quantitative PCR (qPCR) analysis. Each qPCR reaction (10 µl final volume) contained 5 µl of Fast Start SYBR Green Master (Roche Diagnostics, Indianapolis), 2 µl of 1:2 diluted cDNA and 0.2 µl each of 10 µM forward and reversed gene-specific primers. An initial incubation of 95° C. for 3 min, followed by 40 cycles of 95 for 10 sec, 55 for 20 sec and 72 for 30-sec settings, were used. Each experiment was repeated at least three times using the samples from independent treatments. Relative expression levels of a target gene were determined using the reference gene, S7RP the 2-$\Delta\Delta$CT method.

Determination of Stability of Polyplexes Exposed to Lumen Contents

To investigate the degradation of polyplexes in the lumen of *Ae. aegypti* alimentary canal, alimentary canals from *Ae. aegypti* larvae were dissected, washed and gently crushed in 100 µl of 1×PBS and centrifuged for 10 min at 20,000×g. The supernatant was centrifuged again for 10 min at 20,000× g. Ten microliters of polyplexes containing 1 µg dsRNA were added to 10 µl (1 µg) of lumen contents and the samples were collected at various time points (1, 3, 6, 12 and 24 h). As a control, naked dsRNA was incubated with the lumen contents for 1 h. The samples were resolved on 1.0% (w/v) agarose gel, stained with ethidium bromide and photographed using Alpha Imager™ Gel Imaging System (Alpha Innotech, San Leandro, Calif.) under UV light.

Mosquito Rearing

*Ae. aegypti* (LVPIB12 strain) were reared as described previously[27]. Eggs were collected from lab colony adults and stored dry for approximately 2-4 weeks before hatching. Eggs were hatched in a 64 oz plastic pan containing 300 mL deoxygenated, filtered water inoculated with 10 mL of bovine liver powder feeding solution (60 g-L). The pans were maintained in an incubator at 27±1.0° C. under a photoperiodic regime of 16:8 hour (L:D). Freshly molted second-instar larvae were collected and briefly held in a separate pan containing filtered water before being transferred to 24-well plates for bioassays.

dsRNA Synthesis

TABLE 1

List of primers used in the invention

| S. No | Genes | Primer sequences (5'-3') | Amplicon Size (bp) | Accession No |
|---|---|---|---|---|
| 1. | IAP1 | FP: CTTCTGCCGAGTGGAAATCGG (SEQ ID NO: 1) | 349 | DQ993355.1 |
|  |  | RP: ATATTCCGGTAGCTTCTGTTG (SEQ ID NO: 2) |  |  |
|  |  | qPCR-FP: GTGTTTGGCCAAGAAGGAAAG (SEQ ID NO: 3) | 118 |  |
|  |  | qPCR-RP: TGACTGAAGCGAGGATGTTG (SEQ ID NO: 4) |  |  |
| 2. | SNF7 | FP: ACGATGTCCACGAGATGATG (SEQ ID NO: 5) | 222 | XM_001659907.2 |
|  |  | RP: CAGGCAGATCGGTTGCT (SEQ ID NO: 6) |  |  |
| 3. | SRC | FP: CGTCAAATGCAGCAGATCACCCAA (SEQ ID NO: 7) | 431 | XM_021845577.1 |
|  |  | RP: TGTTGGTTGTTCGAGGGAGAAGGT (SEQ ID NO: 8) |  |  |

TABLE 1-continued

List of primers used in the invention

| S. No | Genes | Primer sequences (5'-3') | Amplicon Size (bp) | Accession No |
|---|---|---|---|---|
| 4. | S7RP | qPCR-FP: ACCGCCGTCTACGATGCCA (SEQ ID NO: 9)<br>qPCR-RP: ATGGTGGTCTGCTGGTTCTT (SEQ ID NO: 10) | 131 | CR938234.1 |

Nine candidate genes were selected based on the previous reports on their efficacy as RNAi triggers. The dsRNA targeting these genes was in vitro synthesized using the MEGAscript RNA synthesis kit (Ambion Inc., Foster City, Calif. USA) as described previously[55]. Briefly, 300-500 bp fragment of each gene was PCR amplified using gene-specific primers (Table 1) containing T7 RNA polymerase sequence at the 5' end. 500 ng of the purified PCR product was used as a template in 20 μL in vitro transcription reaction. The reaction mix was incubated for 16 h at 37° C., followed by 30 min of DNase I treatment. The reaction mixture was heat inactivated at 70° C. for 10 min and cool down slowly to room temperature. The dsRNA was precipitated by adding 0.1× volume of sodium acetate (3M, pH 5.2) and 2.5× the volumes of 100% ethanol and kept at −20° C. for at least 2 h. The reaction contents were then centrifuged at 4° C. for 15 min. The dsRNA pellet was rinsed with 75% ethanol and centrifuged again at 4° C. for 5 min. The ethanol was removed, and the dsRNA pellet was dried and resuspended in milliQ water. The quality and quantity of dsRNA were checked by agarose gel electrophoresis and NanoDrop-2000 spectrophotometer (Thermo Fisher Scientific Inc., Waltham, Mass.), respectively.

Mosquito Feeding Assay

Mosquito larval food containing dsRNA polyplexes were prepared as described previously. Briefly, 50 μl of polyplexes containing 40 μg of dsRNA were mixed with 5 mg of bovine liver powder and 1.5% pre-melted agarose gel solution at 55° C. was added to the mixer. A group of 5-7-second instar larvae were transferred to each well of 24-well plate containing 1 ml of deionized water. Each treatment was replicated three times, and each experiment was repeated at least five times. The food pellet containing 40 μg of dsRNA was divided into three equal pieces and distributed to each well. Food containing dsRNA. Mortality was recorded until the control mosquito larvae became adults. The mRNA levels of dsIAP target gene were determined on the 5th day after initiation of the feeding of dsRNA.

Quantitative Real-Time PCR (RT-qPCR)

Total RNA was isolated from mosquito larvae using TRIzol reagent (Molecular Research Center Inc., Cincinnati, Ohio) following the manufacturer's protocol. The total RNA was then treated with DNase I (Ambion Inc., Austin, Tex.). Two micrograms of total RNA was used for first strand cDNA synthesized using M-MLV Reverse Transcriptase (Invitrogen, USA). The first strand cDNA was used as a template for qPCR analysis. Each qRT-PCR reaction (10 μl final volume) contained 5 μl of Fast Start SYBR Green Master (Roche Diagnostics, Indianapolis), 2 μl of 1:2 diluted cDNA and 0.2 μl each of 10 μM forward and reversed gene-specific primers (Table 1). An initial incubation of 95° C. for 3 min, followed by 40 cycles of 95 for 10 sec, 55 for 20 sec and 72 for 30-sec settings, were used. Each experiment was repeated at least three times using the samples from independent treatments. Relative expression levels of a target gene were determined using the reference gene, S7RP the $2^{-\Delta\Delta CT}$ method.

Statistical Analysis

Data are presented as the mean±standard deviation. The statistical significance was determined using an independent sample t-test or one-way analysis of variance (ANOVA). P values of <0.05 were considered significant. The statistical analyses were carried out using SPSS version 12.0 for Windows.

Results

Preparation and Characterization of PLK:dsRNA Polyplexes

Figure 1B:
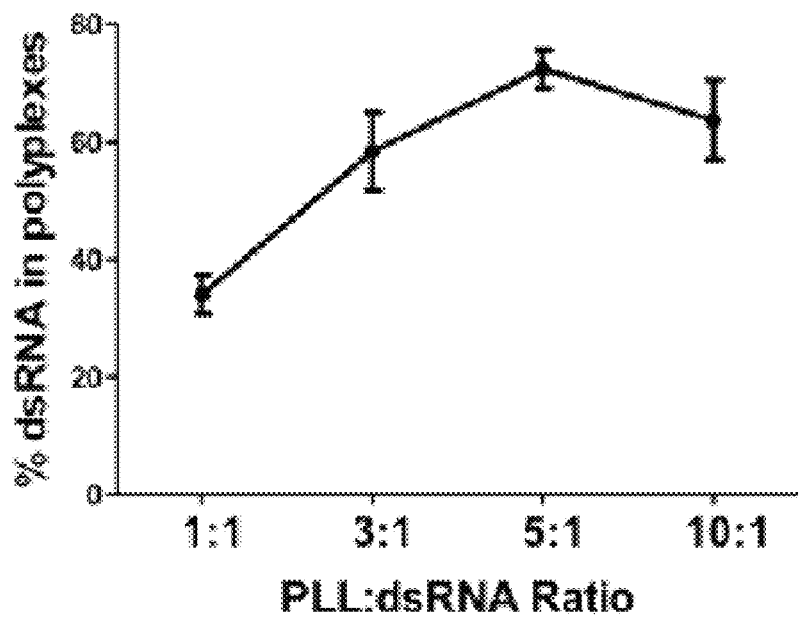
FIG. 1B shows synthesis and characterization of PLK: dsRNA polyplexes. Percent dsRNA in polyplexes prepared using 1 µg dsRNA and 1-10 µg PLK. Mean±S.E (n=5) are shown.
Figure 1C:
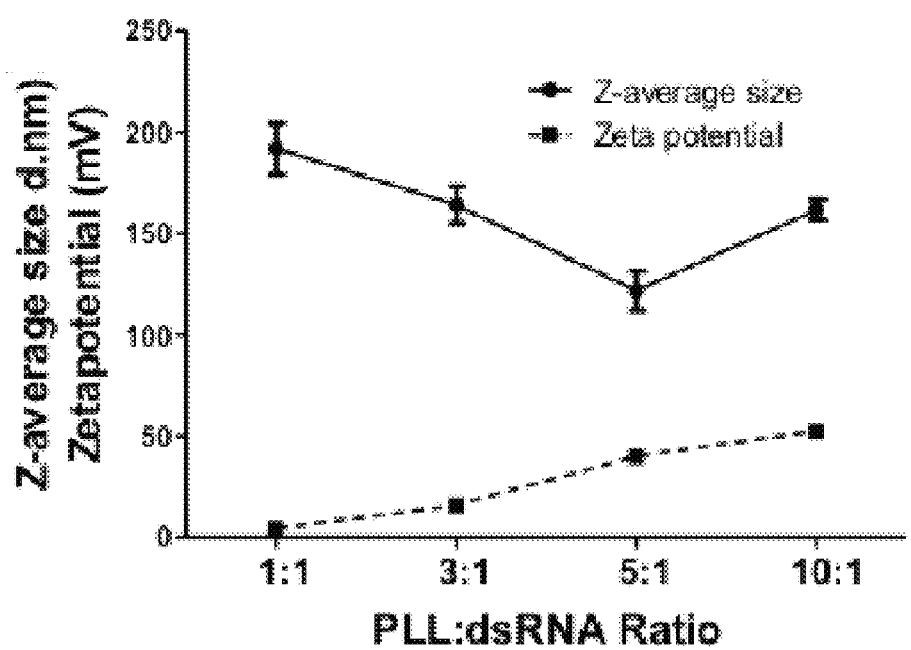
FIG. 1C shows synthesis and characterization of PLK: dsRNA polyplexes. DLS analysis of PLK:dsRNA polyplexes. The z-average size and zeta potential are shown.
Figure 1D:
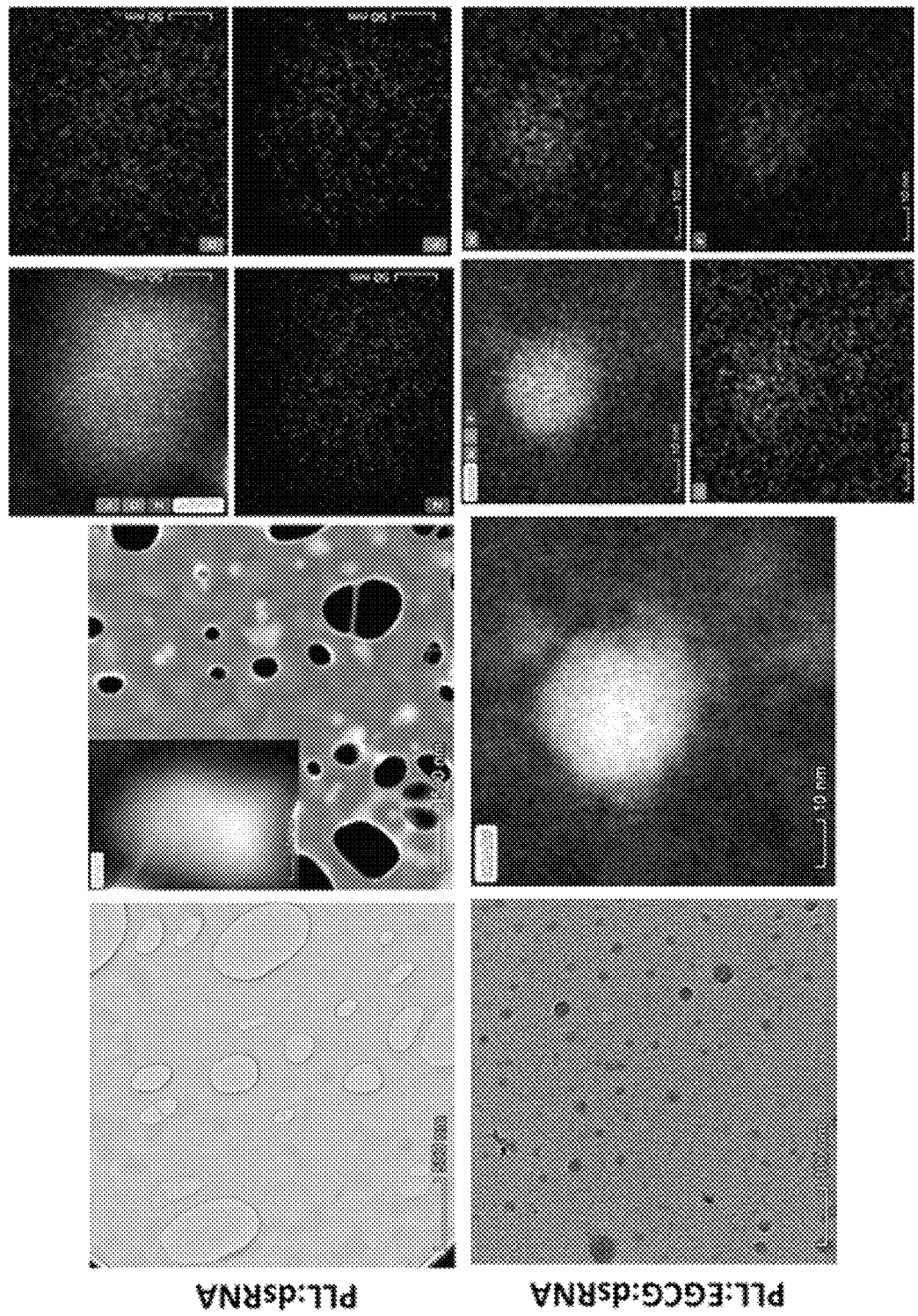
FIG. 1D shows synthesis and characterization of PLK: dsRNA polyplexes. Transmission electron microscopy analysis of PLK:dsRNA polyplexes. The PLK:dsGFP (1:5) polyplexes were placed on a grid, stained and photographed under a transmission electron microscope using STEM and Elemental analysis modes. Transmission electron microscopy analysis of PLL:dsRNA and PLL:EGCG:dsRNA nanoparticles. A drop of PLL:dsRNA and PLL:EGCG:dsRNA nanoparticles on the copper microgrid was negatively stained with 2% phosphotungstic acid and photographed under a Talos F200X TEM (Scale bar=500 nm and 100 nm). A higher magnification view of a single particle photographed under a STEM and elemental analysis was performed. (Scale bar=50 nm and 10 nm).

One microgram of dsRNA mixed with 1-10 μg of PLK was used to prepare polyplexes. The polyplexes were evaluated using agarose gel electrophoresis, DLS and transmission electron microscopy. dsRNA mixed with PLK at a ratio of 1:1 to 1:10 formed polyplexes that showed retardation when resolved on 1% agarose gels (FIG. 1a). The incorporation of dsRNA into polyplexes increased with an increase in PLK concentration and reached the maximum levels at a 5:1 ratio of PLK:dsRNA (FIG. 1b). The average size of the polyplexes decreased with an increase in PLK concentration and reached the lowest size at a 5:1 ratio of PLK:dsRNA. The size of the polyplexes then increased at a 10:1 ratio of PLK:dsRNA (FIG. 1c). The zeta potential of the polyplexes increased with an increase in the concentration of PLK (FIG. 1c). Electron microscopy analysis showed distinct spherical shape polyplexes of about 50 nm diameter containing oxygen, nitrogen and phosphorus confirming the presence of dsRNA and PLK in the polyplexes (FIG. 1d).

Evaluation of PLK:dsRNA Polyplexes

Figure 2:
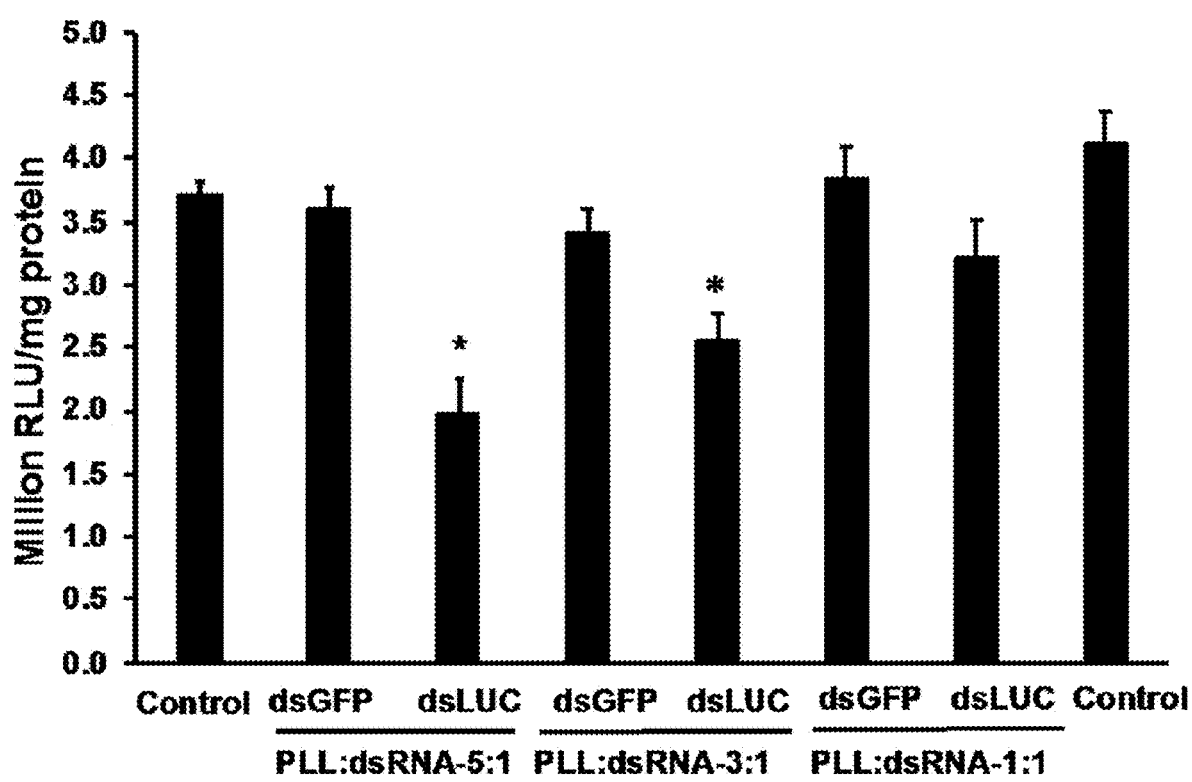
FIG. 2 shows Knockdown of the luciferase gene by PLK:dsRNA polyplexes. PLK:dsLUC polyplexes prepared using 1 µg dsLUC and 1, 3 or 5 µg PLK were evaluated for their knockdown efficiency. SD cells expressing the luciferase gene were exposed to PLK:dsLUC or PLK:dsGFP polyplexes. Three days after adding polyplexes, the cells were harvested, lysed and the luciferase and protein concentrations were determined. Mean RLU/mg protein±S.E (n=5) are shown.
Figures 3A, 3B:
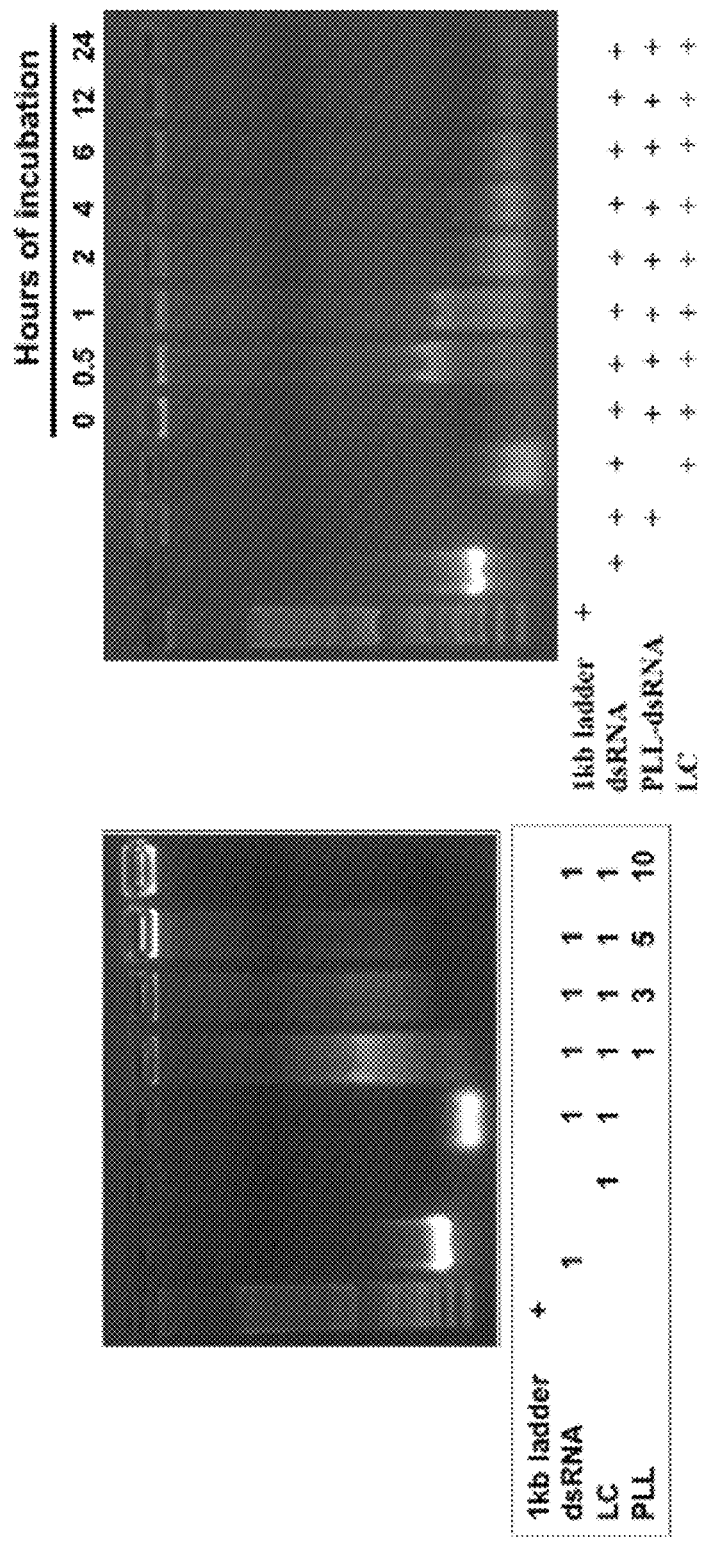
FIG. 3A shows PLK:dsRNA polyplexes stability and performance in *Ae. aegypti*. Polyplexes prepared using 1 µg dsRNA and 1-10 µg PLK were incubated for 1 h with 1 µg of lumen contents collected from *Ae. aegypti* larvae. The products were analyzed by 1% agarose gel electrophoresis.
FIG. 3B shows PLK:dsRNA polyplexes stability and performance in *Ae. aegypti*. Polyplexes prepared using 1 µg dsRNA and 5 µg PLK were incubated for 0-24 h with 1 µg of lumen contents collected from *Ae. aegypti* larvae. The products were analyzed by 1% agarose gel electrophoresis.
Figure 4B:
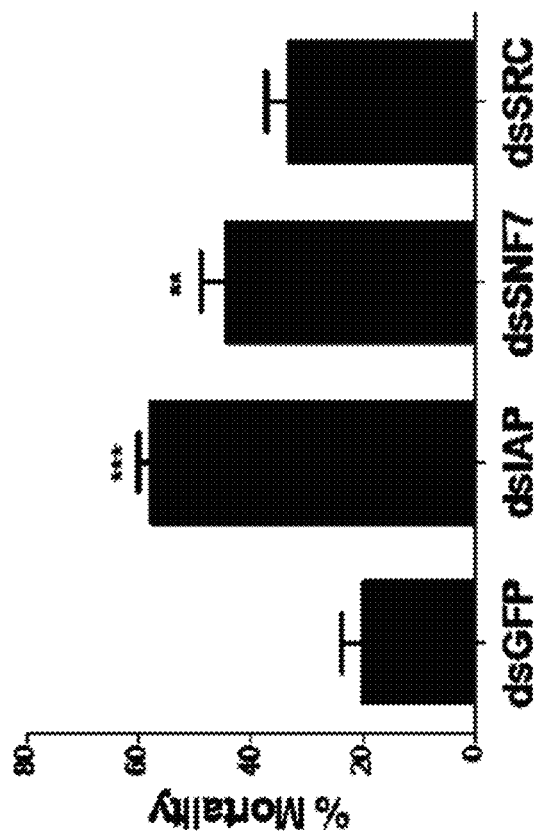
FIG. 4B shows *Ae. aegypti* larvae were fed on PLK:dsIAP or PLK:dsGFP polyplexes. Mortality was recorded on the 10th day after initiation of feeding. Mean±S.E (n=3). The asterisks above the bar indicate a significant difference in mortality (One-way ANOVA, Turkey's test $P<0.05$, *=$P<0.01$).
Figure 4A:
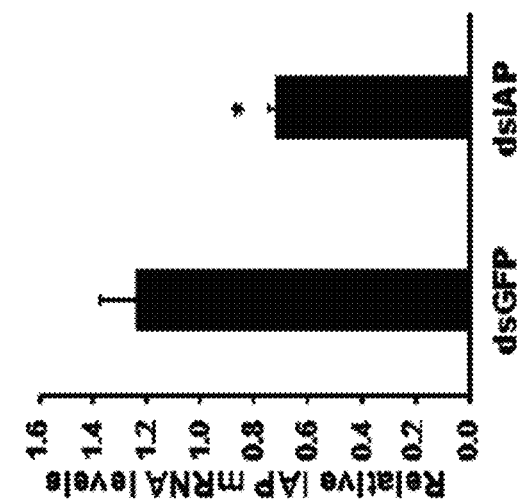
FIG. 4A shows PLK:dsIAP polyplexes induce knockdown of target gene and mortality in *Ae. aegypti* larvae. RT-qPCR analysis of knockdown of AaIAP gene in *Ae. aegypti* larvae fed on PLK:dsIAP or PLK:dsGFP polyplexes. Five days after feeding of PLK: dsIAP or PLK:dsGFP, the RNA was isolated, converted to cDNA and used in RT-qPCR to determine relative IAP mRNA levels. Data shown are mean±SE. (n=6).

The PLK:dsRNA polyplexes were evaluated for their gene knockdown efficiency in both cell line and mosquito larvae. Polyplexes were prepared using 1 μg of dsRNA targeting the luciferase gene (dsLUC) and 1-5 μg of PLK were evaluated in Sf9 cells expressing the luciferase gene. As shown in FIG. 2, PLK:dsRNA at 5:1 ratio induced the maximum reduction in the expression of luciferase when compared to the cells exposed to PLK:dsGFP (dsRNA targeting the gene coding for the green fluorescent protein was used as a control). The PLK:dsLUC polyplexes at 3:1 and 1:1 also knocked down the luciferase gene but at lower levels compared to the knockdown induced by 5:1 ratio polyplexes (FIG. 2). To determine the rate of release of dsRNA from the polyplexes in the lumen of the mosquito alimentary canal, the polyplexes prepared using PLK:dsRNA at 1:1, 1:3, 1:5 and 1:10 ratios were incubated with 1 μg protein from lumen contents of mosquito larvae. The polyplexes were incubated at room temperature for one hour followed by their separation on 1% agarose gels. The dsRNA release from polyplexes occurred within an hour of exposure to lumen contents, and the dissociation of dsRNA was maximum at a1:1 ratio of PLK:dsRNA and decreased gradually with an increase in PLK concentration until no dsRNA release was observed at 10:1 PLK:dsRNA ratio (FIG. 3a). To determine time-course of dsRNA release, polyplexes prepared using a 5:1 ratio of PLK:dsRNA were incubated with 1 µg lumen contents and the products were resolved on 1% agarose gels. As shown in FIG. 3b, the dsRNA was released from polyplexes within 30 min, suggesting that most of the dsRNA may be released from polyplexes rapidly. To determine the efficacy of polyplexes in knocking down the target gene and inducing mortality, the polyplexes prepared using a 5:1 ratio of PLK:dsRNA (dsIAP or dsGFP) were fed Ae. Aegypti larvae. The knockdown efficiency was determined on day 5 and mortality was recorded on day 10 after initiation of feeding polyplexes. Feeding dsIAP polyplexes caused more than 50% knockdown of IAP genes resulting in the death of 60% of the larvae (FIGS. 4a&b). dsRNA targeting two additional genes, SNF7 and SRC, were also tested which induced 50 and 40% mortality, respectively (FIG. 4b).

Addition of EGCG Improves PLK:dsRNA Polyplexes

Figures 5A, 5B:
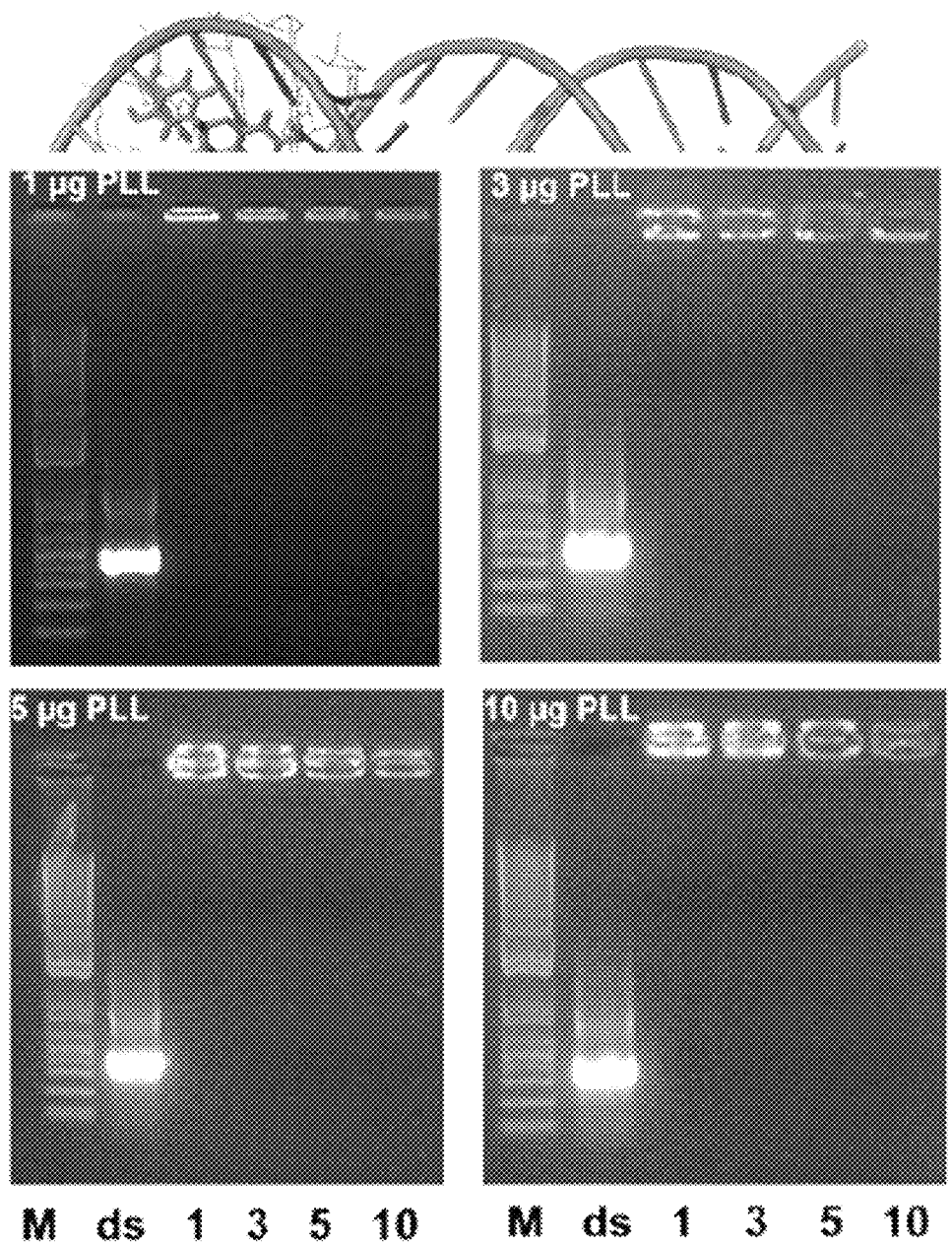
FIG. 5A shows the interactions between PLK:EGCG: dsRNA. Model for dsRNA and EGCG interactions.
FIG. 5B shows Polyplexes prepared using 1 µg dsRNA, 1, 3, 5 or 10 µg PLK and 1, 3, 5 and 10 µg EGCG were evaluated by 1% agarose gel electrophoresis.
Figure 5C:
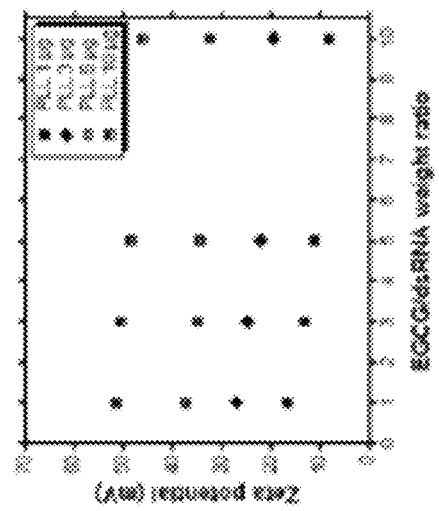
FIG. 5C shows Polyplexes prepared using 1 µg dsRNA, 1, 3, 5 or 10 µg PLK and 1, 3, 5 and 10 µg EGCG were evaluated by DLS to compare percent dsRNA, Z-average size, Zeta potential and PDI.
Figure 5C:
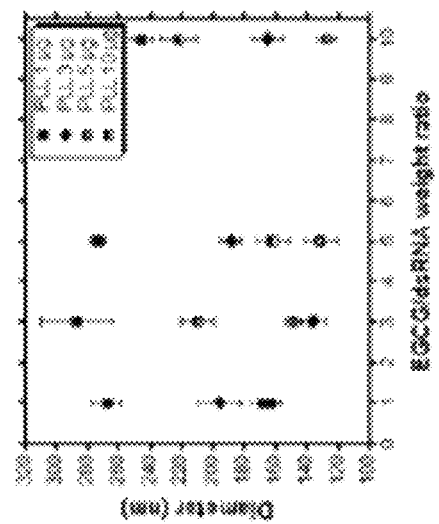
Figure 5C:
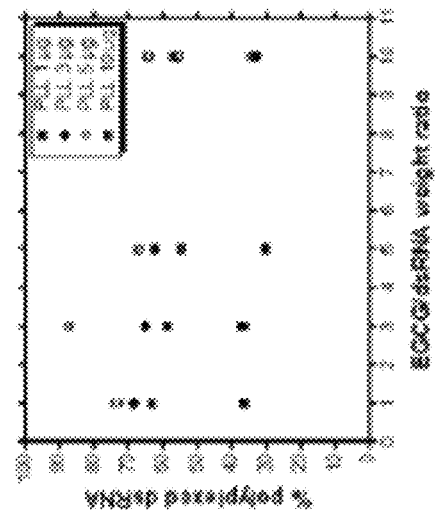

A natural polyphenol, (−) epigallocatechin-3-O-gallate (EGCG) is a major ingredient of green tea. The polyphenolic structure of EGCG enables strong affinity to dsRNA via hydrogen-bond and hydrophobic interactions (FIG. 5a). Adding EGCG to PLK:dsRNA polyplexes was tested to determine if it would increase stability resulting in slow release of dsRNA to improve gene knockdown and mortality. The polyplexes were prepared by mixing dsRNA with EGCG to yield a negatively charged core. Then, the ECCG:dsRNA core was coated with a cationic polymer PLK to form the shell. The polyplexes prepared using 1 µg dsRNA and varying concentrations of EGCG (1, 3, 5 and 10 µg) and PLK (1, 3, 5 and 10 µg) were evaluated by gel electrophoresis. The positive charge of PLK can neutralize the negative charges of the phosphate groups within the EGCG-dsRNA complexes, thus retarding the dsRNA mobility. Naked dsRNA was used as the control group. dsRNA bands decreased with increasing N/P ratios (from 1 to 10). This indicates that the negatively charged EGCG-dsRNA complexes could be neutralized entirely at this N/P value. Increasing the PLK content resulted in the formation of decreasing nanoparticle size with higher zeta potentials due to the negative charge of the EGCG-dsRNA complexes. The low zeta potential nanoparticles could form aggregates and precipitates through low electrostatic repulsion, resulting in higher particle sizes and PDI. The smaller sized nanoparticles exhibited improved absorption of dsRNA compared to larger size nanoparticles. All of the complexes tested bound to dsRNA, but increasing concentrations of PLK increased the dsRNA in the polyplexes. Also, an increase in the concentration of EGCG resulted in a decrease in the amount of dsRNA detected in the polyplex (FIG. 5b). Similar results were obtained when dsRNA in the polyplexes was calculated after measuring the dsRNA left in the supernatant by spectrometry (FIG. 5c). Measuring size and charge of polyplexes prepared using different ratios of PLK:EGCG:dsRNA decrease in size and charge with an increase in the concentration of EGCG (FIG. 5c).

Figure 6:
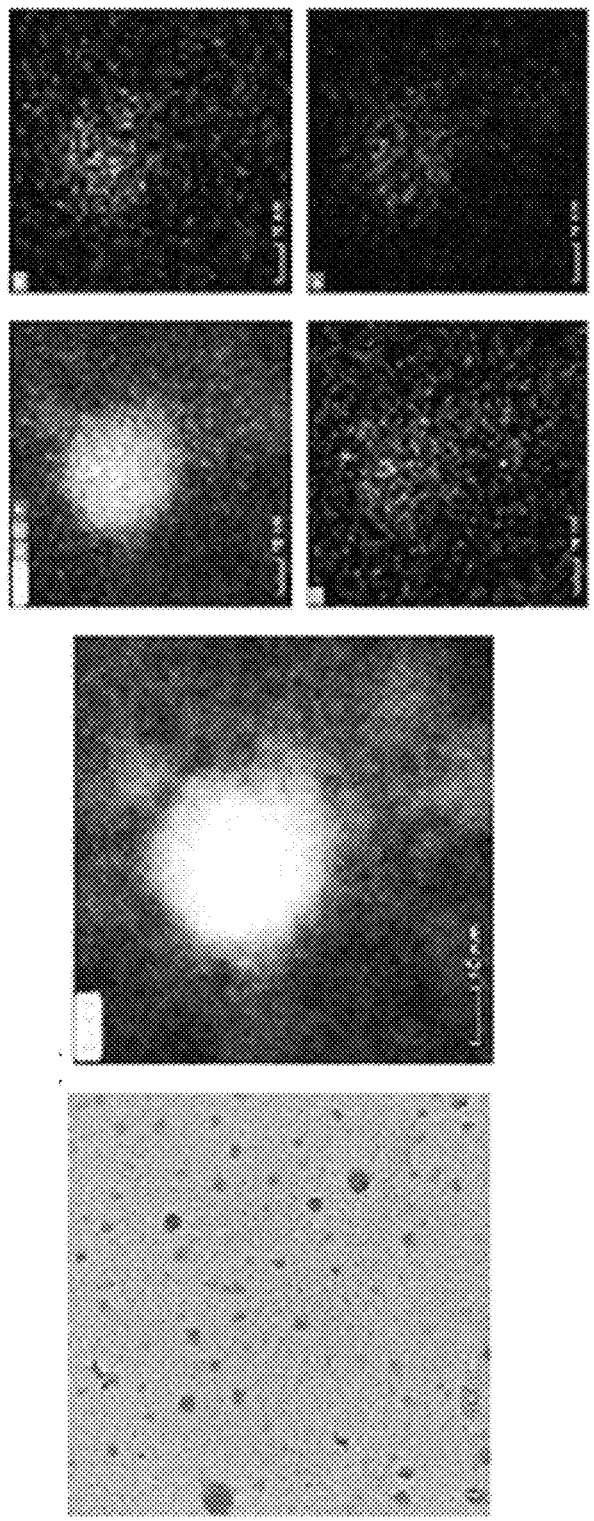
FIG. 6 shows transmission electron microscopy analysis of PLK:EGCG:dsRNA polyplexes. The PLK:EGCG:dsGFP (5:3:1) polyplexes were placed on a grid, stained and photographed under a transmission electron microscope using STEM and Elemental analysis modes
Figure 7:
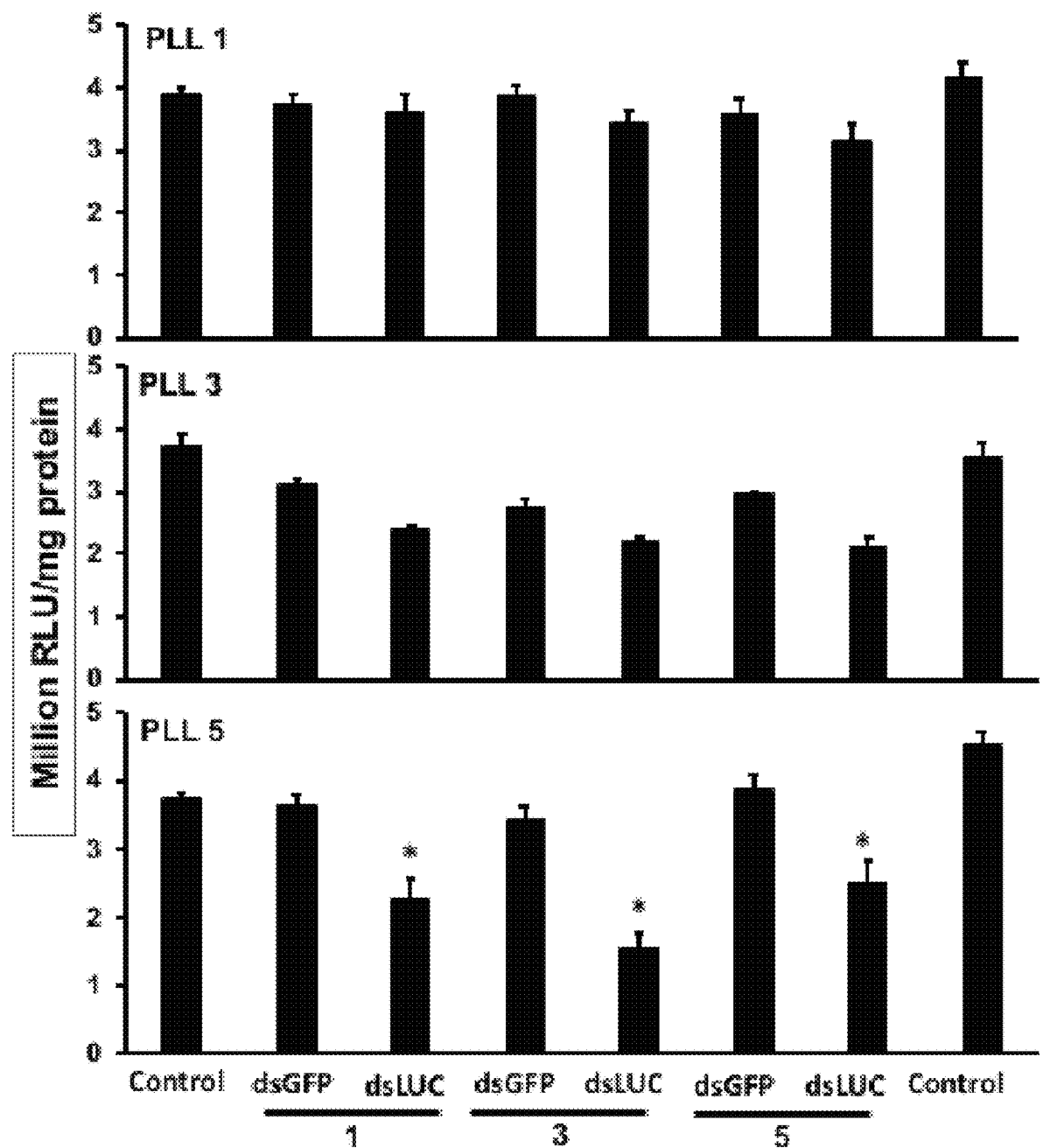
FIG. 7 shows Knockdown efficiency of PLK-dsRNA and PLK-EGCG-dsRNA polyplexes in Sf9 cells expressing the luciferase gene. One µg of the dsLUC, 1, 3, 5 µg of PLK and 1, 3, or 5 µg of EGCG were added to cells and the luciferase activity was measured at 48 h after adding polyplexes. The percent of the reduction in the luciferase activity was calculated by comparing its expression in control cells exposed to polyplexes containing dsGFP with that in cells treated with dsLUC containing complexes. The bars show Mean±S.D (n=6). *=significantly different at a P-value <0.05.
Figure 8B:
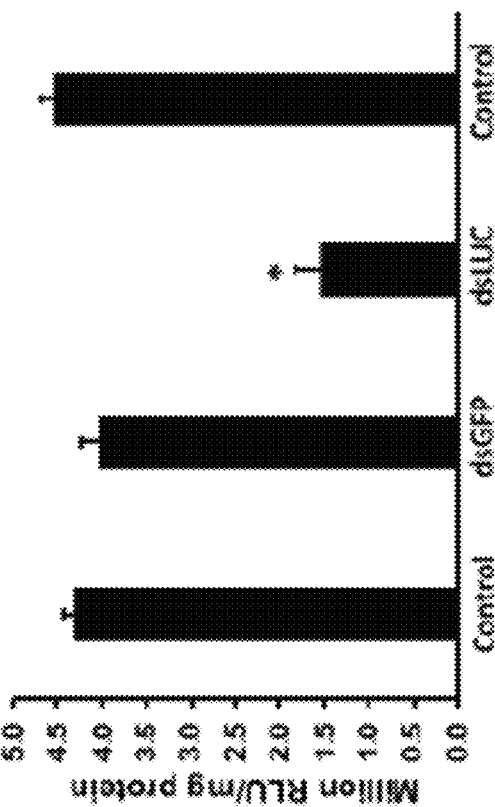
FIG. 8B shows Stability and efficacy of PLK:EGCG: dsRNA polyplexes. Knockdown of target genes by PLK-EGCG-dsRNA polyplexes. The polyplexes prepared using 5:3:1 ratio of PLK:EGCG:dsLUC were added to Sf9 cells. At 48 h after addition of complexes, the cells were harvested and the luciferase activity and the protein concentration were determined. The bars show Mean±S.D ((n=6). *=significantly different at a P-value <0.05
Figure 8A:
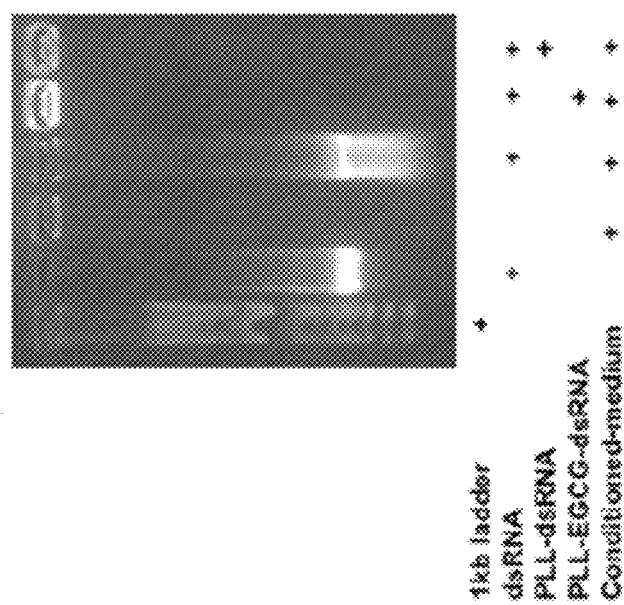
FIG. 8A shows Stability and efficacy of PLK:EGCG: dsRNA polyplexes. dsRNA polyplexes stability assay. One microgram of dsRNA containing polyplexes incubated with conditioned media. After one hour of incubation, the stability of polyplexes was checked by in 1% agarose gel electrophoresis.
Figure 9:
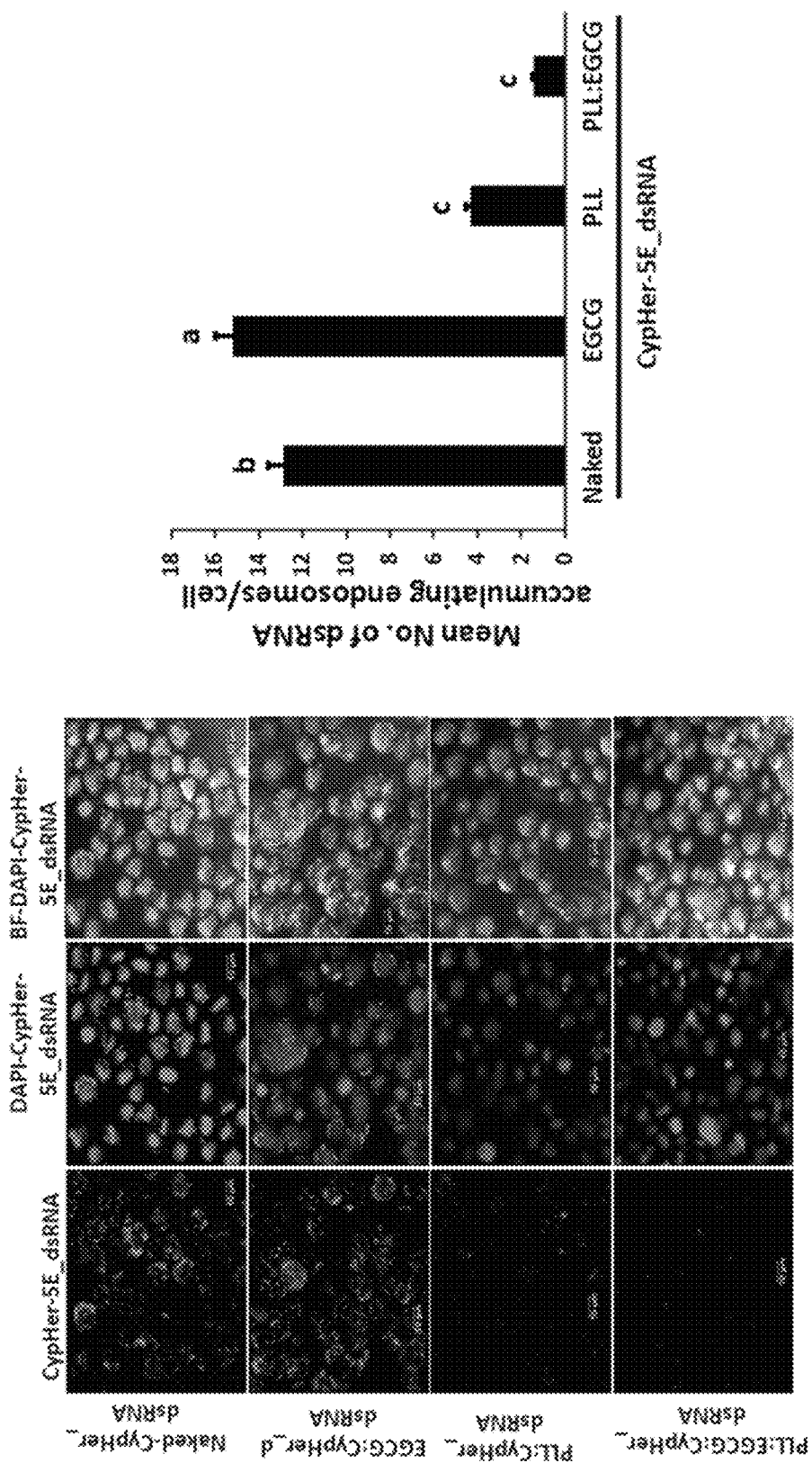
FIG. 9 shows EGCG in polyplexes helps with the endosomal escape of dsRNA. Cypher-5E labeled dsRNA was synthesized and used to prepare EGCG:dsRNA, PLK: dsRNA and PLK:EGCG:dsRNA polyplexes. Sf9 cells were exposed to polyplexes or naked dsRNA. At 72 h after addition of polyplexes, the cells were fixed, mounted on a slide and photographed under a confocal microscope. Specifically, CypHer_5E-labeled dsRNA conjugated to polyplexes reduces the accumulation of dsRNA in the endosomes of 519 cells. One hundred twenty thousand cells/well were seeded in 8-well chamber slides. The cells were exposed 25 ng naked CypHer 5E-labeled dsRNA or that conjugated to EGCG, PLL and PLL:EGCG polyplexes. The dsRNA and their complexes were mixed with Sf-900 II SFM medium and added to the cells. At 4 h after addition of dsRNA, the cells were washed, fixed and mounted using EverBrite mounting medium containing DAPI and visualized under Leica confocal microscope at 63× magnification (n=100; scale bar: 10 µm). (c) The number of CypHer-5E labeled dsRNA accumulating endosomes were counted and plotted (n=100).

Electron microscopy analysis of polyplexes at PLK-EGCG-dsRNA ratio of 5:3:1 showed distinct spherical shaped complexes of about 50 nm diameter containing oxygen, nitrogen, and phosphorus are confirming the presence of dsRNA and PLK in the polyplexes (FIG. 6). Polyplexes prepared using different ratios of PLK:EGCG:dsLUC were tested in Sf9 cells that express the luciferase gene. As shown in FIG. 7, the polyplexes prepared using 5:3:1 PLK:EGCG:dsLUC induced the highest knockdown of luciferase activity when compared to all other polyplexes tested. The polyplexes prepared using 5:1:1 and 5:1:5 ratios of PLK:EGCG:dsLUC also induced knockdown of the luciferase activity (FIG. 7). One microgram of dsRNA incorporated into PLK:EGCG:dsRNA (5:3:1) and PLK:dsRNA (5:1) ratio were tested for their stability in the conditioned medium where Sf9 cells were grown for three days. These cells release dsRNases which digest dsRNA. As shown in FIG. 8a, the addition of EGCG improved protection of polyplexes from dsRNase digestion. The same polyplexes tested in Sf9 cells expressing the luciferase gene showed that the polyplexes prepared using 5:3:1 PLK:EGCG:dsLUC induced knockdown of the luciferase activity (FIG. 8b). To test if the increase in knockdown of the target gene by EGCG containing polyplexes is due to the enhanced escape of dsRNA from endosomes, Cypher-5E labeled dsRNA was synthesized and used it to prepare EGCG:dsRNA, PLK:dsRNA and PLK:EGCG:dsRNA polyplexes. Sf9 cells were exposed to polyplexes or naked dsRNA. As shown in FIG. 9, the accumulation of Cypher labeled dsRNA was lowest in the cells exposed to PLK:EGCG:dsRNA polyplexes. The cells exposed to PLK:dsRNA polyplexes also showed lower accumulation of dsRNA when compared to those exposed to naked or EGCG:dsRNA.

Figure 10:
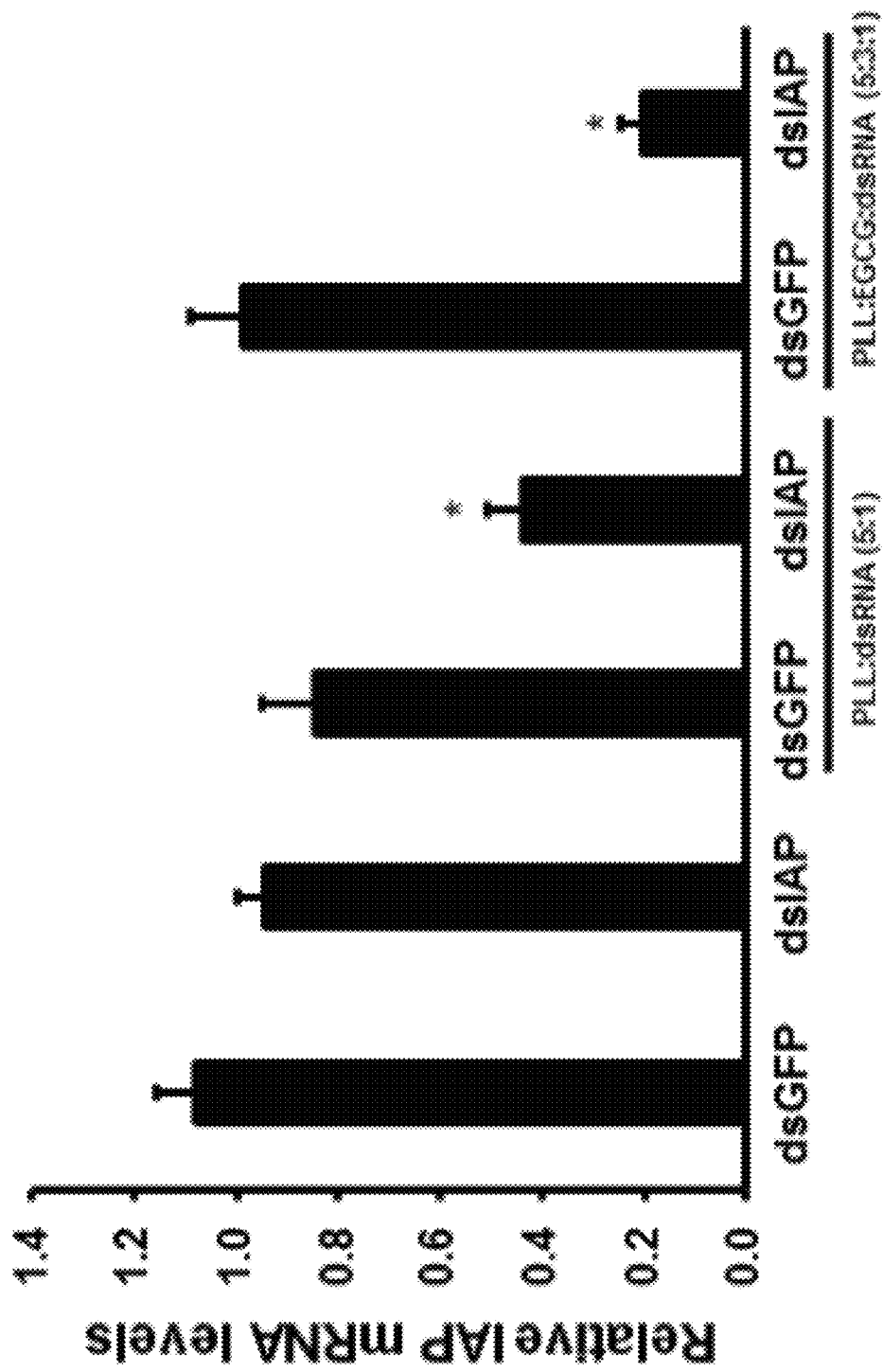
FIG. 10 shows PLK:EGCG:dsIAP polyplex efficiently knockdown iap gene in Aeg-2 cells. One microgram of naked dsIAP or that in PLK:EGCG:dsIAP polyplexes was added to $2 \times 10^5$ Aeg-2 cells. After 72 h after adding dsRNA, the cells were harvested, RNA isolated and used in RT-qPCR to determine IAP mRNA levels. The bars show Mean±S.D (n=3). *=significantly different at a P-value <0.05
Figure 11:
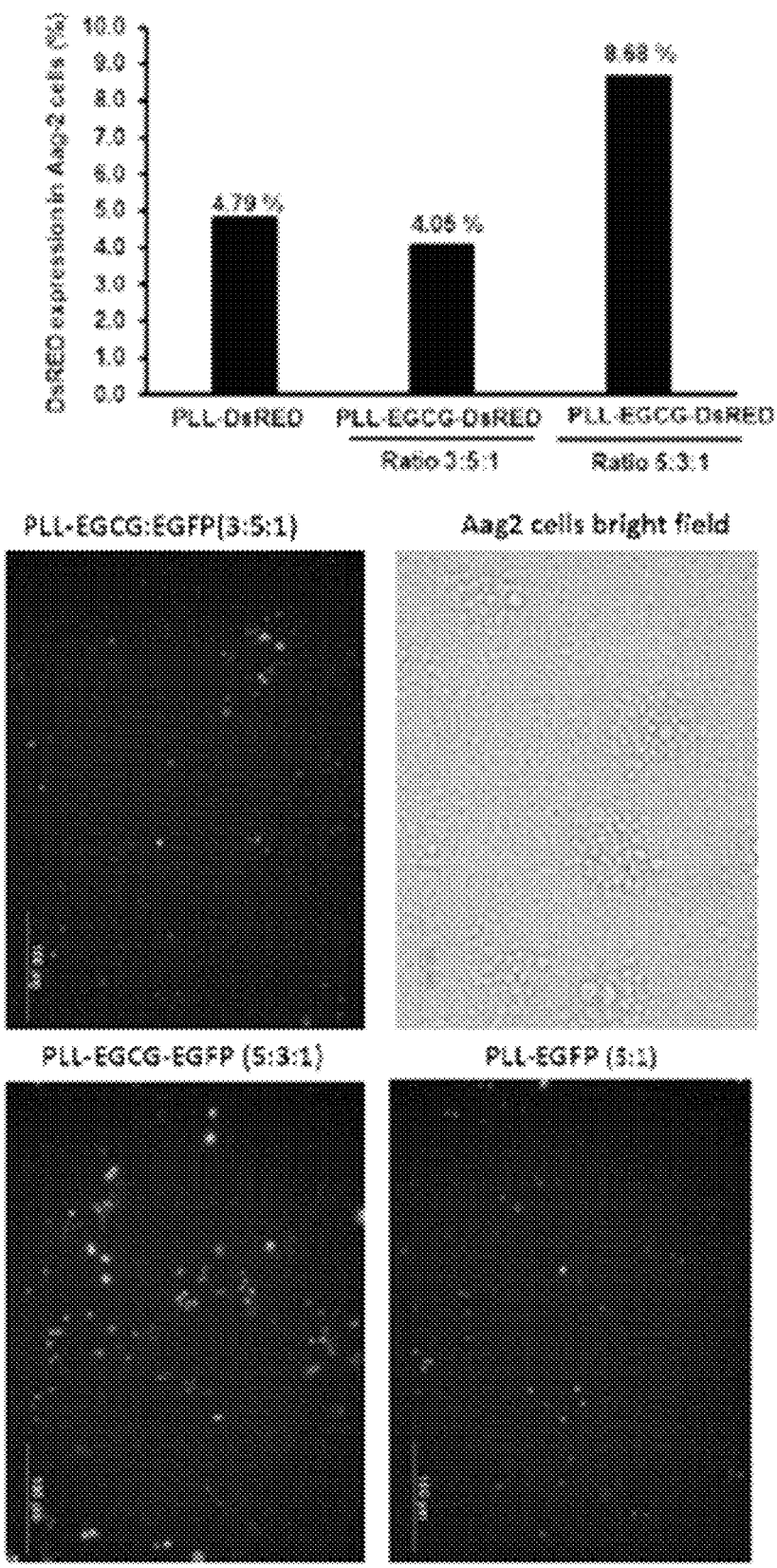
FIG. 11 shows. PLK:EGCG:DNA complexes efficiently transfect plasmid DNA into Aeg-2 cells. A plasmid expressing EGFP under the control of IE1 promoter was prepared as PLK:EGCG:EGFP, PLK:EGFP or EGCG:EGFP polyplexes. One microgram of EGFP plasmid DNA in polyplexes was added to 10,000 Aeg-2 cells and the cells were observed under a fluorescence microscope and photographed at 72 h after addition of complexes.

The polyplexes prepared using 1 µg dsIAP at 5:3:1 of PLK:EGCG:dsIAP but not naked dsIAP induced knockdown of the IAP gene in Aeg-2 cells (FIG. 10). One microgram of plasmid DNA expressing EGFP protein under the control of AcMNPV immediate early gene promoter, which is active in Aeg-2 cells, incorporated into PLK:EGCG:DNA polyplexes at ratios of 3:5:1 and 5:3:1. PLK:DNA polyplexes at ratio of 5:1 ratio were also tested for their transfection efficiency in Aeg-2 cells. The presence of EGCG ultimately improved transfection efficiency of polyplexes (FIG. 11).

Figure 12B:
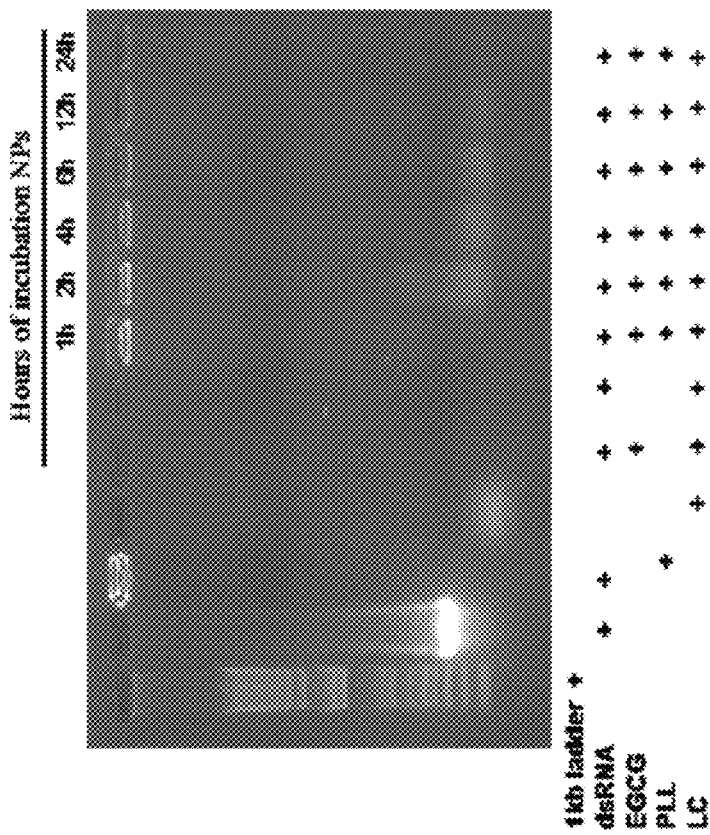
FIG. 12B shows stability of PLK:EGCG:dsRNA polyplexes in the lumen of Ae. aegypti. PLK-EGCG-dsRNA polyplexes stability assay in midgut juice, samples incubated midgut juice at different time intervals (1, 2, 4, 6, 12 and 24 h) samples were collected and stored −20° C. PLK-EGCG-dsRNA polyplexes stability was checked in 1% agarose gel electrophoresis.
Figure 12A:
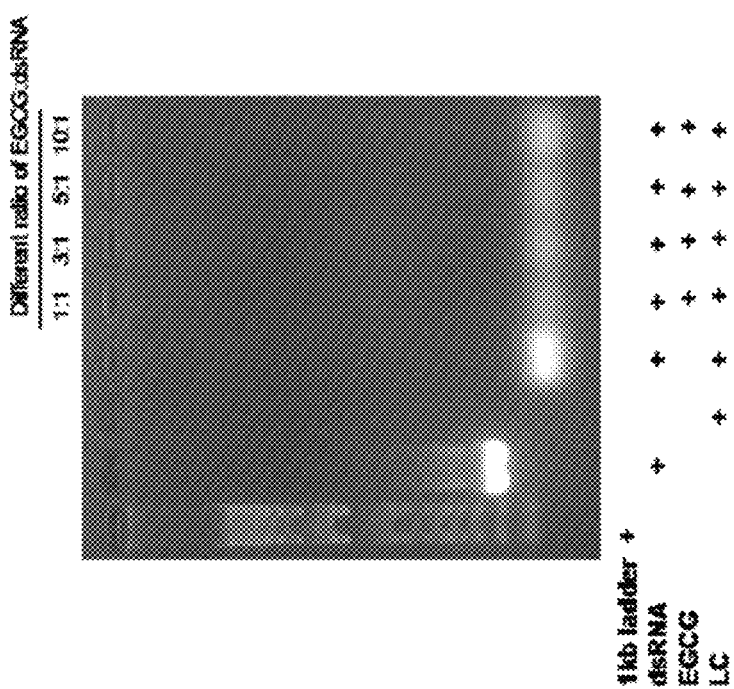
FIG. 12A shows stability of PLK:EGCG:dsRNA polyplexes in the lumen of *Ae. aegypti*. different ratio of EGCGdsRNA complexes incubated mosquito larvae midgut juice after 1 h samples were checked in 1% agarose gel electrophoresis.

To investigate the nuclease protection ability of PLK-EGCG-dsRNA polyplexes in vivo; the polyplexes were exposed to the contents from the lumen of the alimentary canal dissected from Ae. aegypti larvae. The nucleases present in the lumen of Ae. aegypti larvae degraded naked dsRNA and EGCG-dsRNA within one hour of the addition of lumen contents (FIG. 12a). In contrast, the PLK-EGCG-dsRNA polyplexes effectively protected dsRNA from nuclease degradation up to 24 h (FIG. 12b).

Figures 13A, 13B:
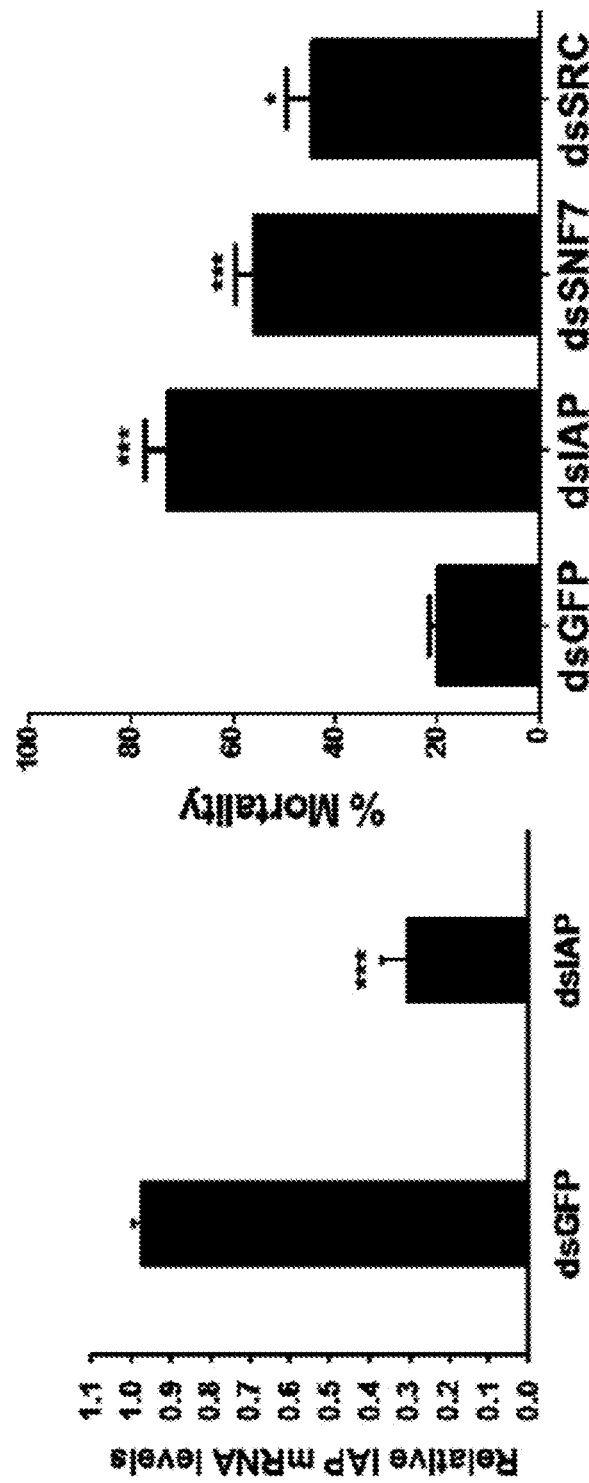
FIG. 13A shows in vivo performance of PLK:EGCG: dsRNA polyplexes. Ae. aegypti larvae were fed with each of the three different PLK-EGCG-dsRNA polyplexes targeting IAP, SNF7 or SRC genes or control PLK-EGCG-dsGFP polyplexes. The mortality rate was evaluated at 10 days after feeding. Mean±S.E (n=3). The asterisks above the bar indicate significant mortality (One-way ANOVA, Turkey's test P=<0.05, *=P=<0.001).
FIG. 13B shows in vivo performance of PLK:EGCG: dsRNA polyplexes. (b) Knockdown of AaIAP gene was analyzed in mosquito larvae fed with PLK-EGCG-dsIAP or PLK-EGCG-dsGFP polyplexes by qRT-PCR. Five days after feeding of PLK-EGCG-dsIAP polyplexes to Ae. aegypti larvae, the RNA was isolated, converted to cDNA and used in qRT-PCR to determine relative IAP mRNA levels. Data are presented as mean±SE. (n=3).

The effectiveness of PLK-EGCG-dsRNA polyplexes in silencing target genes and killing mosquito larvae was tested. Three candidate genes were selected based on their effectiveness in triggering RNAi in Ae. aegypti and other insects tested. The dsRNA derived from fragments of three selected genes and the gene coding for enhanced green fluorescence protein (EGFP) as a control were used to prepare PLK-EGCG-dsRNA polyplexes. The polyplexes, mosquito larval food, and agarose were used to prepare food pellets. The food pellets were fed to larvae once a day for five days. The mortality caused by PLK-EGCG-dsRNA nanoparticle feeding varied from 33.33 to 80.3%. The control larvae that fed on PLK-EGCG-dsEGFP exhibited 20% mortality. The PLK-EGCG-dsRNA polyplexes targeting IAP, SNF7 and SRC caused significant mortality when compared to the mortality caused by control PLK-EGCG-dsGFP polyplexes (FIG. 13a). Further, the gene knockdown by PLK-EGCG-dsIAP polyplexes was confirmed using reverse-transcriptase quantitative real-time PCR (RT-qPCR). The larvae were fed on polyplex containing food pellets once a day for a total of four days. The mRNA levels of the target genes were determined on the fifth day after the initiation of feeding. Oral administration of polyplexes reduced the target gene mRNA levels by 72.3% (FIG. 13b).

The qRT-PCR results clearly showed that feeding of mosquito larvae with PLK-EGCG-dsIAP effectively triggered RNAi.

Figure 14C:
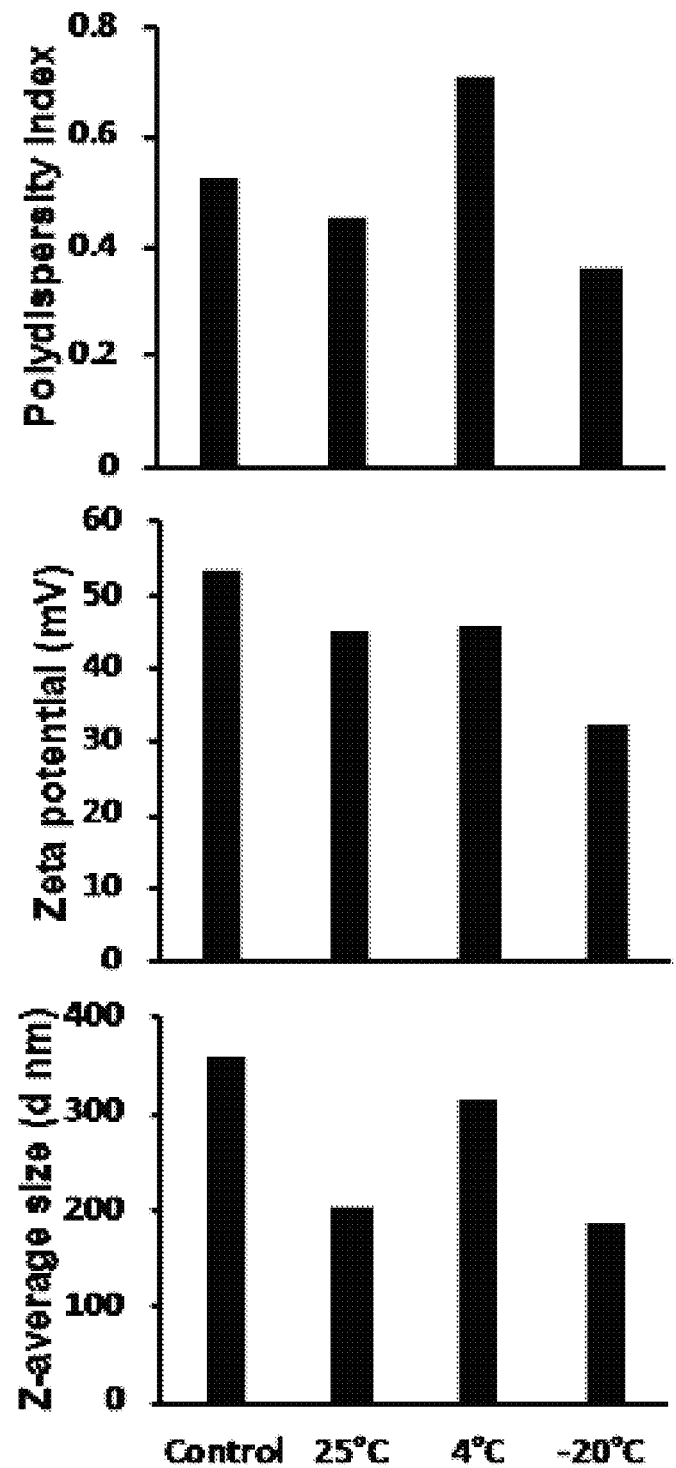
FIG. 14C shows polyplexes stability assay. The polyplexes average size, zeta potential, and polydispersion index.
Figure 15A:
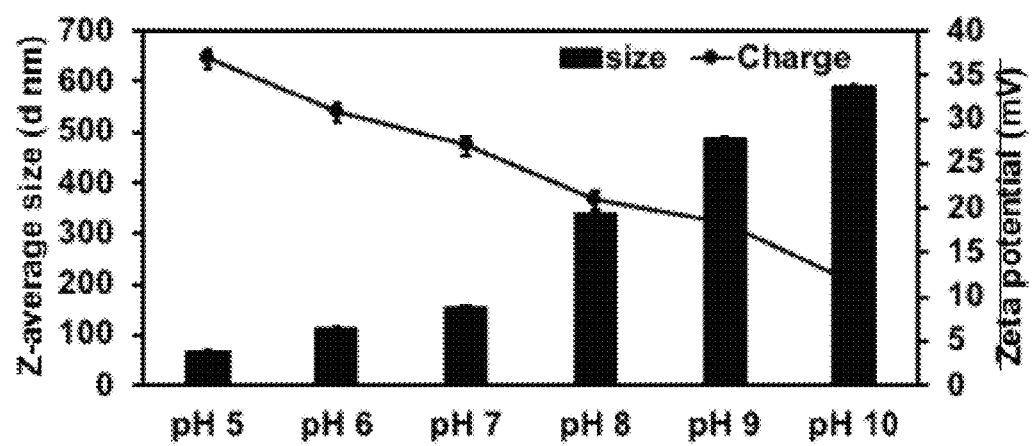
FIG. 15A shows DLS analysis of PLK-EGCG-dsRNA polyplexes. Polyplexes size and the charge were checked at different pH range (5-10).
Figure 15B:
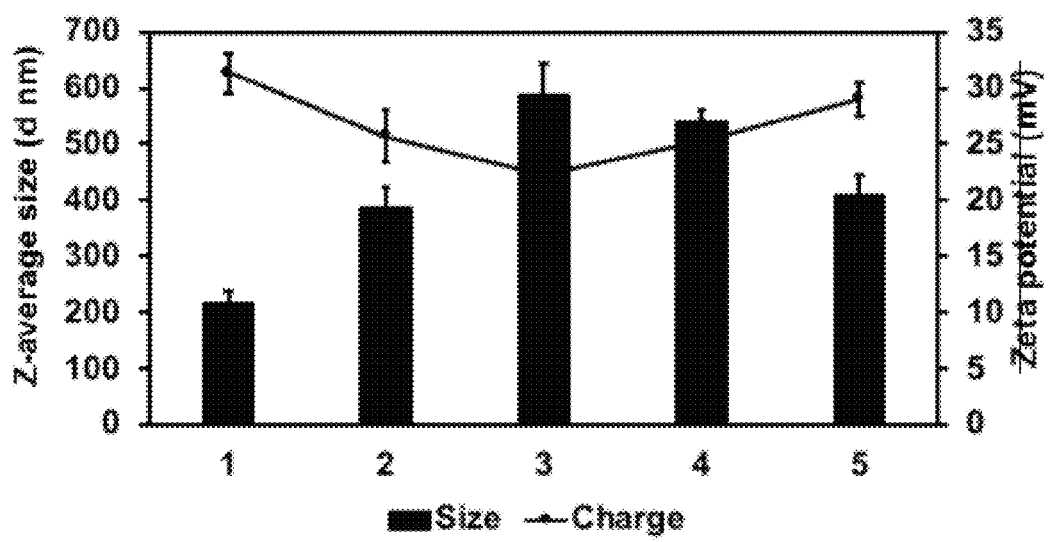
FIG. 15B shows DLS analysis of PLK-EGCG-dsRNA polyplexes. Polyplexes were incubated 1-media; 2-serum media; 3-conditional media; 4-midgut juice and 5-mosquito containing water, after 24 hr, particles size, and zeta potential analyzed by DLS.

PLK-EGCG-dsRNA polyplexes were stored at different temperature (25° C., 4° C., and −20° C.) in deionized water up to 20 days. EGCG started to degrade in the 7$^{th}$ day (25° C.) and 13$^{th}$ day (4° C.) and more stable up to 20$^{th}$ day in (−20° C.) (FIG. 14). The average size, zeta potential and polydispersity index of these polyplexes did not change significantly during storage (FIG. 14). In addition, the polyplexes were tested for change in size and charge after exposing to different pH conditions. When pH increased, the size and charge of the polyplexes decreased (FIG. 15).

Figure 16A:
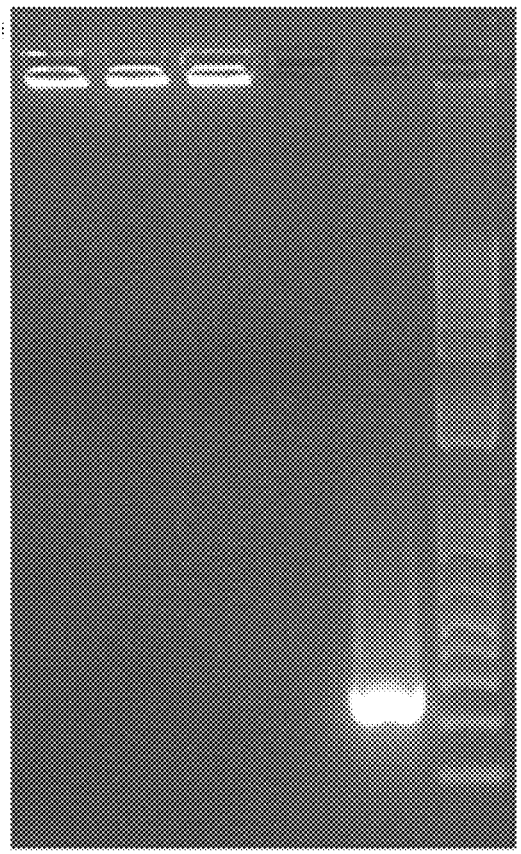
FIG. 16A shows Preparation and characterization of PS:Cf:dsRNA nanoparticles. Formation of nanoparticles ratio of (10:1:1) PS-Cf-dsRNA—gel retardation assay.
Figure 16B:
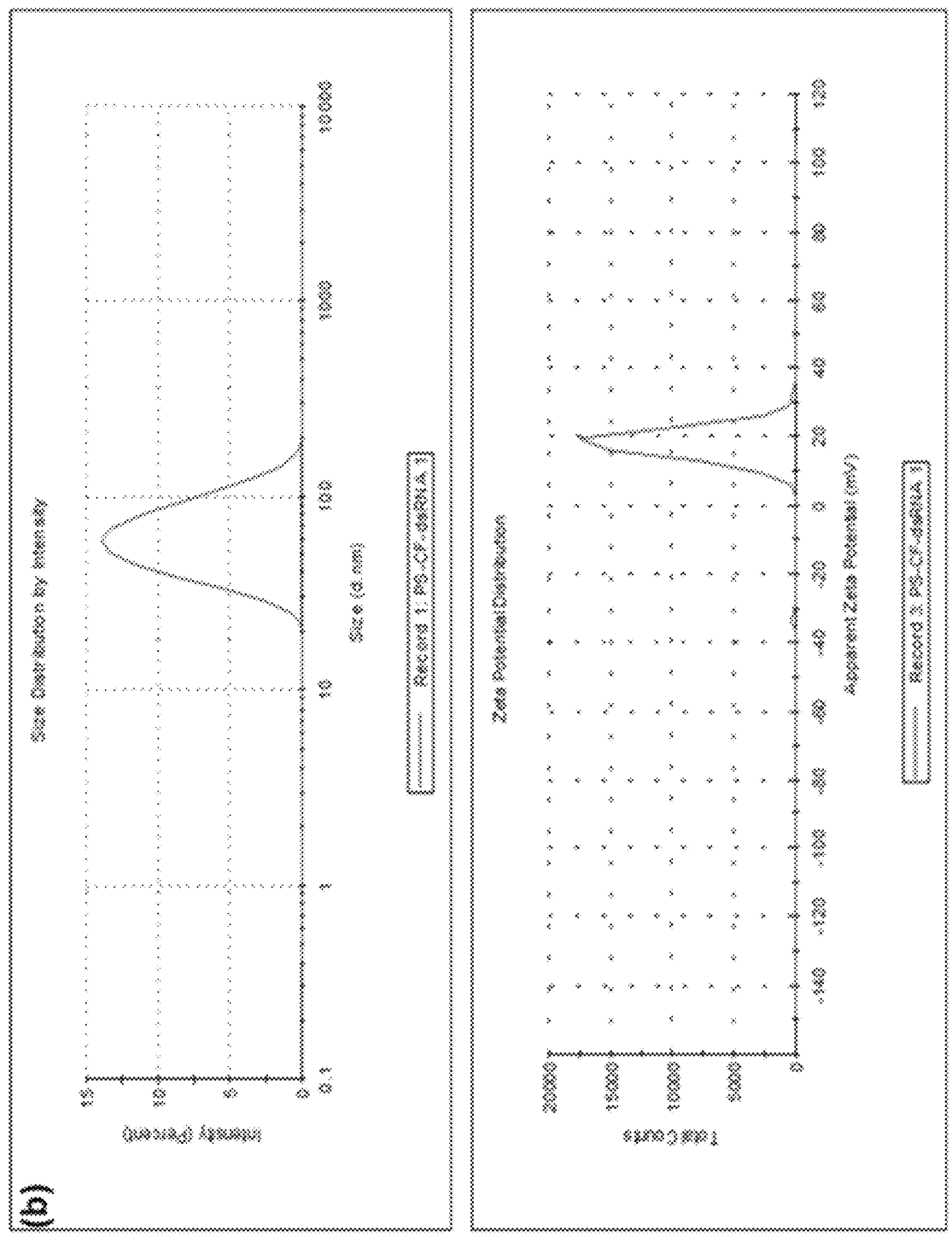
FIG. 16B shows Preparation and characterization of PS:Cf:dsRNA nanoparticles ratio of (10:1:1). DLS analysis of PS-Cf-dsRNA nanoparticles z-average size and zeta potential.
Figure 16C:
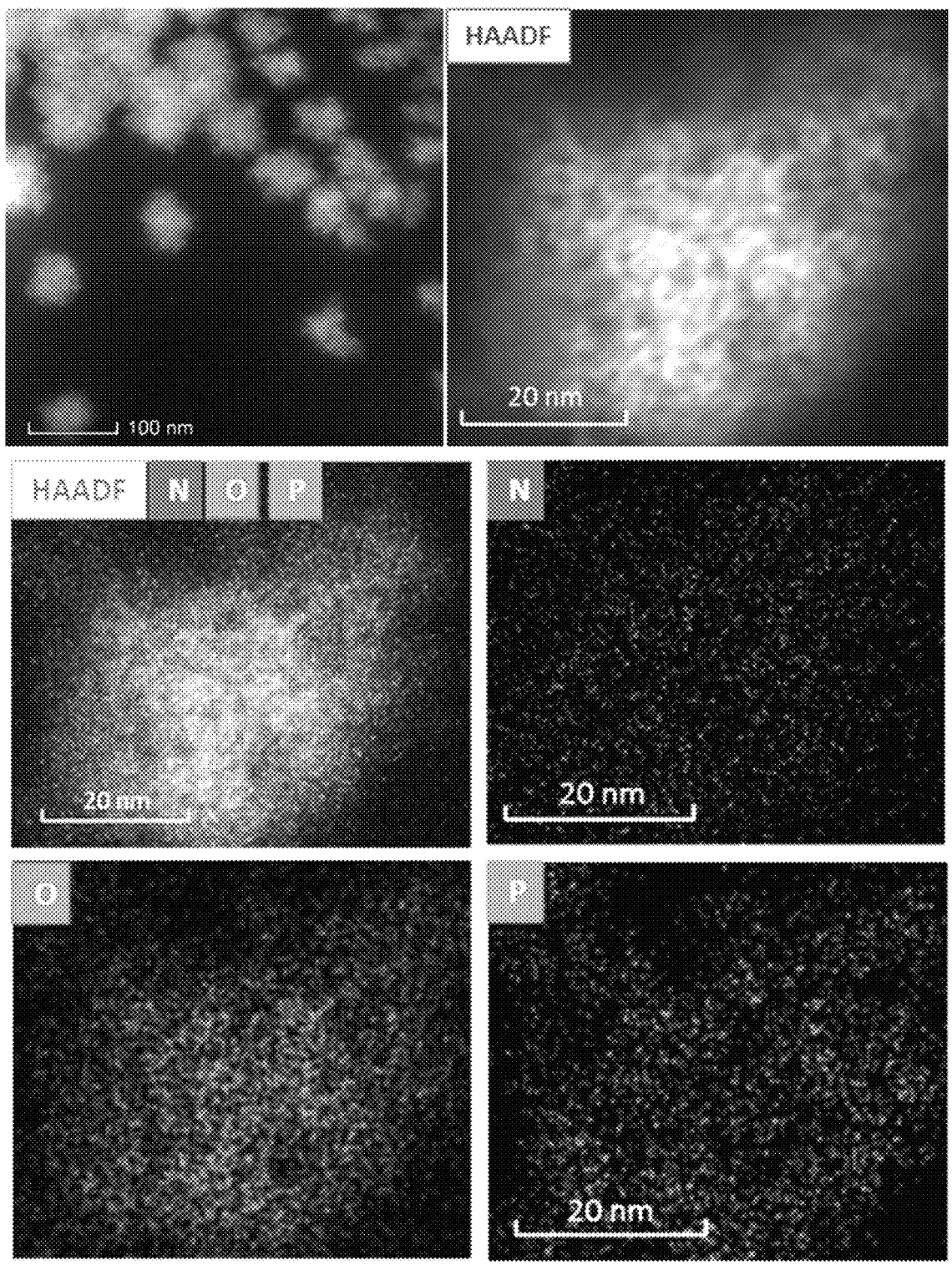
FIG. 16C shows Preparation and characterization of PS:Cf:dsRNA nanoparticles ratio of (10:1:1). Elemental analysis of polyplex.

The preparation and characterization of PS:Cf:dsRNA nanoparticles. Formation of nanoparticles ratio of (10:1:1) PS-Cf-dsRNA—gel retardation assay (FIG. 16A); DLS analysis of PS-Cf-dsRNA nanoparticles z-average size and zeta potential. (FIG. 16B). Elemental analysis of polyplex. (FIG. 16C).

Figure 17A:
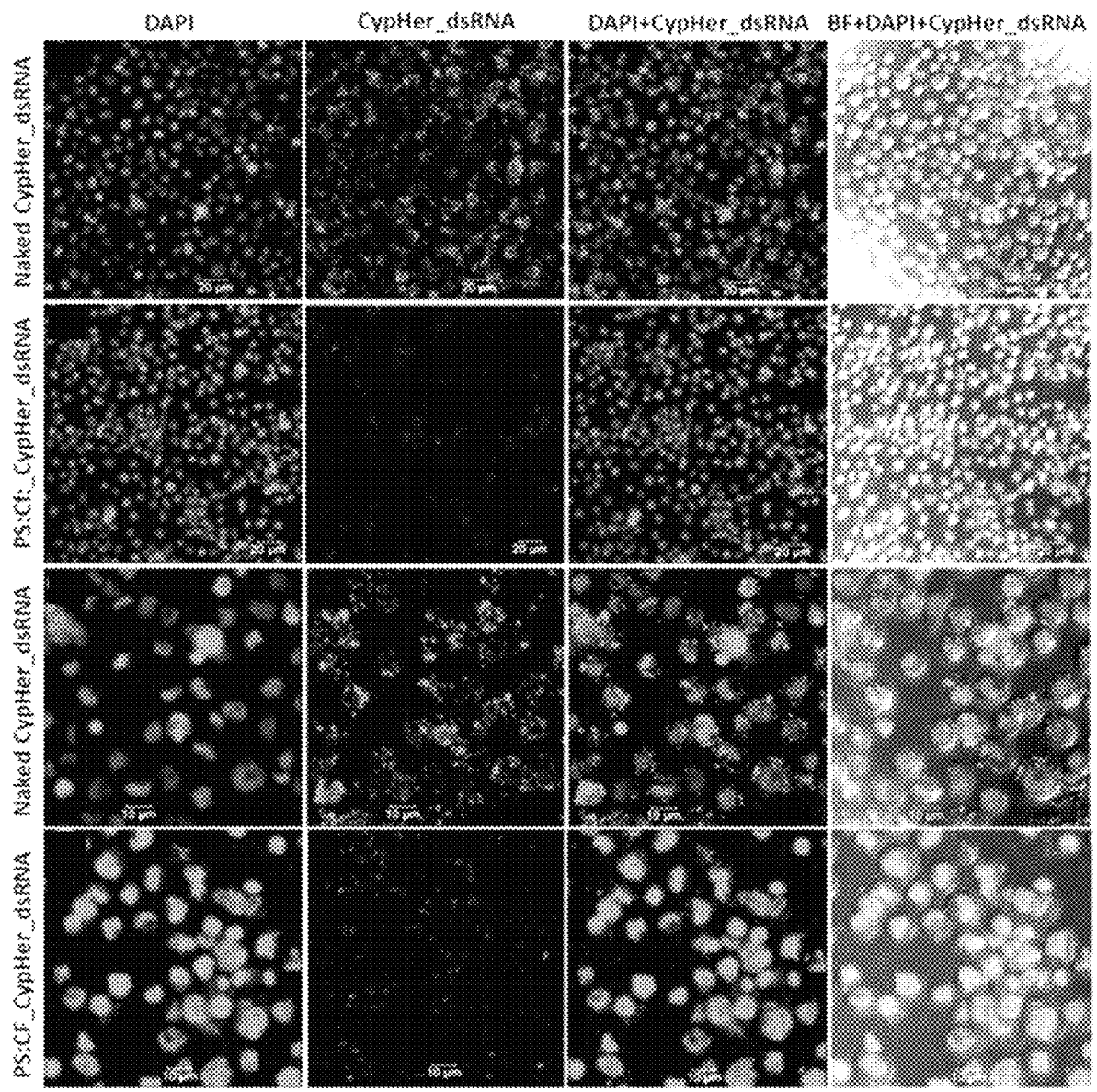
FIG. 17A shows CypHer-5E-labeled dsRNA conjugated to Protamine (PS) and celfectin (Cf) nanoparticles reduce the accumulation of dsRNA in the endosomes of Sf9 cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (top row, second row) and 10 µm (third row, bottom row).
Figure 17B:
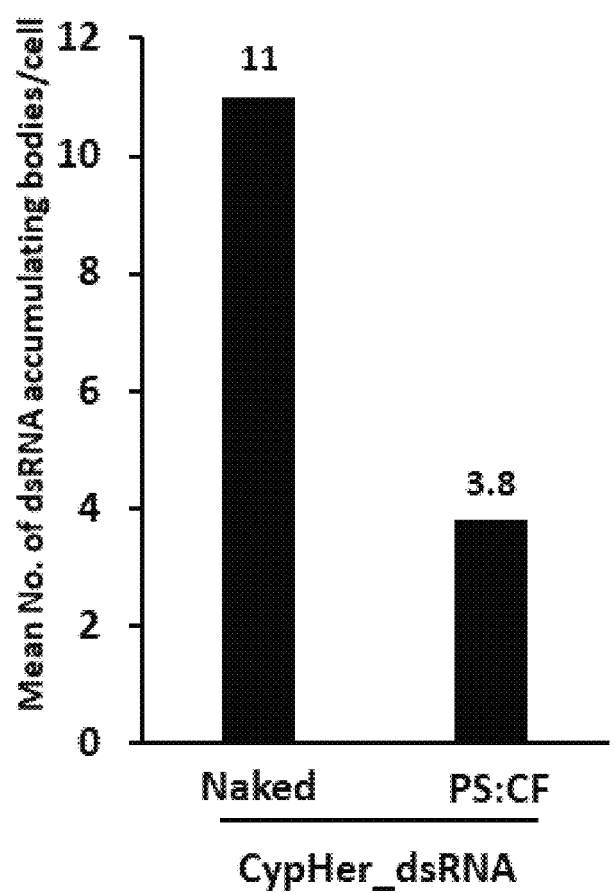
FIG. 17B shows dsRNA accumulating bodies were counted in 50 cells and plotted mean number of dsRNA accumulating per cell.

CypHer-5E-labeled dsRNA conjugated to Protamine (PS) and celfectin (CO nanoparticles reduce the accumulation of dsRNA in the endosomes of 519 cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (top row, second row) and 10 µm (third row, bottom row). (FIG. 17A). dsRNA accumulating bodies were counted in 50 cells and plotted mean number of dsRNA accumulating per cell. (FIG. 17B)

Figure 18:
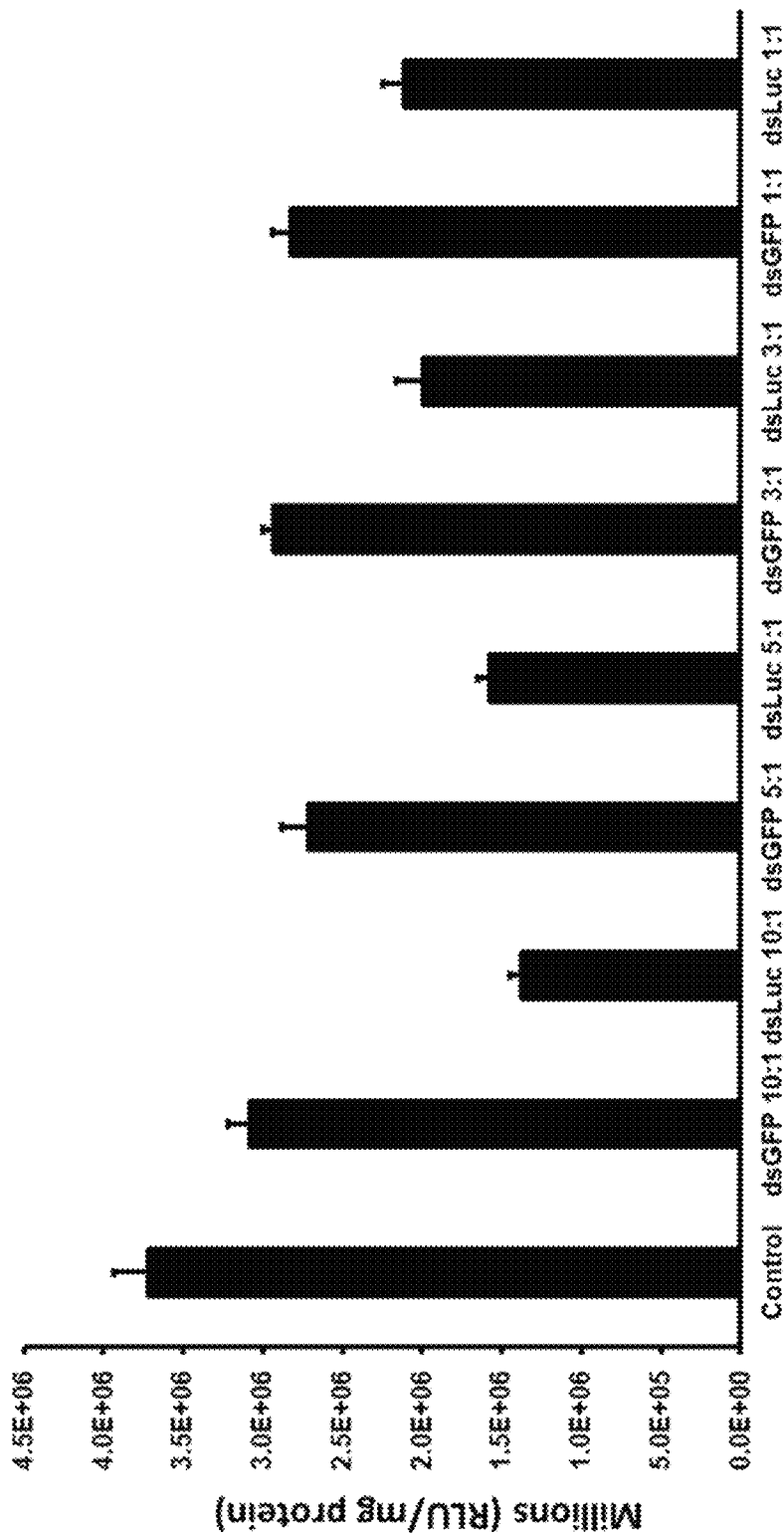
FIG. 18 shows Different ratio of PS-dsRNA nanoparticles testing the luciferase activity in Sf9 cells expressing the luciferase gene. The results showed that 45% reduced expression of the luciferase gene in the ratio of PLL-dsRNA (10:1); Asterisk show statistical difference (P<0.05).

Different ratio of PS-dsRNA nanoparticles testing the luciferase activity in Sf9 cells expressing the luciferase gene. The results showed that 45% reduced expression of the luciferase gene in the ratio of PLL-dsRNA (10:1); Asterisk show statistical difference (P<0.05). (FIG. 18)

Figure 19:
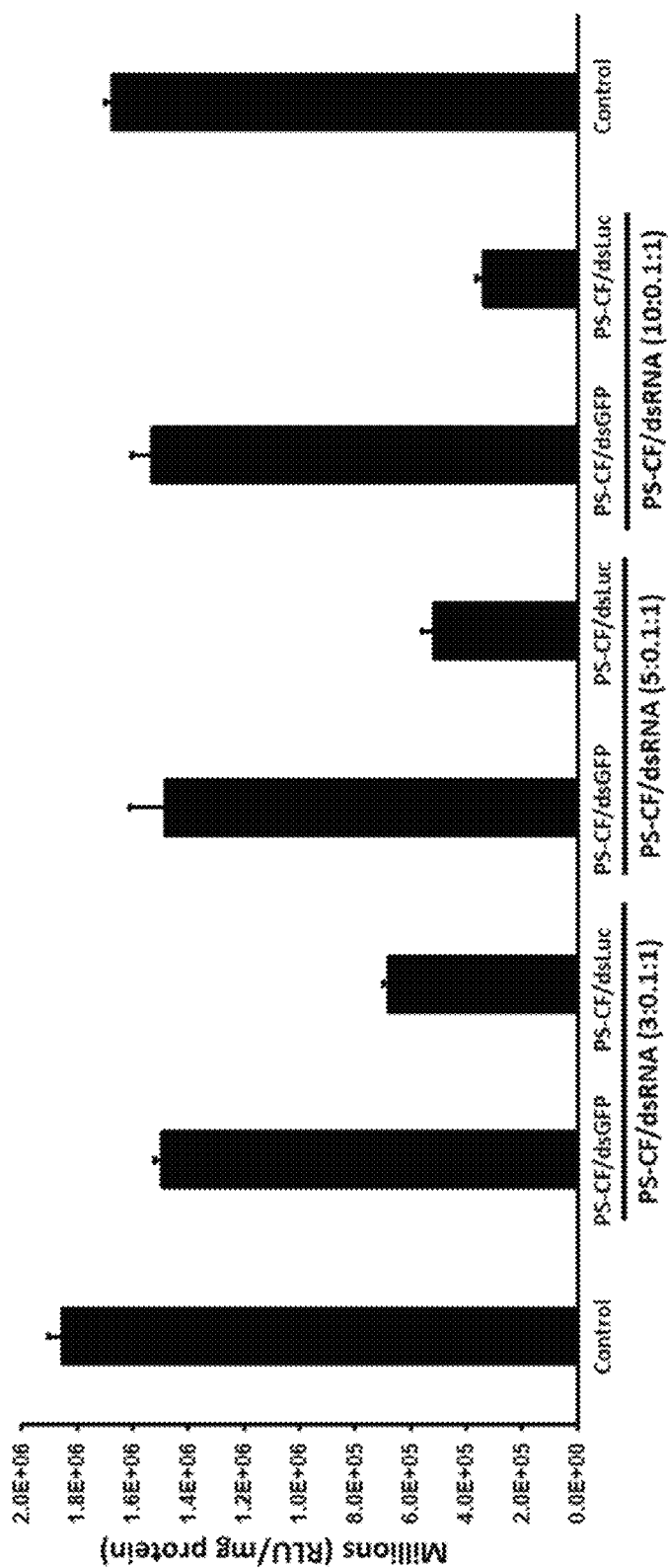
FIG. 19 shows Different ratio of PS:Cf:dsRNA nanoparticles testing the luciferase activity in Sf9 cells expressing the luciferase gene. The results showed that 78.4% reduced expression of the luciferase gene in the ratio of PS:Cf: dsRNA (10:0.1:1).

Different ratio of PS:Cf:dsRNA nanoparticles testing the luciferase activity in Sf9 cells expressing the luciferase gene. The results showed that 78.4% reduced expression of the luciferase gene in the ratio of PS:Cf:dsRNA (10:0.1:1). (FIG. 19)

Figure 20A:
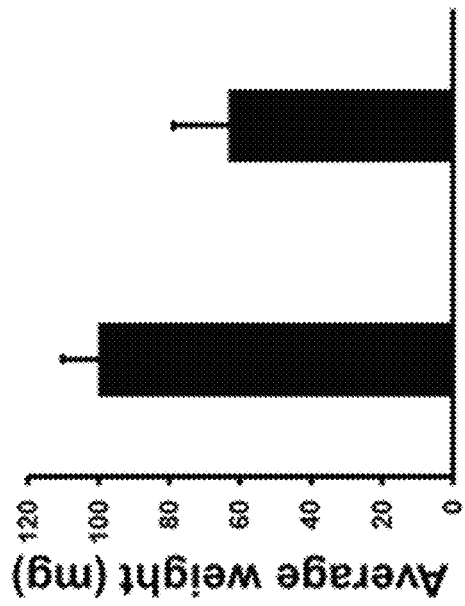
FIG. 20A shows Sucrose feeding droplet assay of PS/CF-dsRNA nanocomplexes. Nanocomplexes were mixed with 5% sucrose solution and food coloring dye and fed to newly hatched ALB (Anoplophora glabripennis) larvae. The growth was retarded and average weight was determined (mg)
Figure 20C:
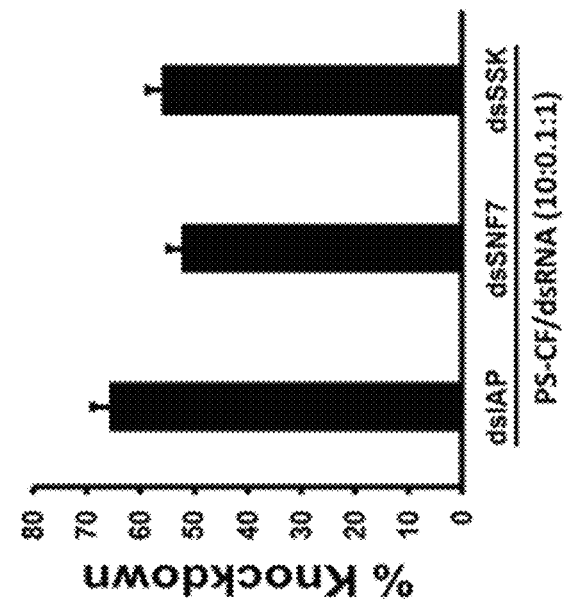
FIG. 20C shows Sucrose feeding droplet assay of PS/CF-dsRNA nanocomplexes. Nanocomplexes were mixed with 5% sucrose solution and food coloring dye and fed to newly hatched ALB larvae. gene knockdown.
Figure 20B:
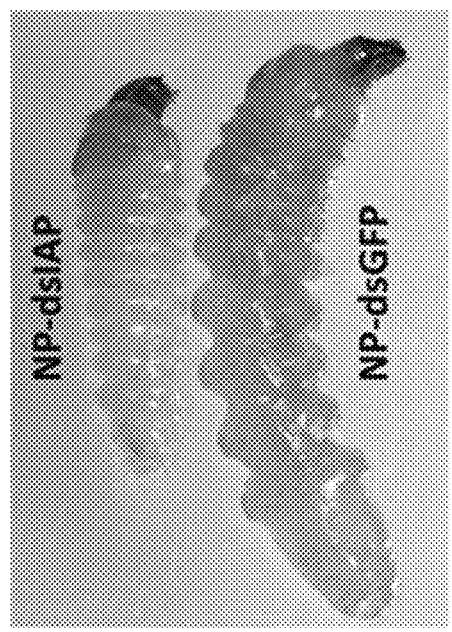
FIG. 20B shows Sucrose feeding droplet assay of PS/CF-dsRNA nanocomplexes. Nanocomplexes were mixed with 5% sucrose solution and food coloring dye and fed to newly hatched ALB larvae. The mortality was recorded

Sucrose feeding droplet assay of PS/CF-dsRNA nanocomplexes. Nanocomplexes were mixed with 5% sucrose solution and food coloring dye and fed to newly hatched ALB larvae. The growth was retarded and average weight was determined (mg) (FIG. 20A). Nanocomplexes were mixed with 5% sucrose solution and food coloring dye and fed to newly hatched ALB larvae. The mortality was recorded (FIG. 20B). Sucrose feeding droplet assay of PS/CF-dsRNA nanocomplexes. Nanocomplexes were mixed with 5% sucrose solution and food coloring dye and fed to newly hatched ALB larvae. gene knockdown. (FIG. 20C).

Figure 21:
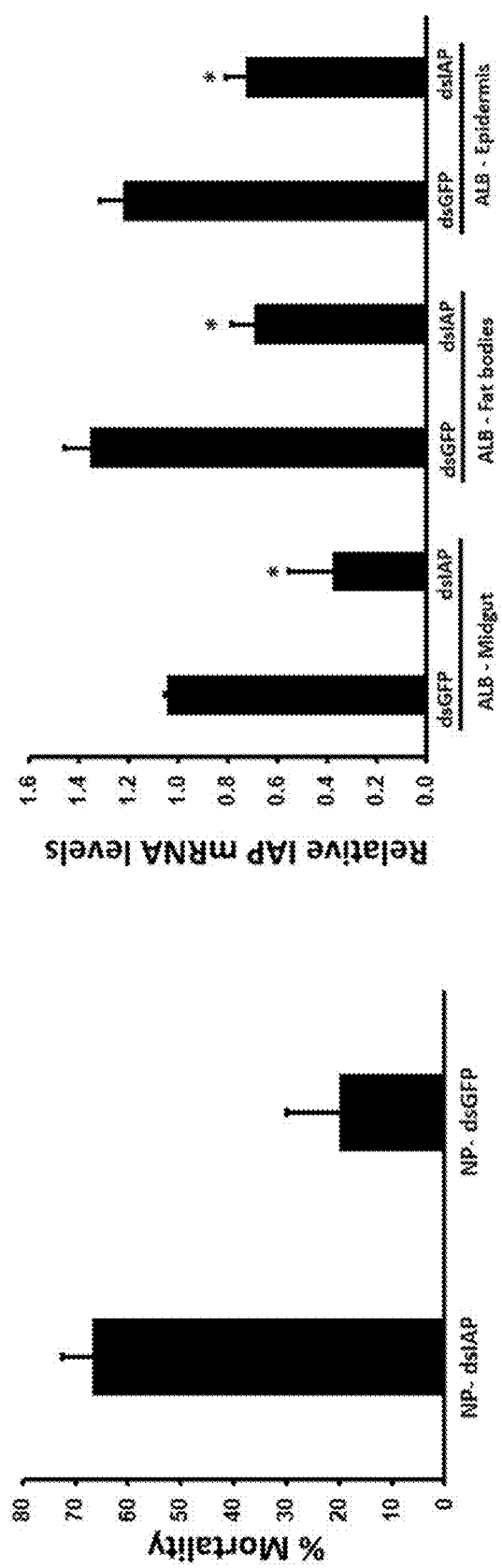
FIG. 21 shows PLL-EGCG-dsRNA nanoparticles induced RNAi in ALB larvae by feeding assay. Total 10 µg of dsGFP and dsIAP nanoparticles mixed with diet and fed to ALB larvae for three days (10 µg/day). The mortality was recorded up to 20 days post feeding. The knockdown of IAP mRNA levels were quantified on 5th day post feeding. Mean±SE (n=3) are shown. Asterisk show statistical difference (P<0.05). The 64.3, 48.9 and 40.5% knockdown of IAP gene expression were observed in the ALB larvae fed on dsIAP nanoparticles.

PLL-EGCG-dsRNA nanoparticles induced RNAi in ALB larvae by feeding assay. Total 10 µg of dsGFP and dsIAP nanoparticles mixed with diet and fed to ALB larvae for three days (10 µg/day). The mortality was recorded up to 20 days post feeding. The knockdown of IAP mRNA levels were quantified on 5th day post feeding. Mean±SE (n=3) are shown. Asterisk show statistical difference (P<0.05). The 64.3, 48.9 and 40.5% knockdown of IAP gene expression were observed in the ALB larvae fed on dsIAP nanoparticles. (FIG. 21).

Figure 22:
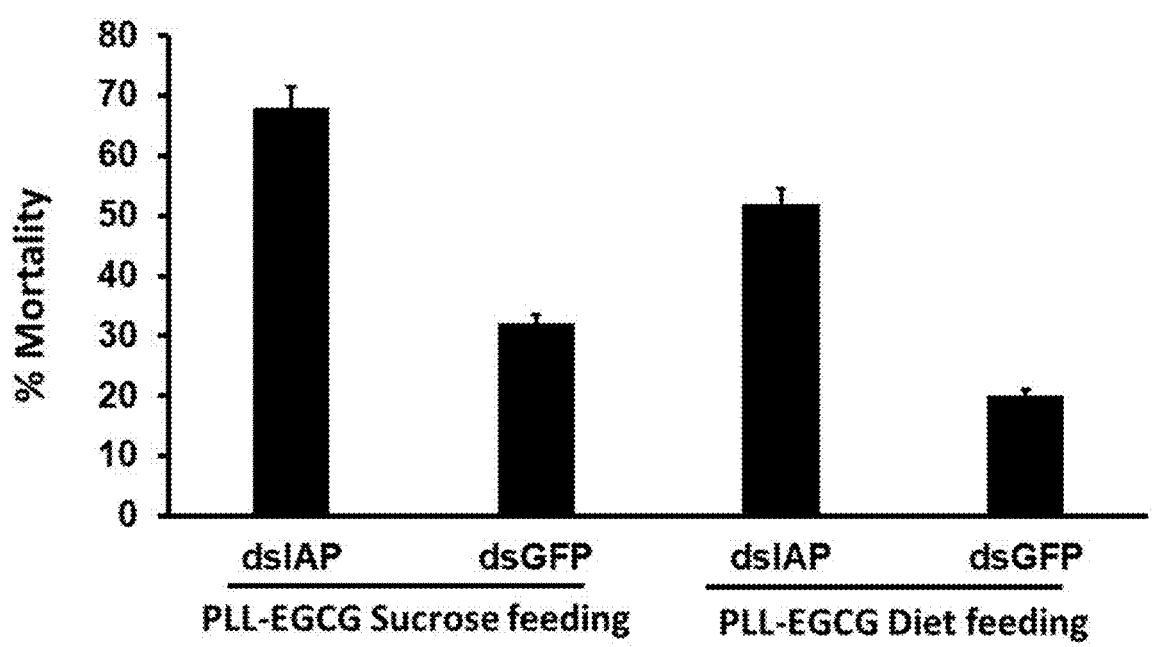
FIG. 22 shows PLL-EGCG-dsRNA nanoparticles induced RNAi in spodoptera neonates by feeding assay. Total 50 µg of dsGFP and dsIAP nanoparticles mixed with 5% sucrose solution and diet were fed neonate Spodoptera frugiperda. The mortality rate was recorded up to 10 days of post feeding.

PLL-EGCG-dsRNA nanoparticles induced RNAi in spodoptera neonates by feeding assay. Total 50 µg of dsGFP and dsIAP nanoparticles mixed with 5% sucrose solution and diet were fed neonate Spodoptera frugiperda. The mortality rate was recorded up to 10 days of post feeding. (FIG. 22)

Figure 23:
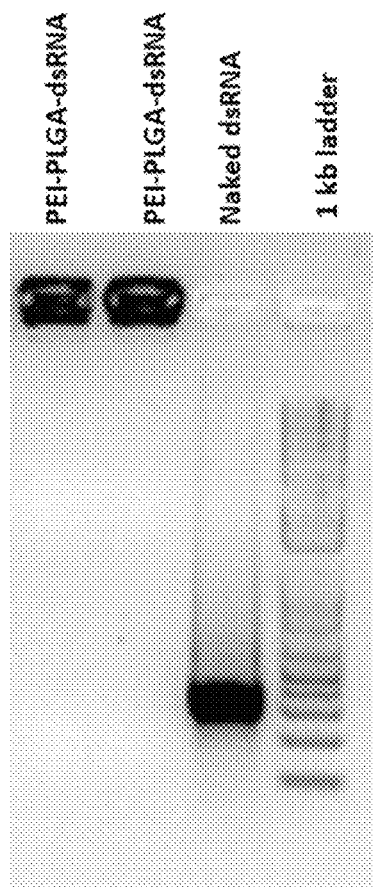
FIG. 23 shows Preparation and characterization of PLL-dsRNA nanoparticles. a) Formation of nanoparticles ratio of (3:1:1) PEI-PLGA-dsRNA—gel retardation assay; b) DLS analysis of PEI-PLGA-dsRNA nanoparticles z-average size and zeta potential.
Figure 23:
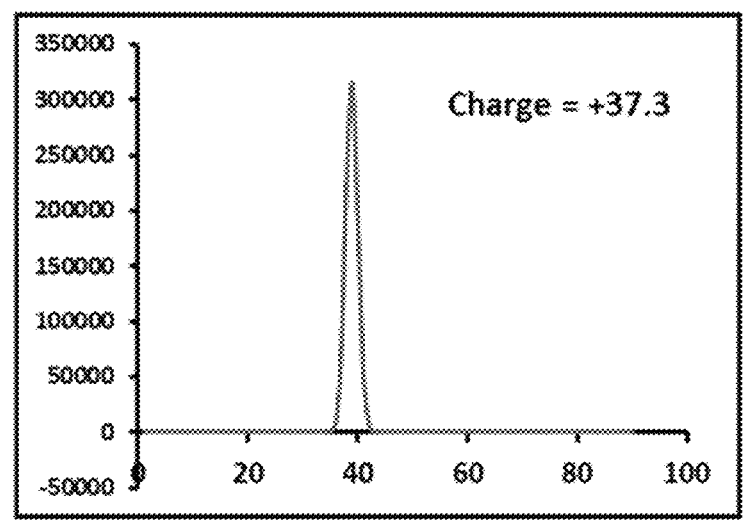
Figure 23:
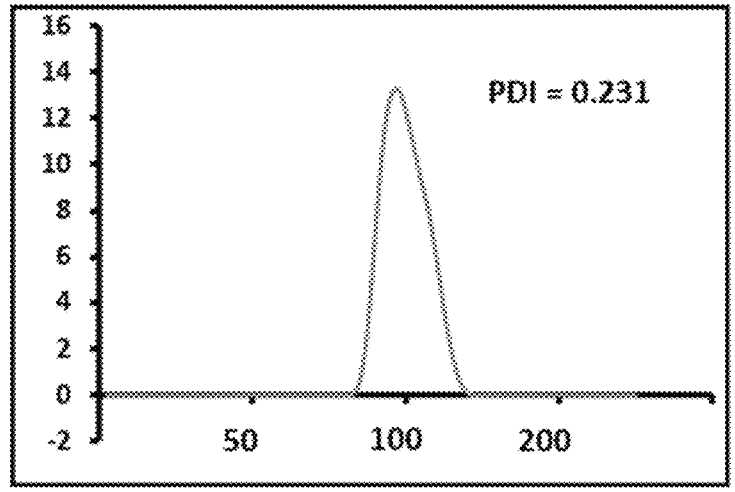

Preparation and characterization of PLL-dsRNA nanoparticles. a) Formation of nanoparticles ratio of (3:1:1) PEI-PLGA-dsRNA—gel retardation assay; b) DLS analysis of PEI-PLGA-dsRNA nanoparticles z-average size and zeta potential. (FIG. 23).

Figure 24:
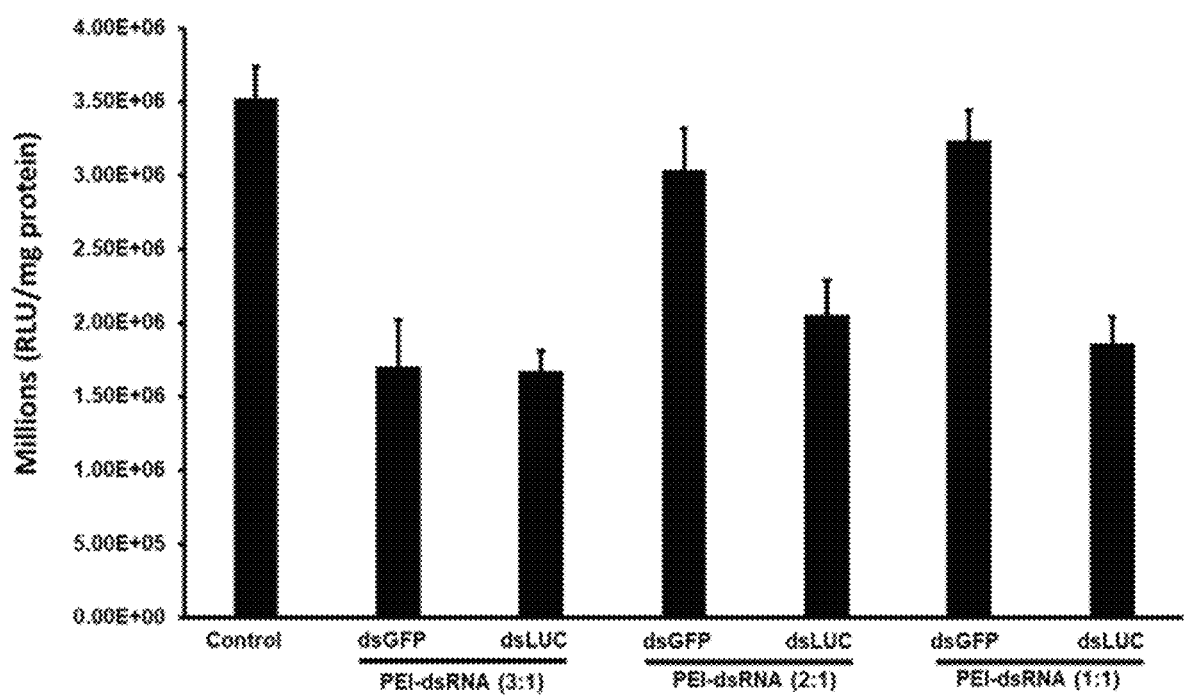
FIG. 24 shows Different ratio of PEI-dsRNA nanoparticles testing the luciferase activity in Sf9 cells expressing the luciferase gene. The results showed that 48% reduced expression of the luciferase gene in the ratio of PLL-dsRNA (5:1).

Different ratio of PEI-dsRNA nanoparticles testing the luciferase activity in Sf9 cells expressing the luciferase gene. The results showed that 48% reduced expression of the luciferase gene in the ratio of PLL-dsRNA (5:1). (FIG. 24).

Figure 25:
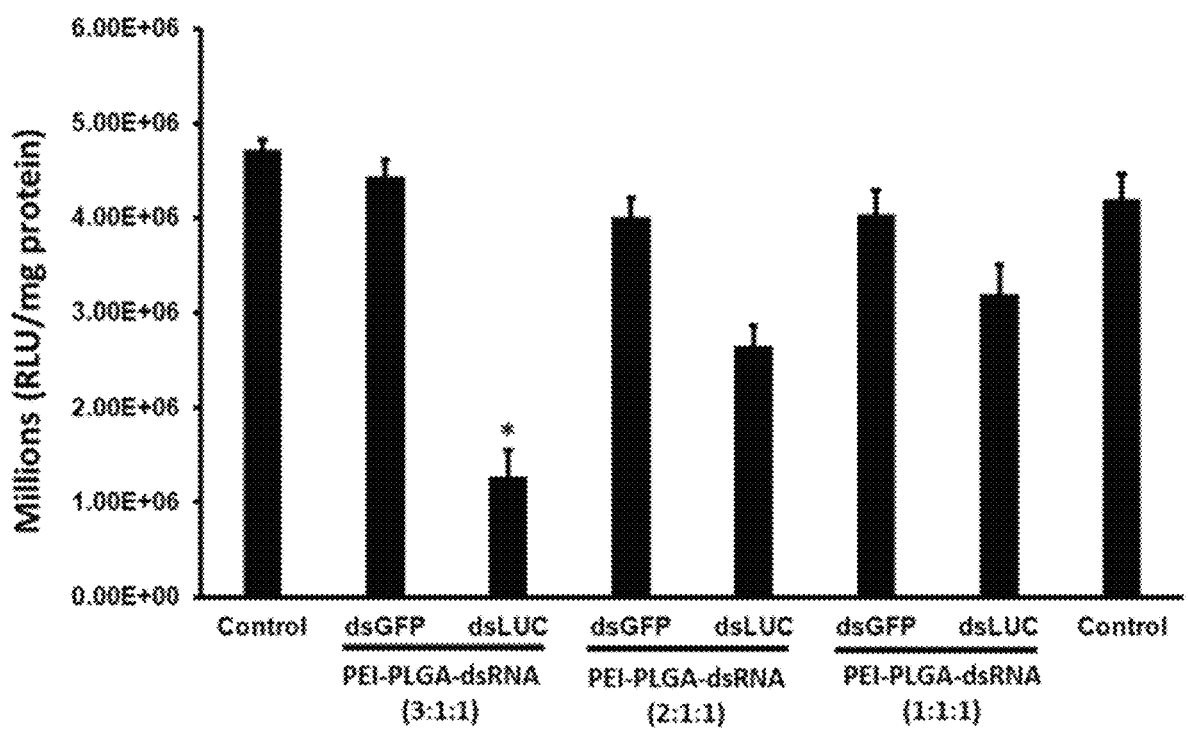
FIG. 25 shows Different ratio of PEI-PLGA-dsRNA nanoparticles testing the luciferase activity in Sf9 cells expressing the luciferase gene. The results showed that 72% reduced expression of the luciferase gene in the ratio of PEI-PLGA-dsRNA (3:1:1).

Different ratio of PEI-PLGA-dsRNA nanoparticles testing the luciferase activity in Sf9 cells expressing the luciferase gene. The results showed that 72% reduced expression of the luciferase gene in the ratio of PEI-PLGA-dsRNA (3:1:1). (FIG. 25).

Figure 26:
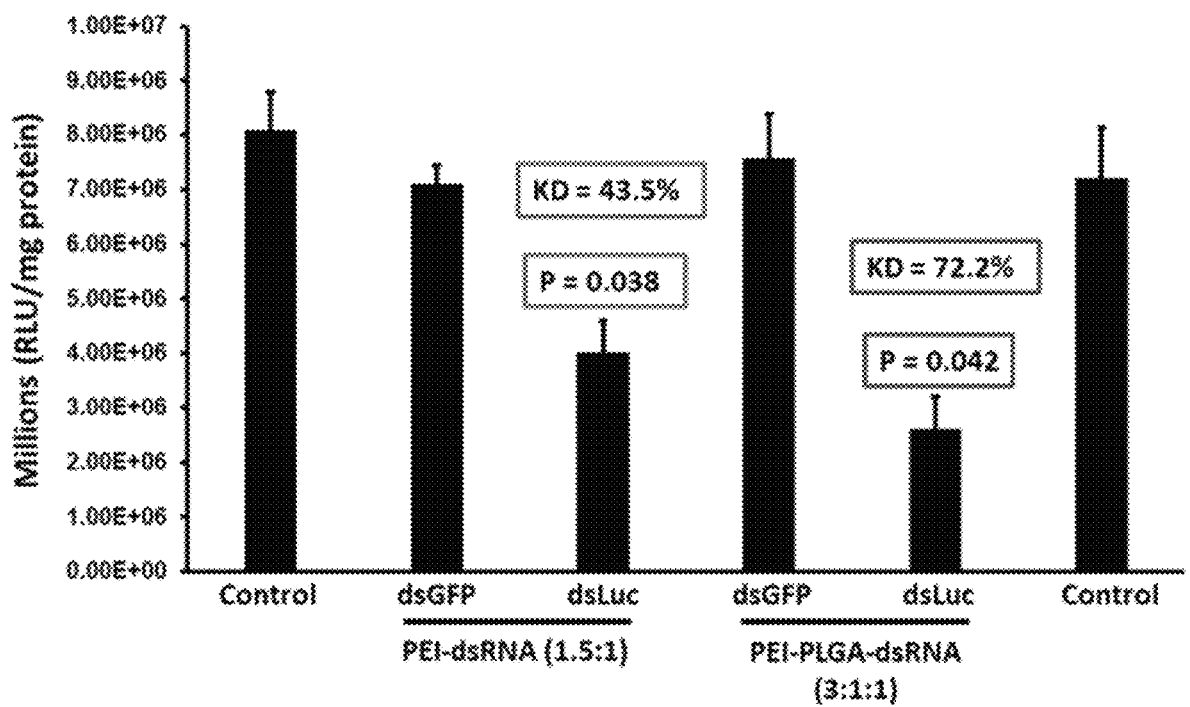
FIG. 26 shows PEI-PLGA-dsRNA nanoparticles testing the luciferase activity in Sf9 cells expressing the luciferase gene. The results showed that 72.2% reduced expression of the luciferase gene in the ratio of PEI-PLGA-dsRNA (3:1:1); Asterisk show statistical difference (P<0.05).

PEI-PLGA-dsRNA nanoparticles testing the luciferase activity in Sf9 cells expressing the luciferase gene. The results showed that 72.2% reduced expression of the luciferase gene in the ratio of PEI-PLGA-dsRNA (3:1:1); Asterisk show statistical difference (P<0.05). (FIG. 26).

Figure 27:
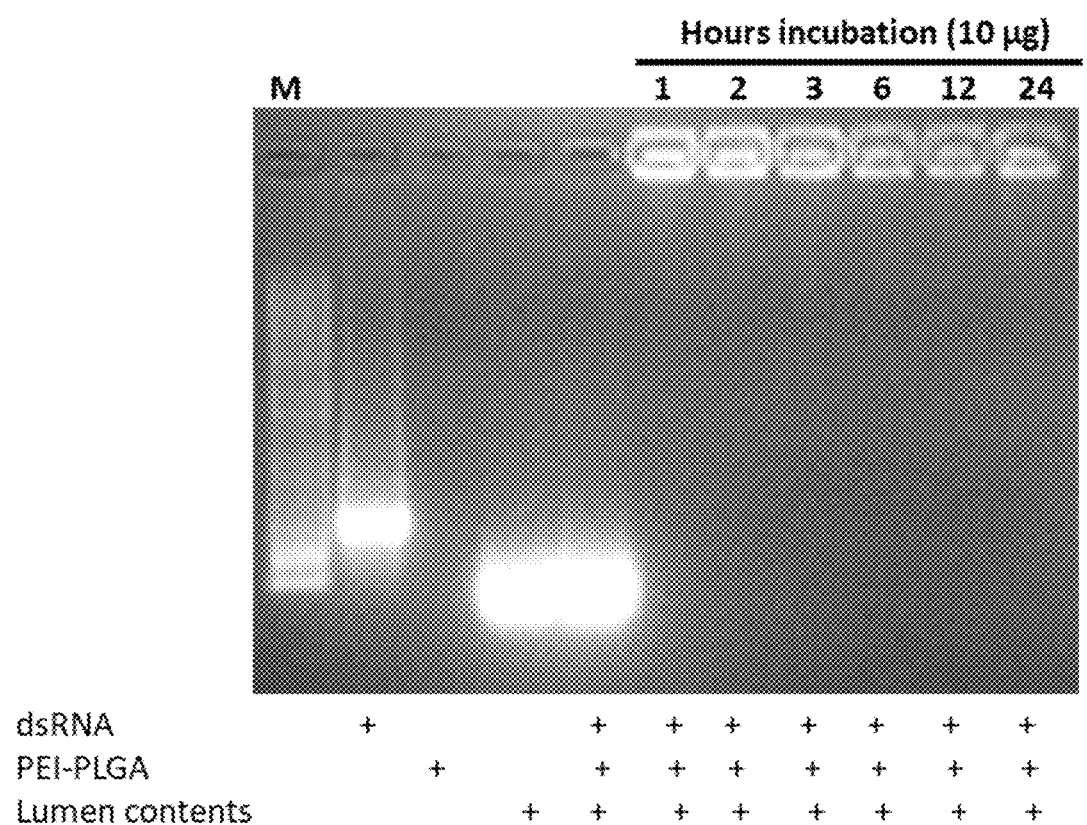
FIG. 27 shows Stability of dsRNA in the midgut lumen contents of spodoptera larvae. One microgram of PEI-PLGA-dsGFP was exposed to 10 µg of midgut lumen contents for 1, 2, 3, 6, 12 and 24 hrs. After exposure, the sample mixtures were collected and analyzed in 1% agarose gel electrophoresis.

Stability of dsRNA in the midgut lumen contents of Spodoptera larvae. One microgram of PEI-PLGA-dsGFP was exposed to 10 µg of midgut lumen contents for 1, 2, 3, 6, 12 and 24 hrs. After exposure, the sample mixtures were collected and analyzed in 1% agarose gel electrophoresis. (FIG. 27).

Figure 28:
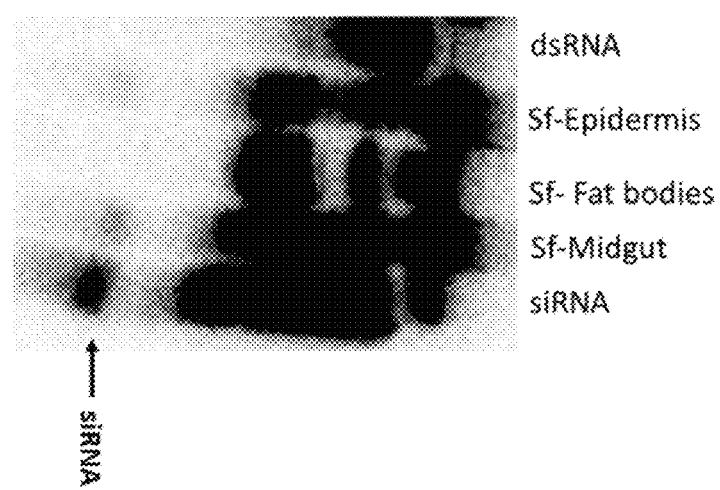
FIG. 28 shows Processing of dsRNA delivered to *Spodoptera* larvae by sucrose feeding assay. *Spodoptera* larvae were fed on 32P labeled dsRNA containing PEI-PLGA-dsRNA nanoparticles. On the fifth day after feeding, the total RNA was isolated and resolved on 8 M urea 16% polyacrylamide gels. The gels were dried and analyzed using phosphorImager. Arrow points to siRNA.

Processing of dsRNA delivered to Spodoptera larvae by sucrose feeding assay. Spodoptera larvae were fed on 32P labeled dsRNA containing PEI-PLGA-dsRNA nanoparticles. On the fifth day after feeding, the total RNA was isolated and resolved on 8 M urea 16% polyacrylamide gels. The gels were dried and analyzed using phosphorImager. Arrow points to siRNA. (FIG. 28).

Figure 29:
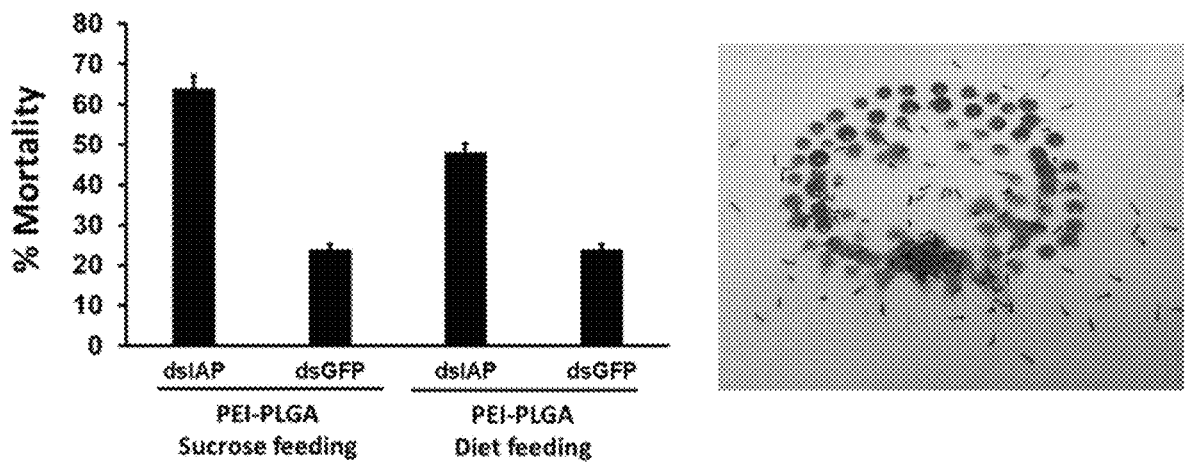
FIG. 29 shows Mortality induced by orally delivered dsRNA in *Spodoptera* larvae. PEI-PLGA-dsRNA nanoparticles was mixed with 5% sucrose solution and diet was fed to newly hatched *Spodoptera* larvae. one micrograms of nanoparticles were fed to the neonates for sucrose solution and two micrograms of nanoparticles incorporate diet over. Mortality was scored on 10th-day post-feeding. Mean±SE (n=3) are shown.

Mortality induced by orally delivered dsRNA in Spodoptera larvae. PEI-PLGA-dsRNA nanoparticles was mixed with 5% sucrose solution and diet was fed to newly hatched Spodoptera larvae. one micrograms of nanoparticles were fed to the neonates for sucrose solution and two micrograms of nanoparticles incorporate diet over. Mortality was scored on 10th-day post-feeding. Mean±SE (n=3) are shown. (FIG. 29).

Figure 30:
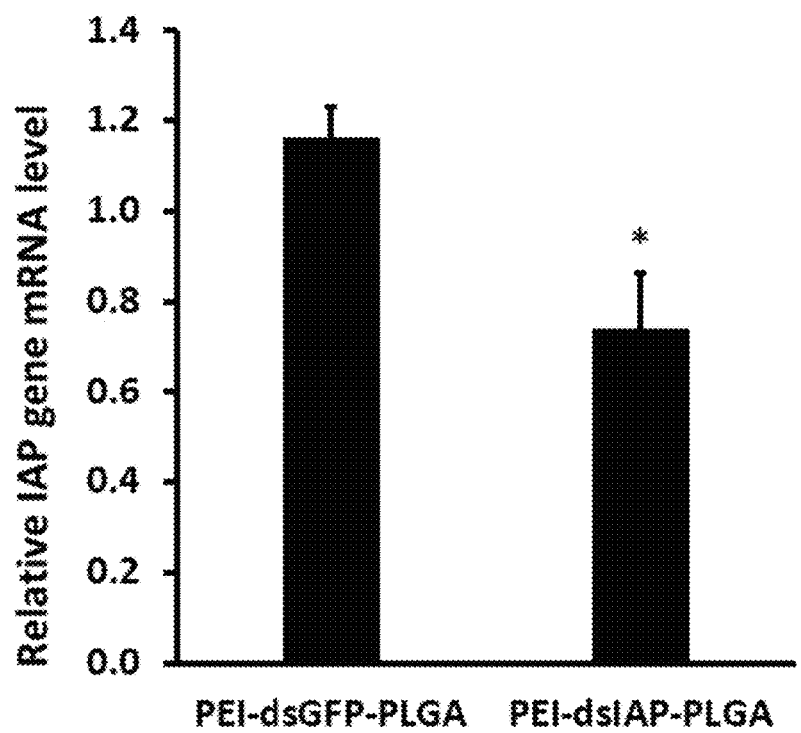
FIG. 30 shows Nanoparticles (PEI-PLGA-dsRNA) trigger efficient knockdown in spodoptera neonates feeding assay. Five microgram of nanoparticles fed to spodoptera larvae upto three days. After five days of post feeding, the total RNA was isolated, converted to cDNA and used to qRT-PCR to determine relative IAP mRNA levels. Date are presented as mean±SE (n=5). The asterisks above the bar indicate the significance of difference (T-TEST, $*P<0.05$).

Nanoparticles (PEI-PLGA-dsRNA) trigger efficient knockdown in spodoptera neonates feeding assay. Five microgram of nanoparticles fed to Spodoptera larvae upto three days. After five days of post feeding, the total RNA was isolated, converted to cDNA and used to qRT-PCR to determine relative IAP mRNA levels. Date are presented as mean±SE (n=5). The asterisks above the bar indicate the significance of difference (T-TEST, *P<0.05). (FIG. 30).

Figure 31:
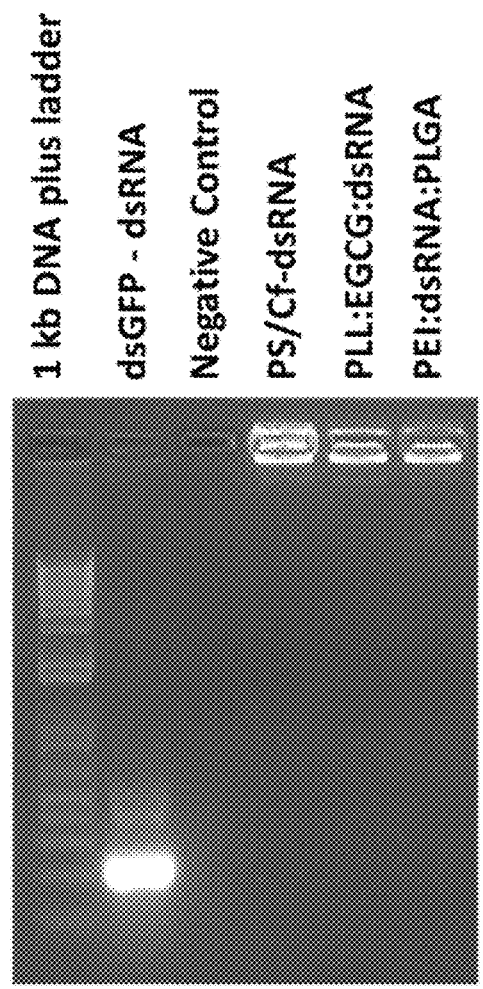
FIG. 31 shows PS:CF:dsRNA, PLL:EGCG:dsRNA and PEI:PLGA:dsRNA nanoparticles were prepared and characterized by gel retardation assay and DLS.

PS:CF:dsRNA, PLL:EGCG:dsRNA and PEI:PLGA:dsRNA nanoparticles were prepared and characterized by gel retardation assay and DLS. (FIG. 31).

Figure 32:
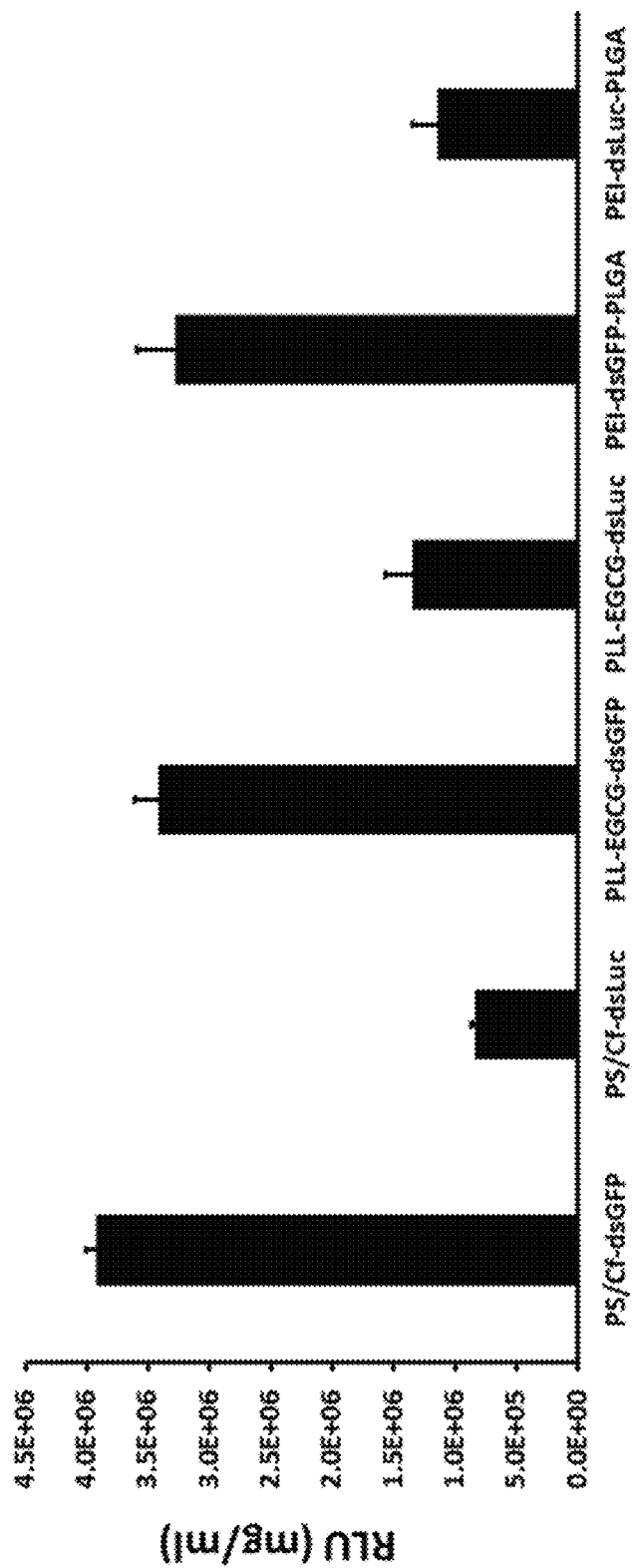
FIG. 32 shows PS:CF:dsRNA, PLL:EGCG:dsRNA and PEI:PLGA:dsRNA nanoparticles were in the luciferase activity in Sf9 cells expressing the luciferase gene.

PS:CF:dsRNA, PLL:EGCG:dsRNA and PEI:PLGA:dsRNA nanoparticles were in the luciferase activity in Sf9 cells expressing the luciferase gene. (FIG. 32).

Figure 33:
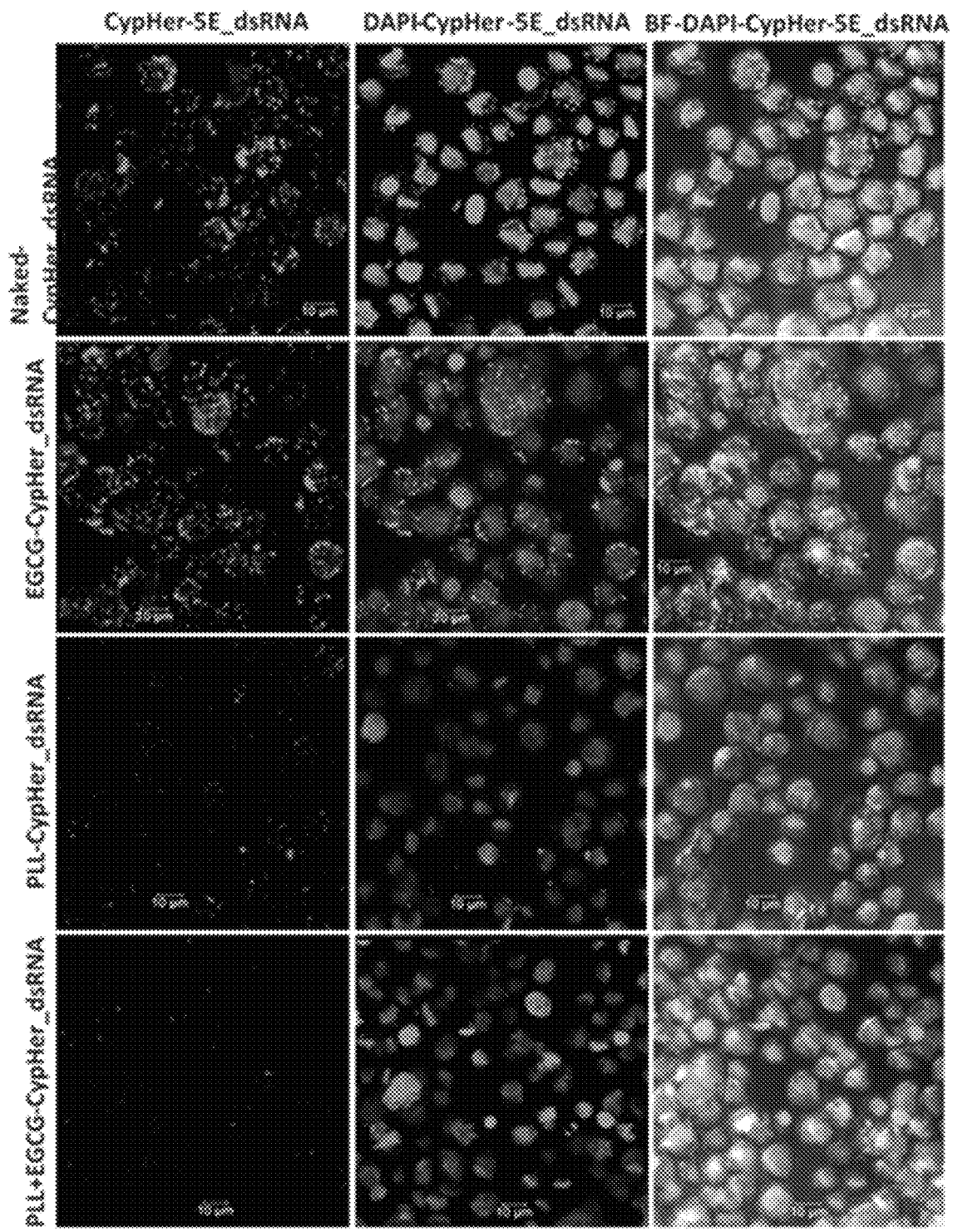
FIG. 33 shows CypHer-5E-labeled dsRNA conjugated to poly-L-lysine (PLL) with Epigallocatechin gallate (EGCG) nanoparticle reduce the accumulation of dsRNA in the acidic bodies of Sf9 cells. 120,000 cells/well were seeded in 8 well chamber slide and incubated 25 ng of naked, conjugated to EGCG, PLL and EGCG with PLL nanoparticle of CypHer-5E-labeled dsRNA mixed with Sf-900 II SFM medium for 4 h and washed the cells then fixed followed by stained using EverBrite mounting medium with DAPI and visualized the cells under Leica confocal microscope at 63× magnification (n=100; scale bar: 10 µm).

CypHer-5E-labeled dsRNA conjugated to poly-L-lysine (PLL) with Epigallocatechin gallate (EGCG) nanoparticle reduce the accumulation of dsRNA in the acidic bodies of 519 cells. 120,000 cells/well were seeded in 8 well chamber slide and incubated 25 ng of naked, conjugated to EGCG, PLL and EGCG with PLL nanoparticle of CypHer-5E-labeled dsRNA mixed with Sf-900 II SFM medium for 4 h and washed the cells then fixed followed by stained using EverBrite mounting medium with DAPI and visualized the cells under Leica confocal microscope at 63× magnification (n=100; scale bar: 10 µm). (FIG. 33).

Figure 34:
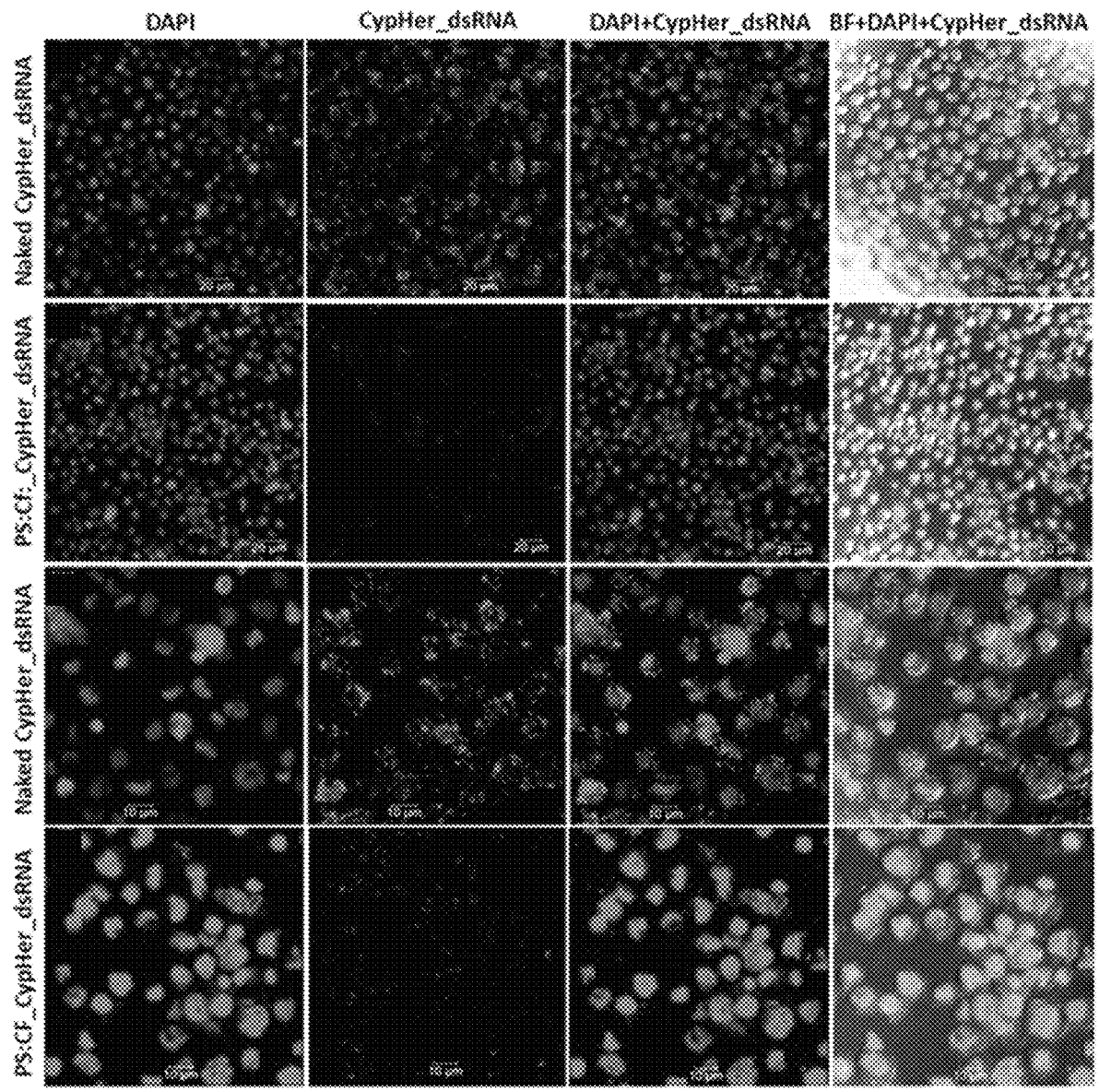
FIG. 34 shows CypHer-5E-labeled dsRNA conjugated to Protamine (PS) and celfectin (Cf) nanoparticles reduce the accumulation of dsRNA in the endosomes of Sf9 cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (top row, second row) and 10 µm (third row, bottom row).

CypHer-5E-labeled dsRNA conjugated to Protamine (PS) and celfectin (Cf) nanoparticles reduce the accumulation of dsRNA in the endosomes of 519 cells. 120,000 cells/well were seeded in 8 well chamber slide and incubated 25 ng of naked, conjugated to protamine nanoparticles of CypHer-5E-labeled dsRNA mixed with 100 μl Sf-900 II SFM medium for 4 hr and washed the cells then fixed followed by stained using EverBrite mounting medium with DAPI and visualized the cells under Leica confocal microscope at 63× magnification (scale bar: 20 μm (top row, second row) and 10 μm (third row, bottom row). (FIG. 34).

Figure 35:
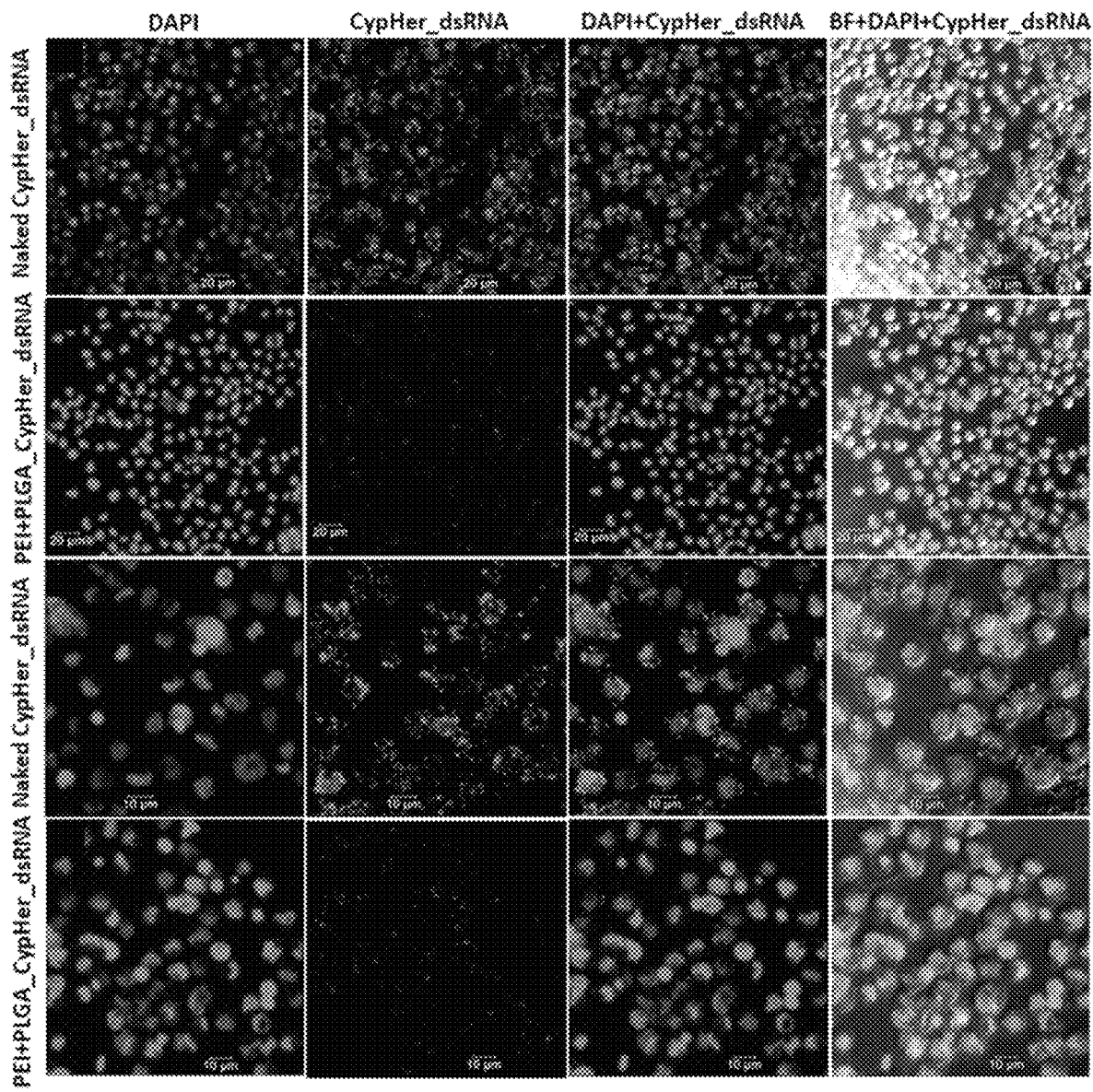
FIG. 35 shows CypHer-5E-labeled dsRNA conjugated to PLL:PGLA nanoparticles reduce the accumulation of dsRNA in the endosomes of 519 cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (top row, second row) and 10 µm (third row, bottom row).

CypHer-5E-labeled dsRNA conjugated to PLL:PGLA nanoparticles reduce the accumulation of dsRNA in the endosomes of Sf9 cells. 120,000 cells/well were seeded in 8 well chamber slide and incubated 25 ng of naked, conjugated to protamine nanoparticles of CypHer-5E-labeled dsRNA mixed with 100 μl Sf-900 II SFM medium for 4 hr and washed the cells then fixed followed by stained using EverBrite mounting medium with DAPI and visualized the cells under Leica confocal microscope at 63× magnification (scale bar: 20 μm (top row, second row) and 10 μm (third row, bottom row). (FIG. 35).

Figure 36:
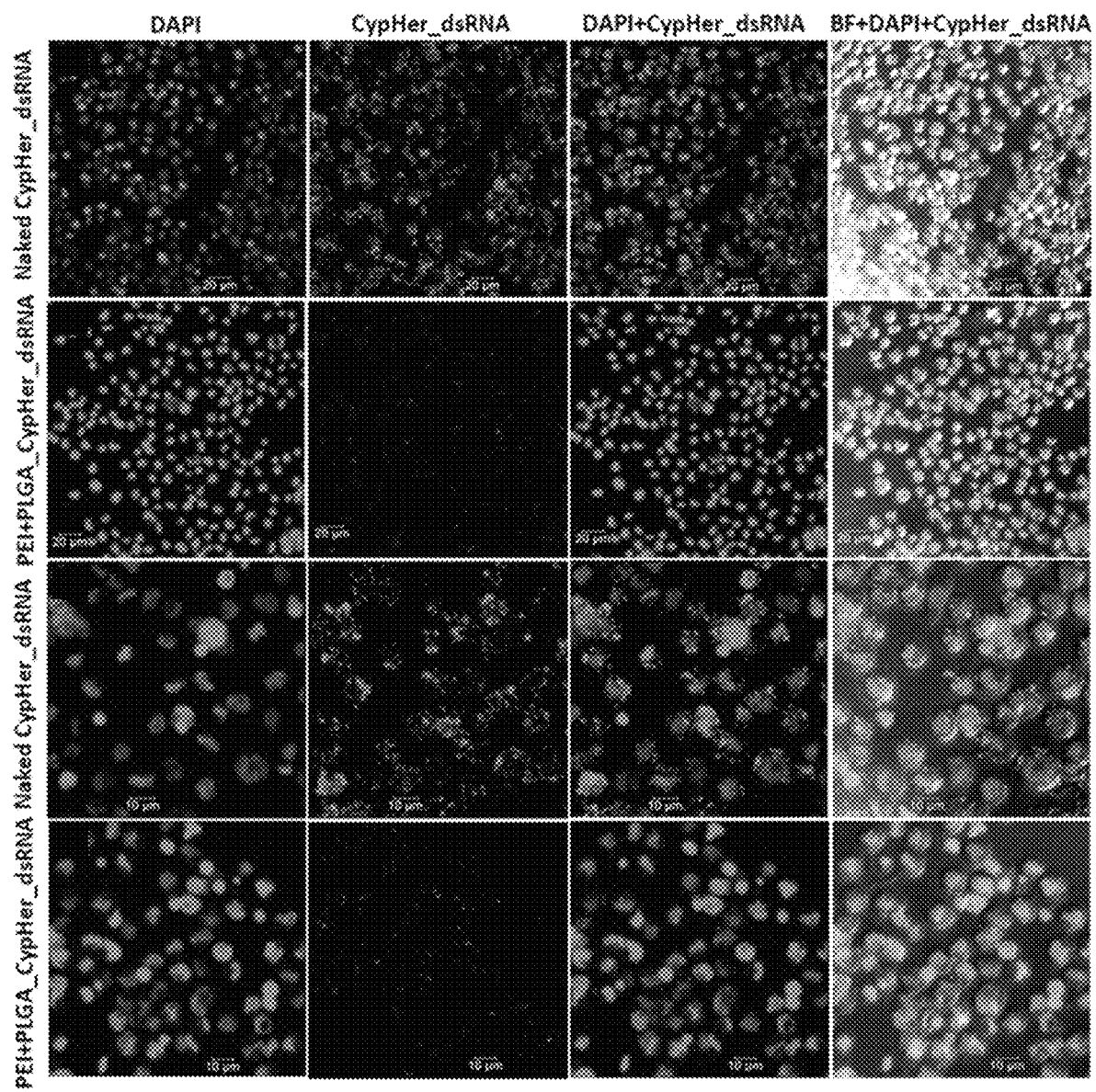
FIG. 36 shows CypHer-5E-labeled dsRNA conjugated to PLL:PGLA nanoparticles reduce the accumulation of dsRNA in the endosomes of SD cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (top row, second row) and 10 µm (third row, bottom row).

CypHer-5E-labeled dsRNA conjugated to PLL:PGLA nanoparticles reduce the accumulation of dsRNA in the endosomes of Sf9 cells. 120,000 cells/well were seeded in 8 well chamber slide and incubated 25 ng of naked, conjugated to protamine nanoparticles of CypHer-5E-labeled dsRNA mixed with 100 μl Sf-900 II SFM medium for 4 hr and washed the cells then fixed followed by stained using EverBrite mounting medium with DAPI and visualized the cells under Leica confocal microscope at 63× magnification (scale bar: 20 μm (top row, second row) and 10 μm (third row, bottom row). (FIG. 36).

Figure 37:
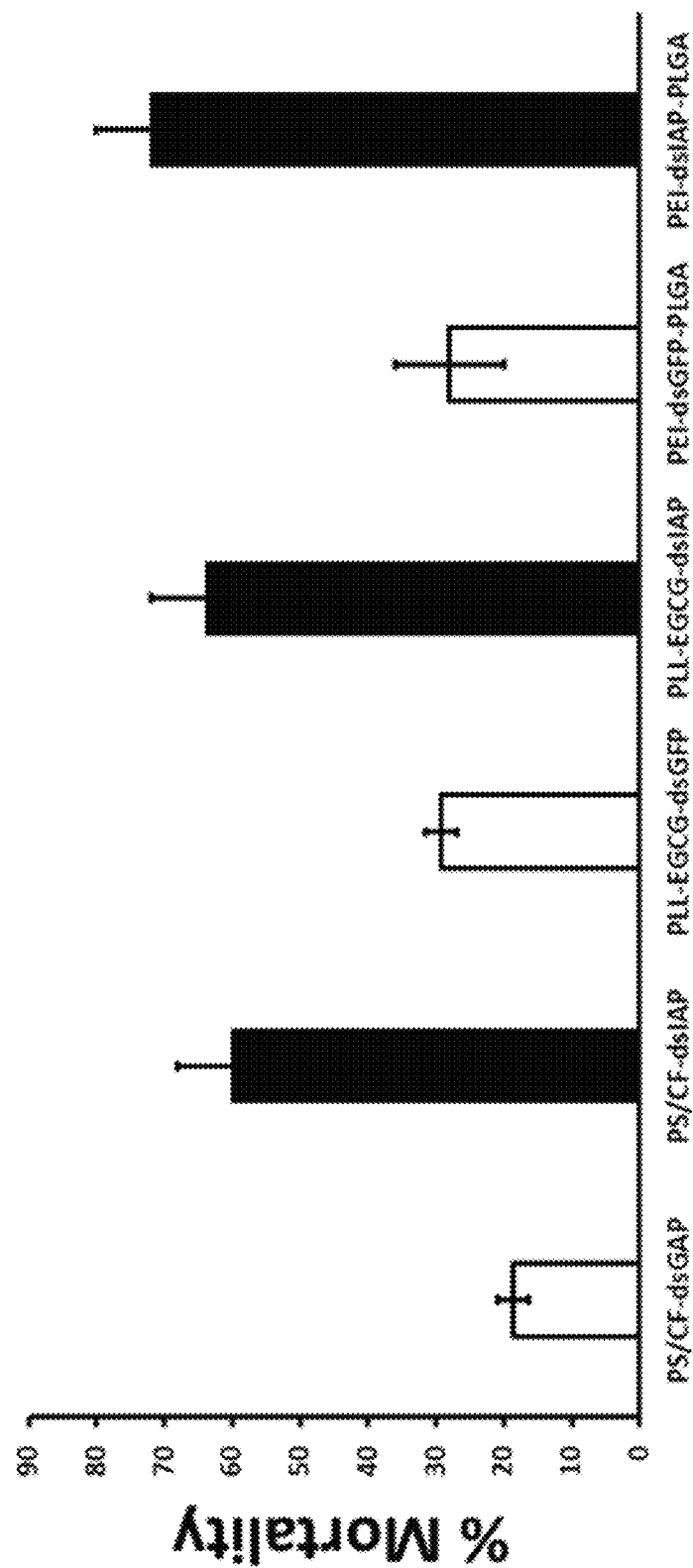
FIG. 37 shows PS:CF:dsRNA, PLL:EGCG:dsRNA and PEI:EGCG:PLGA nanoparticles induced RNAi in spodoptera neonates by sucrose feeding assay. Total 50 µg of dsGFP and dsIAP nanoparticles mixed with 5% sucrose solution were fed neonate *Spodoptera frugiperda*. The mortality was recorded up to 10 days of post feeding.

PS:CF:dsRNA, PLL:EGCG:dsRNA and PEI:PLGA:dsRNA nanoparticles induced RNAi in spodoptera neonates by sucrose feeding assay. Total 50 μg of dsGFP and dsIAP nanoparticles mixed with 5% sucrose solution were fed neonate *Spodoptera frugiperda*. The mortality was recorded up to 10 days of post feeding. (FIG. 37).

Figure 38:
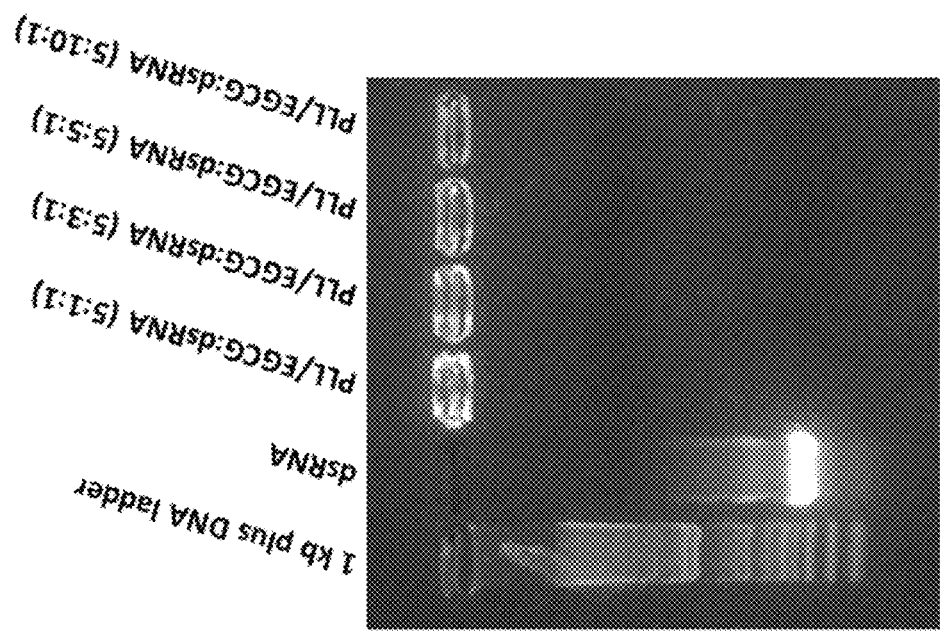
FIG. 38 shows The gel retardation assay of PLL:dsRNA and PLL:EGCG:dsRNA nanoparticles by agarose gel electrophoresis. Naked dsRNA, 1 kb plus DNA ladder, PLL:dsRNA and PLL:EGCG:dsRNA were resolved on 1% (W/V) agarose gel, stained with GelRed® and gel images were captured using Alpha Imager™ Gel Imagine System under a UV light.
Figure 38:
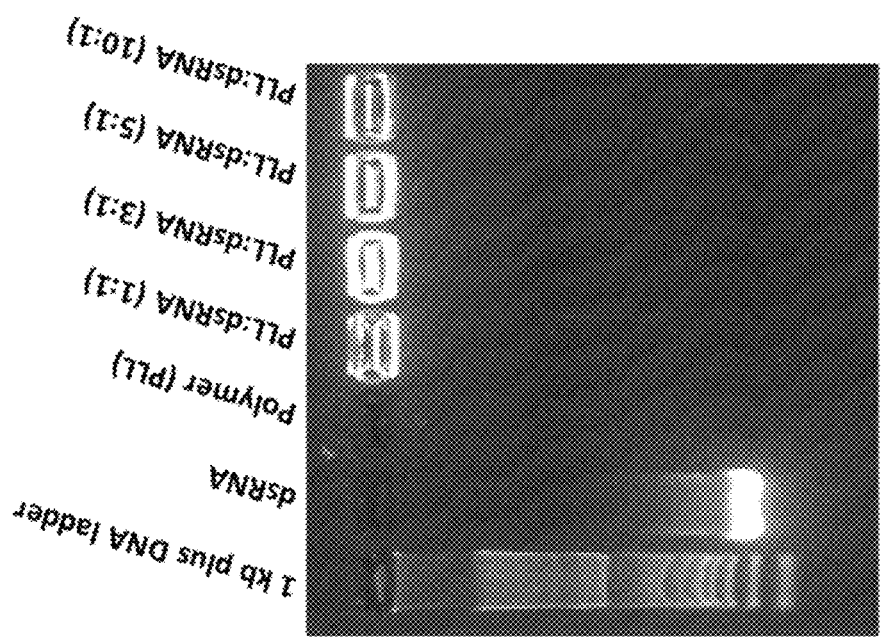

The gel retardation assay of PLL:dsRNA and PLL:EGCG:dsRNA nanoparticles by agarose gel electrophoresis. Naked dsRNA, 1 kb plus DNA ladder, PLL:dsRNA and PLL:EGCG:dsRNA were resolved on 1% (W/V) agarose gel, stained with GelRed® and gel images were captured using Alpha Imager™ Gel Imagine System under a UV light. (FIG. 38).

Figure 39:
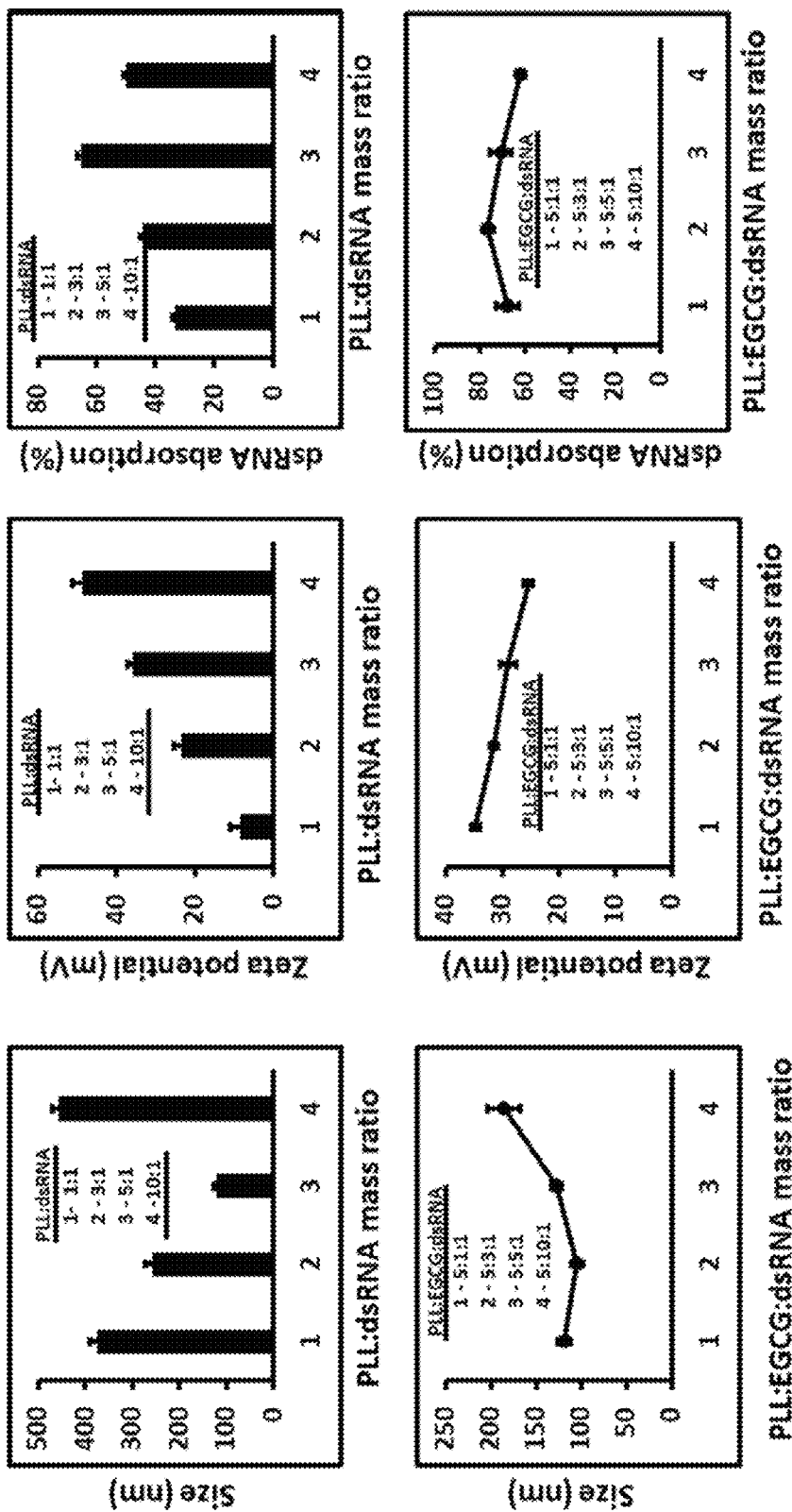
FIG. 39 shows Preparation and characterization of PLL:dsRNA and PLL:EGCG:dsRNA nanoparticles. The size, charge and percentage absorption of dsRNA determination of nanoparticles by dynamic light scattering
Figure 40:
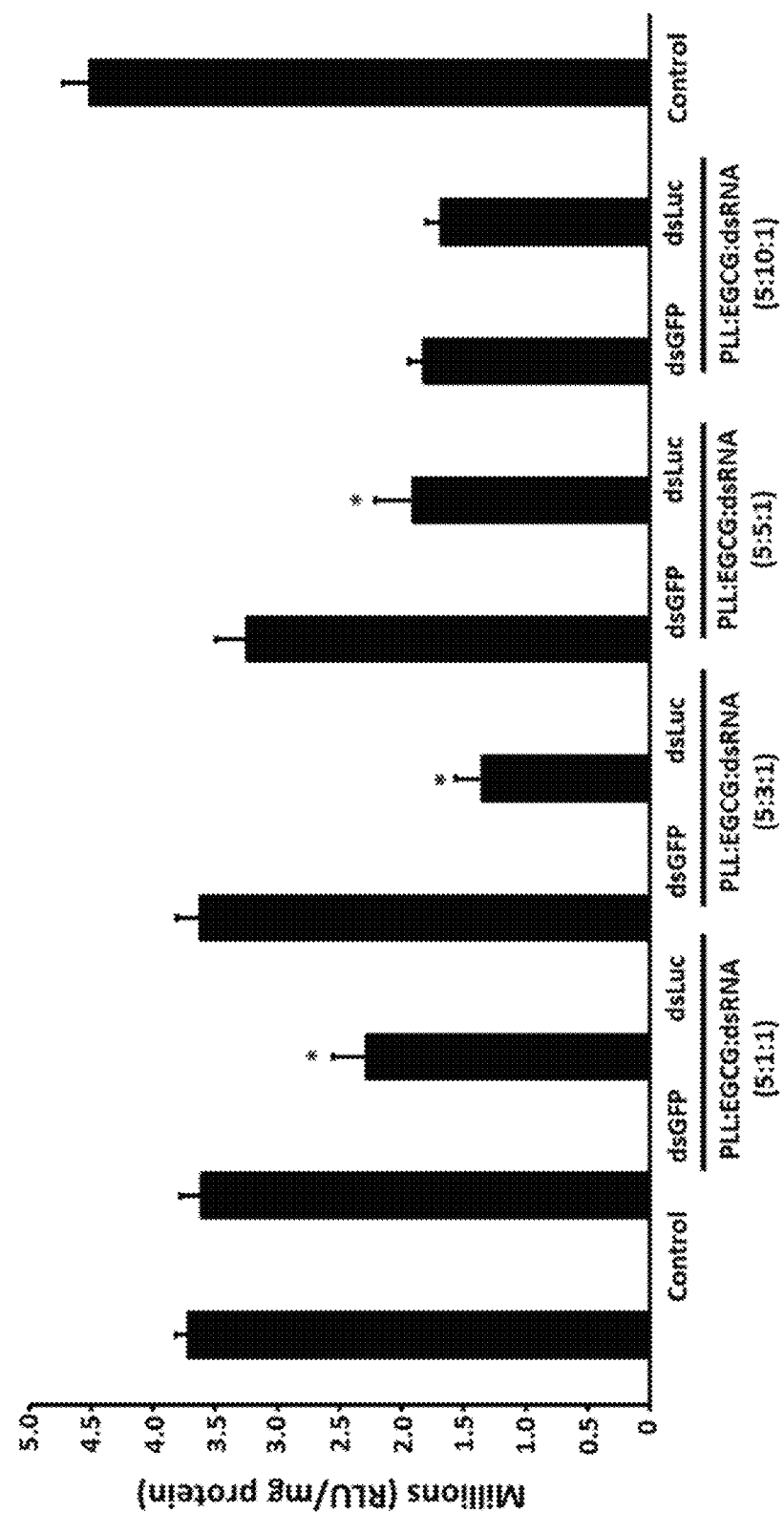
FIG. 40 shows Different ratio of PLL:EGCG:dsRNA nanoparticles testing the luciferase activity in Sf9 cells expressing the luciferase gene. The results showed that 66.7% reduced expression of the luciferase gene in the ratio of PLL:EGCG:dsRNA (5:3:1); Asterisk show the statistical difference ($P<0.05$).

Preparation and characterization of PLL:dsRNA and PLL:EGCG:dsRNA nanoparticles. The size, charge and percentage absorption of dsRNA determination of nanoparticles by dynamic light scattering (FIG. 39).

FIG. 40

Figure 41A:
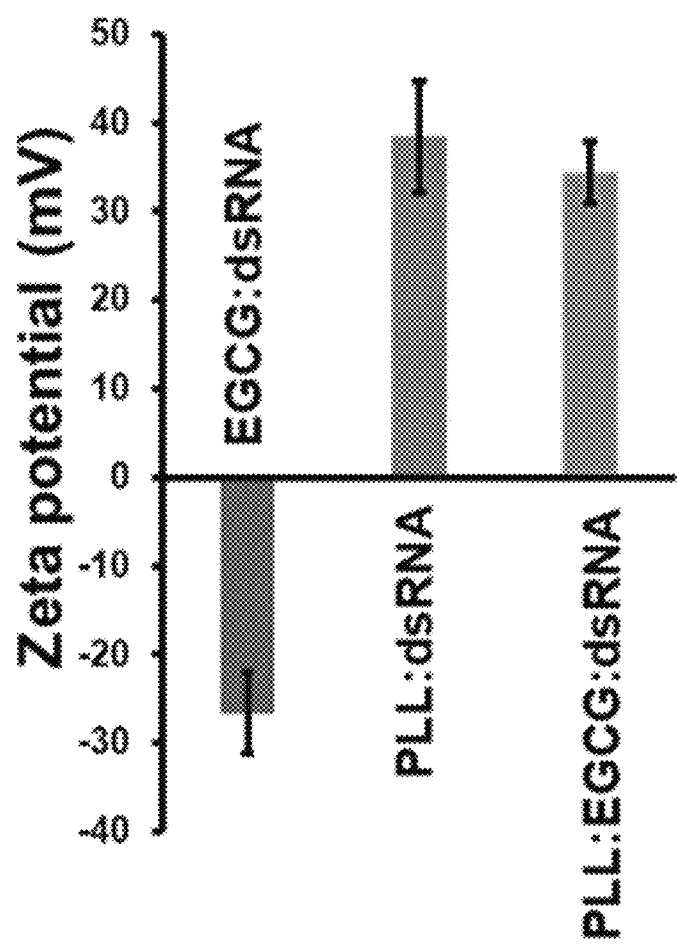
FIG. 41A shows preparation and characterization of PLL:EGCG:dsRNA (5:3:1) nanoparticles. The size and charge determination of nanoparticles by dynamic light scattering. The zeta potential of EGCG:dsRNA, PLL:dsRNA and PLL:EGCG:dsRNA nanoparticles were determined by photon correlation spectroscopy (PCS) using Zetasizer. All measurements were performed in triplicate at 25° C. and data are represented as mean±SE.
Figure 41B:
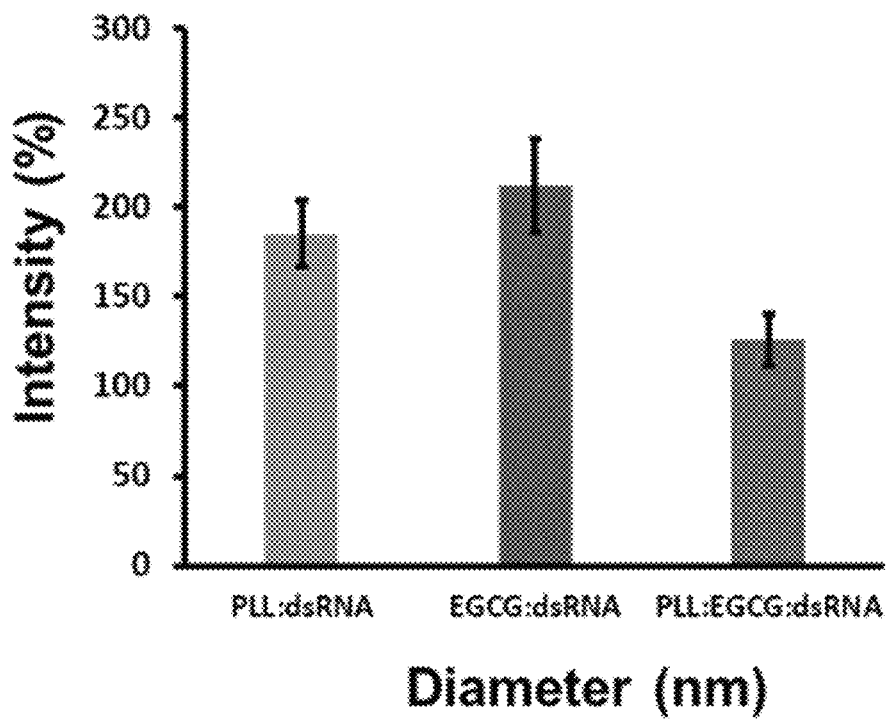
FIG. 41B shows preparation and characterization of PLL:EGCG:dsRNA (5:3:1) nanoparticles. The size and charge determination of nanoparticles by dynamic light scattering. The mean diameter (z-average) of EGCG:dsRNA, PLL:dsRNA and PLL:EGCG:dsRNA nanoparticles were determined by photon correlation spectroscopy (PCS) using Zetasizer. All measurements were performed in triplicate at 25° C. and data are represented as mean±SE.
Figure 41C:
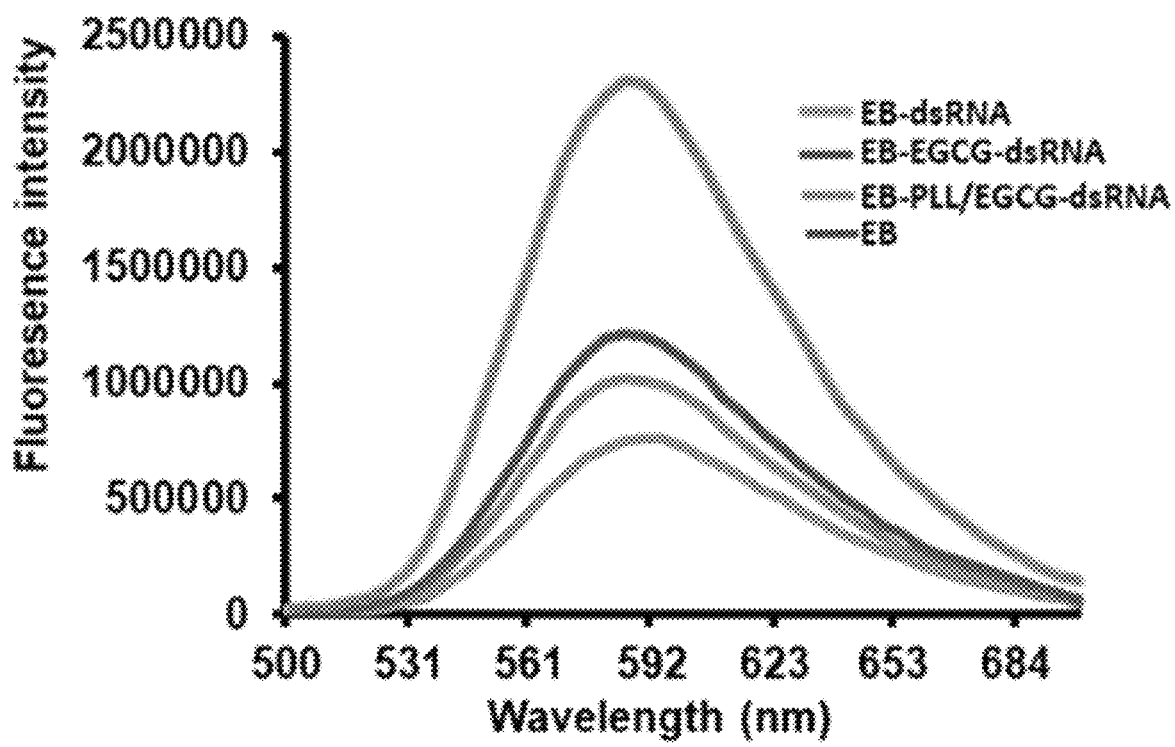
FIG. 41C shows preparation and characterization of PLL:EGCG:dsRNA (5:3:1) nanoparticles. One microgram of Ethidium bromide (EB) was mixed with naked dsRNA, EGCG:dsRNA and PLL:EGCG:dsRNA nanoparticles were measured by fluorescence spectroscopy, The binding of EGCG:dsRNA and PLL:EGCG:dsRNA caused the exclusion of EB from dsRNA and the quenching of EB fluorescence.

Preparation and characterization of PLL:EGCG:dsRNA (5:3:1) nanoparticles. The size and charge determination of nanoparticles by dynamic light scattering. The zeta potential of EGCG:dsRNA, PLL:dsRNA and PLL:EGCG:dsRNA nanoparticles were determined by photon correlation spectroscopy (PCS) using Zetasizer. All measurements were performed in triplicate at 25° C. and data are represented as mean±SE. (FIG. 41A). The mean diameter (z-average) of EGCG:dsRNA, PLL:dsRNA and PLL:EGCG:dsRNA nanoparticles were determined by photon correlation spectroscopy (PCS) using Zetasizer. All measurements were performed in triplicate at 25° C. and data are represented as mean±SE. (FIG. 41B). One microgram of Ethidium bromide (EB) was mixed with naked dsRNA, EGCG:dsRNA and PLL:EGCG:dsRNA nanoparticles were measured by fluorescence spectroscopy, The binding of EGCG:dsRNA and PLL:EGCG:dsRNA caused the exclusion of EB from dsRNA and the quenching of EB fluorescence. (FIG. 41C)

Figure 42:
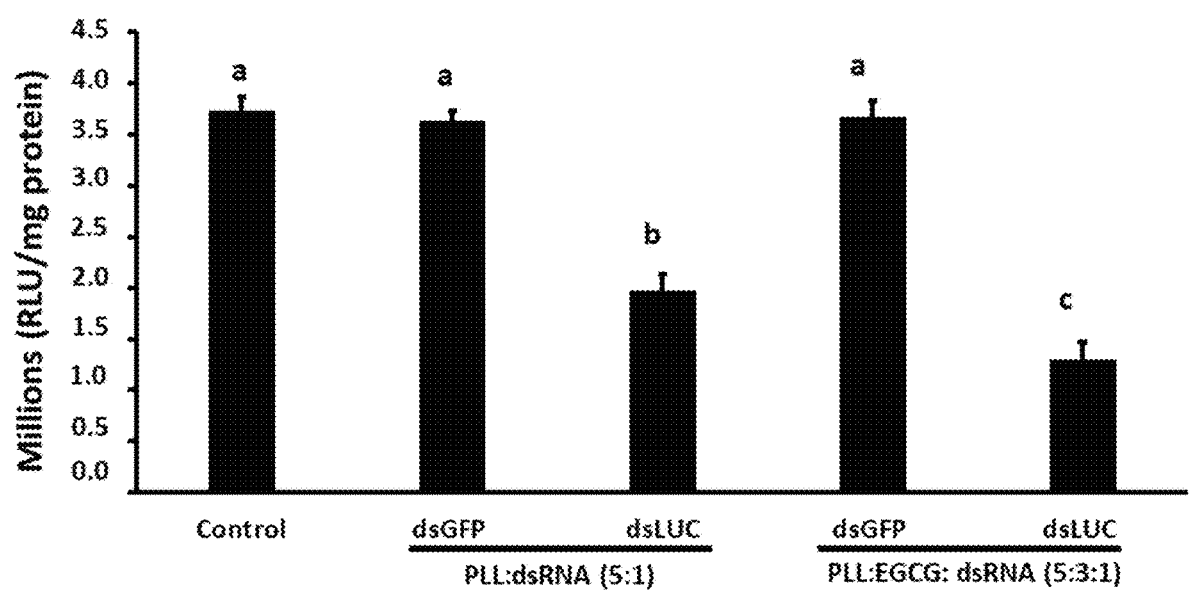
FIG. 42 shows Knockdown of the luciferase activity in Sf9 LUC stable cells by PLL:dsRNA and PLL:EGCG:dsRNA nanoparticles. Fifty thousand cells/well were seeded in 48-well plates. The cells were exposed 1 µg of PLL:dsRNA and PLL:EGCG:dsRNA luciferase dsRNA nanoparticles. At 72 h after treatment, the cells were washed, lysed and the luciferase activity was determined. The mean±SD (n=6) are shown.

Knockdown of the luciferase activity in Sf9_LUC stable cells by PLL:dsRNA and PLL:EGCG:dsRNA nanoparticles. Fifty thousand cells/well were seeded in 48-well plates. The cells were exposed 1 μg of PLL:dsRNA and PLL:EGCG:dsRNA luciferase dsRNA nanoparticles. At 72 h after treatment, the cells were washed, lysed and the luciferase activity was determined. The mean±SD (n=6) are shown. (FIG. 42).

Figure 43:
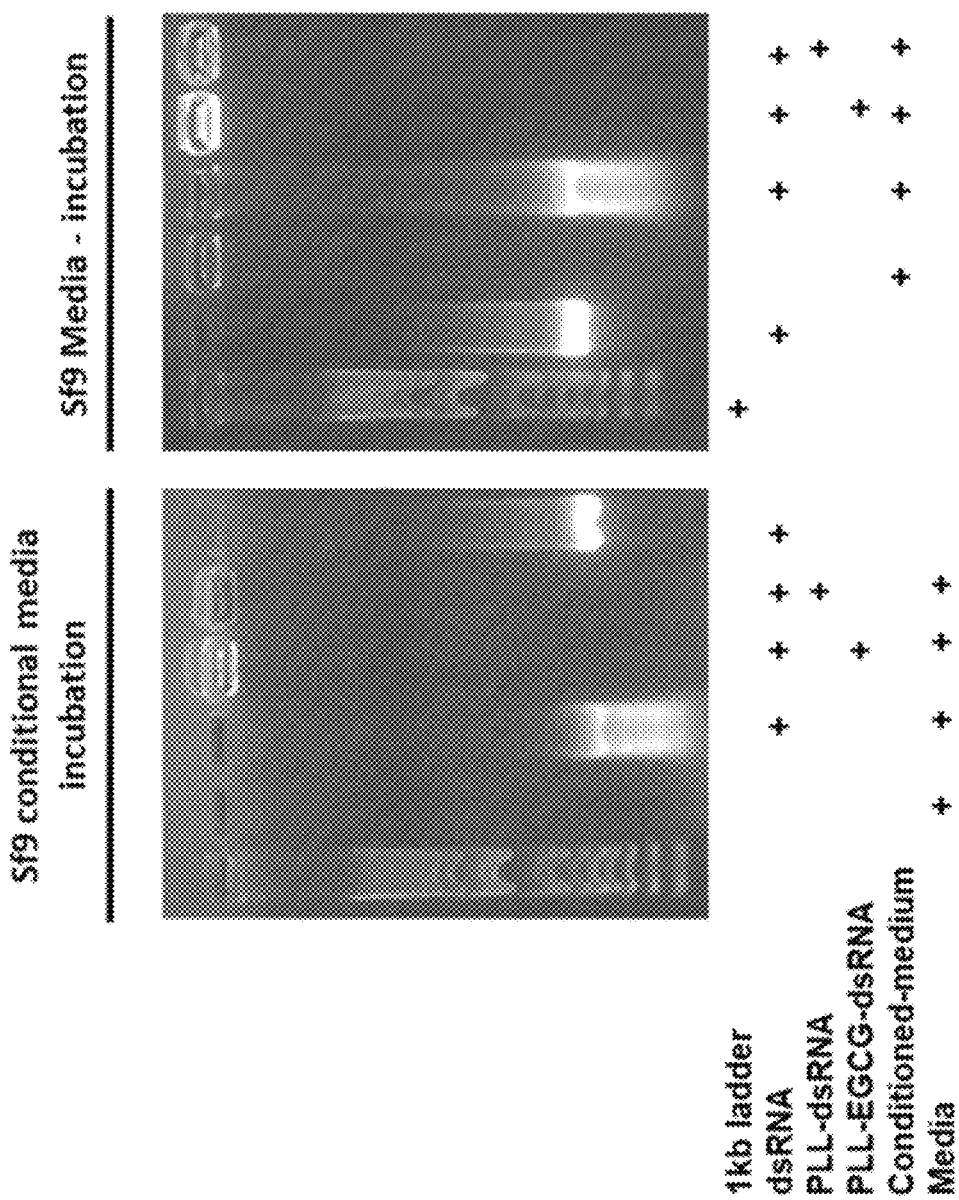
FIG. 43 shows stability of dsRNA in the Sf-9 media and Sf-9 conditional media. One microgram of naked dsRNA, PLL:dsRNA and PLL:EGCG:dsRNA was exposed to media and conditional media for 1 hr. After exposure, the sample mixtures were collected and analyzed in 1% agarose gel electrophoresis.

Stability of dsRNA in the Sf-9 media and Sf-9 conditional media. One microgram of naked dsRNA, PLL:dsRNA and PLL:EGCG:dsRNA was exposed to media and conditional media for 1 hr. After exposure, the sample mixtures were collected and analyzed in 1% agarose gel electrophoresis. (FIG. 43).

Figure 44:
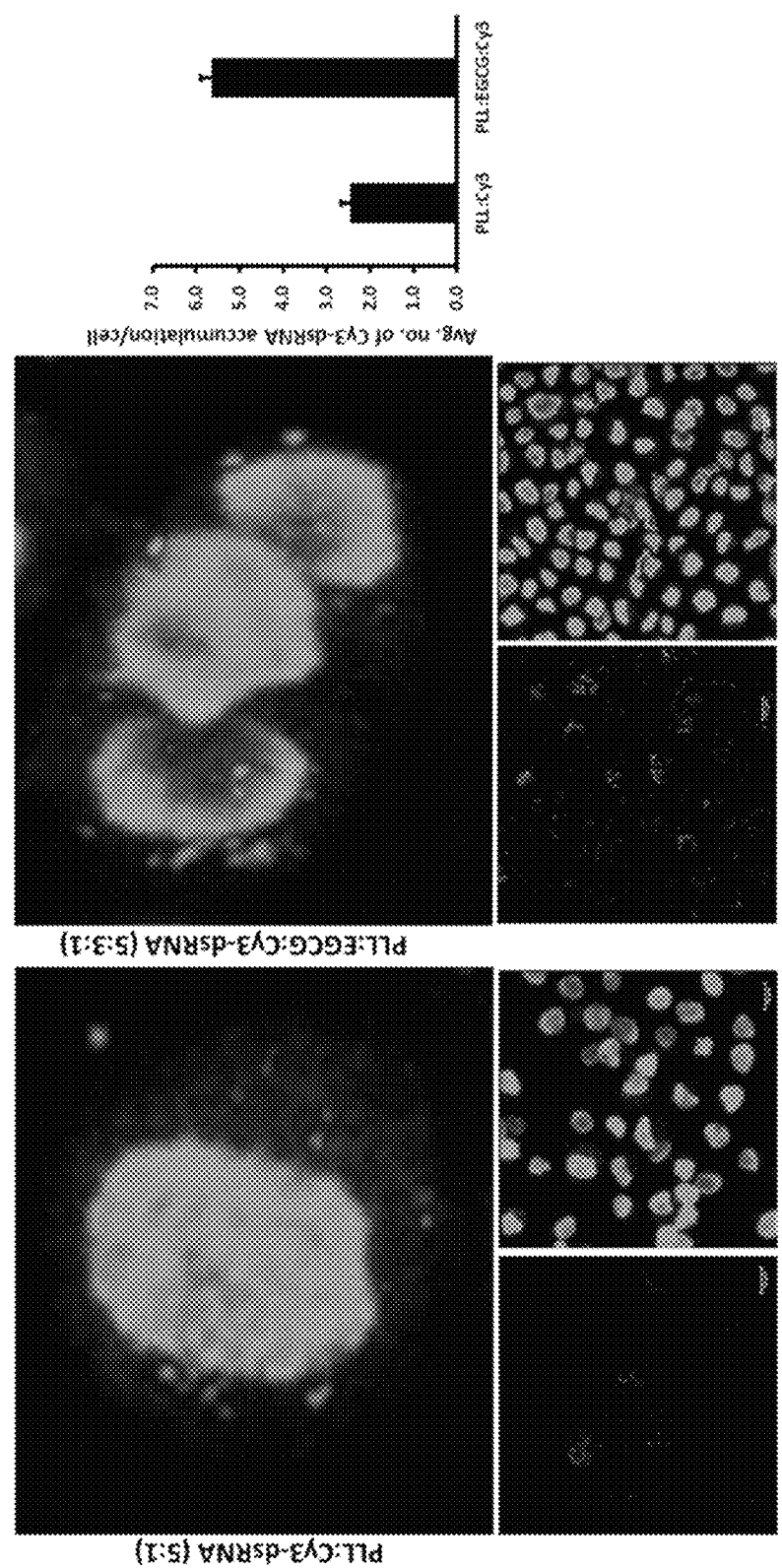
FIG. 44 shows confocal microscopic imaging of the cellular uptake of the PLL:Cy3-dsRNA and PLL:EGCG:Cy3-dsRNA nanoparticles after incubation of 4 hr. Red channel image shows the Cy-3 labeled dsRNA and blue channel image shows the nuclei of Sf-9 cells stained by DAPI. The number of Cy3-labeled dsRNA accumulating cytosol were counted and plotted (n=100).

Shows confocal microscopic imaging of the cellular uptake of the PLL:Cy3-dsRNA and PLL:EGCG:Cy3-dsRNA nanoparticles after incubation of 4 hr. Red channel image shows the Cy-3 labeled dsRNA and blue channel image shows the nuclei of Sf-9 cells stained by DAPI. The number of Cy3-labeled dsRNA accumulating cytosol were counted and plotted (n=100). (FIG. 44)

Figures 45A, 45B:
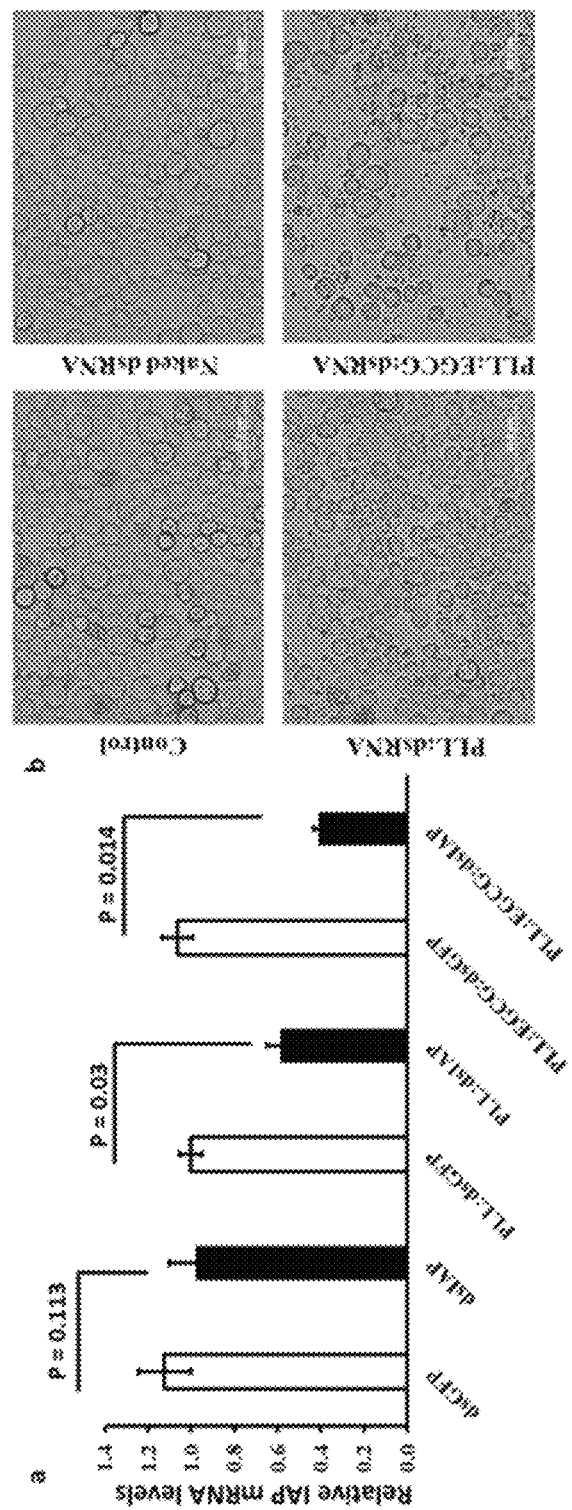
FIG. 45A shows Gene knockdown efficiency of Naked dsRNA, PLL:dsRNA and PLL:EGCG:dsRNA in Sf-9 cells. The relative IAP gene mRNA levels were quantified by qRT-PCR. Mean±SE (n=5) are shown.
FIG. 45B shows Gene knockdown efficiency of Naked dsRNA, PLL:dsRNA and PLL:EGCG:dsRNA in Sf-9 cells. The downregulation of IAP gene expression showed Phenotypic changes in Sf-9 cells.

Gene knockdown efficiency of Naked dsRNA, PLL:dsRNA and PLL:EGCG:dsRNA in Sf-9 cells. The relative IAP gene mRNA levels were quantified by qRT-PCR. Mean±SE (n=5) are shown. (FIG. 45A). The downregulation of IAP gene expression showed Phenotypic changes in Sf-9 cells. (FIG. 45B).

Figures 46A, 46B:
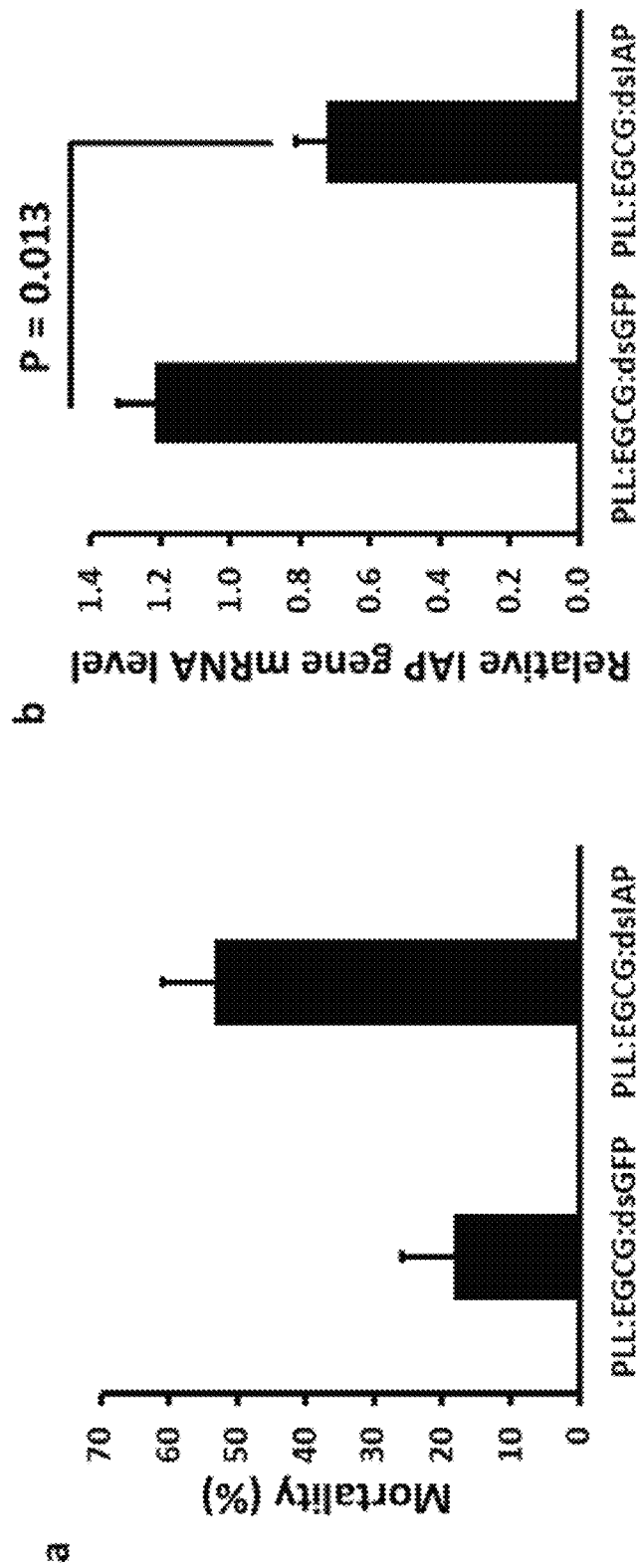
FIG. 46A shows Mortality induced by orally delivered dsRNA in *Spodoptera* neonates. PLL:EGCG:dsRNA nanoparticles were mixed with 5% sucrose solution was fed to newly hatched *Spodoptera* neonates. one microgram of nanoparticles were fed to the neonates and five micrograms of nanoparticles incorporate into diet and larvae fed up to three days. After 10 days, post-feeding mortality was scored. Mean±SE (n=3) are shown.
FIG. 46B shows Mortality induced by orally delivered dsRNA in *Spodoptera* neonates. PLL:EGCG:dsRNA nanoparticles induce efficient knockdown in *Spodoptera* larvae feeding bioassay.

Mortality induced by orally delivered dsRNA in *Spodoptera* neonates. PLL:EGCG:dsRNA nanoparticles were mixed with 5% sucrose solution was fed to newly hatched *Spodoptera* neonates. one microgram of nanoparticles were fed to the neonates and five micrograms of nanoparticles incorporate into diet and larvae fed up to three days. After 10 days, post-feeding mortality was scored. Mean±SE (n=3) are shown. (FIG. 46A).

Mortality induced by orally delivered dsRNA in *Spodoptera* neonates. PLL:EGCG:dsRNA nanoparticles induce efficient knockdown in *Spodoptera* larvae feeding bioassay. (FIG. 46B).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Each of the following references is herein incorporated by reference in its entirety.

1. Liu, N. Insecticide resistance in mosquitoes: impact, mechanisms, and research directions. Annu Rev Entomol. 60, 537-559, doi: 10.1146/annurev-ento-010814-020828 (2015).
2. Weetman, D., Mitchell, S. N., Wilding, C. S., Birks, D. P., Yawson, A. E., Essandoh, J., Mawejje, H. D., Djogbenou, L. S., Steen, K., Rippon, E. J. & Clarkson, C. S. Contemporary evolution of resistance at the major insecticide target site gene Ace-1 by mutation and copy number variation in the malaria mosquito *Anopheles gambiae*. Mol Ecol. 24(11), 2656-2672. doi: 10.1111/mec.13197 (2015).
3. Fire, A., Xu, S., Montgomery, M. K., Kostas, S. A., Driver, S. E. & Mello, C. C. Potent and specific genetic interference by double-stranded RNA in *Caenorhabditis elegans*. Nature. 391(6669), 806. doi: 10.1038/35888 (1998).
4. Salame, T. M., Ziv, C., Hadar, Y. & Yarden, O. RNAi as a potential tool for biotechnological applications in fungi. Appl Microbiol Biotechnol. 89(3), 501-512. doi: 10.1007/s00253-010-2928-1 (2011).
5. Kusaba, M. RNA interference in crop plants. Curr Opin Biotechnol. 15(2), 139-143. doi: 10.1016/j.copbio.2004.02.004 (2004).
6. Baum, J. A., Bogaert, T., Clinton, W., Heck, G. R., Feldmann, P., Ilagan, O., Johnson, S., Plaetinck, G., Munyikwa, T., Pleau, M. & Vaughn, T. Control of coleopteran insect pests through RNA interference. Nat Biotechnol. 25(11), 1322. doi: 10.1038/nbt1359 (2007).
7. Bumcrot, D., Manoharan, M., Koteliansky, V. & Sah, D. W. RNAi therapeutics: a potential new class of pharmaceutical drugs. Nat Chem Biol. 2(12), 711. doi: 10.1038/nchembio839 (2006).
8. Zhu, F., Xu, J., Palli, R., Ferguson, J. & Palli, S. R. Ingested RNA interference for managing the populations of the Colorado potato beetle, *Leptinotarsa decemlineata*. Pest Manag Sci. 67(2), 175-182. doi: 10.1002/ps.2048 (2011).
9. Palli, S. R. RNA interference in Colorado potato beetle: steps toward development of dsRNA as a commercial insecticide. Curr Opin Insect Sci. 6, 1-8. doi: 10.1016/j.cois.2014.09.011 (2014).
10. Miller, S. C., Brown, S. J. & Tomoyasu, Y. Larval RNAi in Drosophila?. Dev Genes Evol. 218(9), 505-510. doi: 10.1007/s00427-008-0238-8 (2008).
11. Urban-Klein, B., Werth, S., Abuharbeid, S., Czubayko, F. & Aigner, A. RNAi-mediated gene-targeting through systemic application of polyethylenimine (PEI)-complexed siRNA in vivo. Gene Ther. 12(5), 461. doi: 10.1038/sj.gt.3302425 (2005).
12. Tomoyasu, Y., Miller, S. C., Tomita, S., Schoppmeier, M., Grossmann, D. & Bucher, G. Exploring systemic RNA interference in insects: a genome-wide survey for RNAi genes in Tribolium. Genome Biol. 9(1), R10. doi: 10.1186/gb-2008-9-1-r10 (2008).
13. Garbutt, J. S., Bellés, X., Richards, E. H. & Reynolds, S. E. Persistence of double-stranded RNA in insect hemolymph as a potential determiner of RNA interference success: evidence from *Manduca sexta* and *Blattella germanica*. J Insect Physiol. 59(2), 171-178. doi: 10.1016/j.jinsphys.2012.05.013 (2013).
14. Kim, T. H., Kim, S. I., Akaike, T. & Cho, C. S. Synergistic effect of poly (ethylenimine) on the transfection efficiency of galactosylated chitosan/DNA complexes. J Control Release. 105(3), 354-366. doi: 10.1016/j.jconrel.2005.03.024 (2005).
15. Park, T. G., Jeong, J. H. & Kim, S. W. Current status of polymeric gene delivery systems. Adv Drug Deliv Rev. 58(4), 467-486. doi: 10.1016/j.addr.2006.03.007 (2006).
16. Lee, M. K., Chun, S. K., Choi, W. J., Kim, J. K., Choi, S. H., Kim, A., Oungbho, K., Park, J. S., Ahn, W. S. & Kim, C. K. The use of chitosan as a condensing agent to enhance emulsion-mediated gene transfer. Biomaterials. 26(14), 2147-2156. doi: 10.1016/j.biomaterials.2004.07.008 (2005).
17. Shu, X. Z. & Zhu, K. J. The influence of multivalent phosphate structure on the properties of ionically cross-linked chitosan films for controlled drug release. Eur J Pharm Biopharm. 54(2), 235-243. doi.org/10.1016/S0939-6411(02)00052-8 (2002).
18. Mao, S., Sun, W. & Kissel, T. Chitosan-based formulations for delivery of DNA and siRNA. Adv Drug Deliv Rev. 62(1), 12-27. doi: 10.1016/j.addr.2009.08.004 (2010)
19. Malmo, J., Vårum, K. M. & Strand, S. P. Effect of chitosan chain architecture on gene delivery: comparison of self-branched and linear chitosans. Biomacromolecules. 12(3), 721-729. doi: 10.1021/bm1013525 (2011).
20. Zhang, X., Zhang, J. & Zhu, K. Y. Chitosan/double-stranded RNA nanoparticle-mediated RNA interference to silence chitin synthase genes through larval feeding in the African malaria mosquito (*Anopheles gambiae*). Insect Mol Biol. 19(5), 683-693. doi: 10.1111/j.1365-2583.2010.01029.x (2010).
21. Mysore, K., Flannery, E. M., Tomchaney, M., Severson, D. W. & Duman-Scheel, M. Disruption of *Aedes aegypt* olfactory system development through chitosan/siRNA nanoparticle targeting of semaphorin-1a. PLoS Negl Trop Dis. 7(5), 2215. doi: 10.1371/journal.pntd.0002215 (2013).
22. Kumar, D. R., Kumar, P. S., Gandhi, M. R., Al-Dhabi, N. A., Paulraj, M. G. & Ignacimuthu, S., 2016. Delivery of chitosan/dsRNA nanoparticles for silencing of wing development vestigial (vg) gene in *Aedes aegypt* mosquitoes. Int J Biol Macromol. 86, 89-95. doi: 10.1016/j.ijbiomac.2016.01.030 (2016).
23. Ko, J. A., Park, H. J., Hwang, S. J., Park, J. B. & Lee, J. S. Preparation and characterization of chitosan microparticles intended for controlled drug delivery. Int J Pharm. 249(1-2), 165-174. doi.org/10.1016/S0378-5173(02)00487-8 (2002).
24. Raja, M. A. G., Katas, H. & Wen, T. J. Stability, intracellular delivery, and release of siRNA from chitosan nanoparticles using different cross-linkers. PLoS One. 10(6). doi: 10.1371/journal.pone.0128963 (2015).
25. Katas, H. & Alpar, H. O. Development and characterisation of chitosan nanoparticles for siRNA delivery. J Control Release. 115(2), 216-225. DOI: 10.1016/j.jconrel.2006.07.021 (2006).
26. Nasti, A., Zaki, N. M., de Leonardis, P., Ungphaiboon, S., Sansongsak, P., Rimoli, M. G. & Tirelli, N. Chitosan/TPP and chitosan/TPP-hyaluronic acid nanoparticles: systematic optimisation of the preparative process and preliminary biological evaluation. Pharm Res. 26(8), 1918-1930. DOI: 10.1007/s11095-009-9908-0 (2009).
27. Liu, H. & Gao, C. Preparation and properties of ionically cross-linked chitosan nanoparticles. Polym. Adv. Technol. 20(7), 613-619. DOI: 10.1002/pat.1306 (2009).
28. Calvo, P., Remunan-Lopez, C., Vila-Jato, J. L. & Alonso, M. J., 1997. Novel hydrophilic chitosan-polyethylene oxide nanoparticles as protein carriers. J. Appl. Polym. Sci. 63(1), 125-132. doi.org/10.1002/(SICI)1097-4628(19970103)63:1<125::AID-APP13>3.0.CO;2-4 (1997).
29. Hu, B., Pan, C., Sun, Y., Hou, Z., Ye, H., Hu, B. & Zeng, X. Optimization of fabrication parameters to produce chitosan-tripolyphosphate nanoparticles for delivery of tea catechins. J Agric Food Chem. 56(16), 7451-7458. doi: 10.1021/jf801111c (2008).
30. Harris, R., Lecumberri, E., Mateos-Aparicio, I., Mengíbar, M. & Heras, A. Chitosan nanoparticles and microspheres for the encapsulation of natural antioxidants extracted from Ilex paraguariensis. Carbohydr Polym. 84(2), 803-806. doi.org/10.1016/j.carbpol.2010.07.003 (2011).
31. Gan, Q. & Wang, T. Chitosan nanoparticle as protein delivery carrier—systematic examination of fabrication conditions for efficient loading and release. Colloids Surf B Biointerfaces. 59(1), 24-34. doi: 10.1016/j.colsurfb.2007.04.009 (2007).
32. Sun, Y. & Wan, A. Preparation of nanoparticles composed of chitosan and its derivatives as delivery systems for macromolecules. J. Appl. Polym. Sci. 105(2), 552-561 (2007).
33. Lin, Y. H., Mi, F. L., Chen, C. T., Chang, W. C., Peng, S. F., Liang, H. F. & Sung, H. W. Preparation and characterization of nanoparticles shelled with chitosan for oral insulin delivery. Biomacromolecules. 8(1), 146-152. doi: 10.1021/bm0607776 (2007).
34. Raj, L. F. A. A., Jonisha, R., Revathi, B. & Jayalakshmy, E. Preparation and characterization of BSA and chitosan nanopartices for sustainable delivery system for quercetin. J. Appl. Pharm. Sci. 5, 1-5 (2015).
35. Grenha, A., Seijo, B. & Remunan-López, C. Microencapsulated chitosan nanoparticles for lung protein delivery. Eur J Pharm Sci. 25(4-5), 427-437. doi: 10.1016/j.ejps.2005.04.009 (2005).
36. Janes, K. A., Calvo, P. & Alonso, M. J. Polysaccharide colloidal particles as delivery systems for macromolecules. Adv Drug Deliv Rev. 47(1), 83-97. doi.org/10.1016/S0169-409X(00)00123-X (2001).
37. Howard, K. A. Delivery of RNA interference therapeutics using polycation-based nanoparticles. Adv Drug Deliv Rev. 61(9), 710-720. doi: 10.1016/j.addr.2009.04.001 (2009).
38. Panyam, J. & Labhasetwar, V. Biodegradable nanoparticles for drug and gene delivery to cells and tissue. Adv Drug Deliv Rev. 55(3), 329-347. doi.org/10.1016/S0169-409X(02)00228-4 (2003).
39. Vandenberg, G. W., Drolet, C., Scott, S. L. & De la Noüe, J. Factors affecting protein release from alginate—chitosan coacervate microcapsules during production and gastric/intestinal simulation. J Control Release. 77(3), 297-307. doi.org/10.1016/S0168-3659(01)00517-X (2001).
40. Papadimitriou, S. A., Achilias, D. S. & Bikiaris, D. N. Chitosan-g-PEG nanoparticles ionically crosslinked with poly (glutamic acid) and tripolyphosphate as protein delivery systems. Int J Pharm. 430(1-2), 318-327. doi: 10.1016/j.ijpharm.2012.04.004 (2012).
41. Ahmad Nor, Y., Niu, Y., Karmakar, S., Zhou, L., Xu, C., Zhang, J., Zhang, H., Yu, M., Mahony, D., Mitter, N. & Cooper, M. A. Shaping nanoparticles with hydrophilic compositions and hydrophobic properties as nanocarriers for antibiotic delivery. ACS Cent Sci. 1(6), 328-334. doi: 10.1021/acscentsci.5b00199 (2015).
42. Rampino, A., Borgogna, M., Blasi, P., Bellich, B. & Cesàro, A. Chitosan nanoparticles: preparation, size evolution and stability. Int J Pharm. 455(1-2), 219-228. doi: 10.1016/j.ijpharm.2013.07.034 (2013).
43. Sonawane, N. D., Szoka, F. C. & Verkman, A. S. Chloride accumulation and swelling in endosomes enhances DNA transfer by polyamine-DNA polyplexes. J Biol Chem. 278(45), 44826-44831. doi: 10.1074/jbc.M308643200 (2003).
44. Phanse, Y., Dunphy, B. M., Perry, J. L., Airs, P. M., Paquette, C. C., Carlson, J. O., Xu, J., Luft, J. C., DeSimone, J. M., Beaty, B. J. & Bartholomay, L. C. Biodistribution and toxicity studies of print hydrogel nanoparticles in mosquito larvae and cells. PLoS Negl Trop Dis. 9(5). doi: 10.1371/journal.pntd.0003735 (2005).
45. Paquette, C. C., Phanse, Y., Perry, J. L., Sanchez-Vargas, I., Airs, P. M., Dunphy, B. M., Xu, J., Carlson, J. O., Luft, J. C., DeSimone, J. M. & Bartholomay, L. C. Biodistribution and trafficking of hydrogel nanoparticles in adult mosquitoes. PLoS Negl Trop Dis. 9(5). doi: 10.1371/journal.pntd.0003745 (2015).
46. Wischke, C., Borchert, H. H., Zimmermann, J., Siebenbrodt, I. and Lorenzen, D. R. Stable cationic microparticles for enhanced model antigen delivery to dendritic cells. J Control Release. 114(3), 359-368. doi: 10.1016/j.jconrel.2006.06.020 (2006).
47. Huang, Q., Deveraux, Q. L., Maeda, S., Stennicke, H. R., Hammock, B. D. & Reed, J. C. Cloning and characterization of an inhibitor of apoptosis protein (IAP) from *Bombyx mori*. Biochim Biophys Acta. 1499(3), 191-198. doi.org/10.1016/S0167-4889(00)00105-1 (2001).
48. Wang, H. & Clem, R. J. The role of IAP antagonist proteins in the core apoptosis pathway of the mosquito disease vector *Aedes aegypti*. Apoptosis. 16(3), 235-248. doi: 10.1007/s10495-011-0575-3 (2011).
49. Puglise, J. M., Estep, A. S. & Becnel, J. J. Expression profiles and RNAi silencing of Inhibitor of *Apoptosis* transcripts in *Aedes, Anopheles*, and Culex mosquitoes (Diptera: Culicidae). J Med Entomol. 53(2), 304-314. doi: 10.1093/jme/tjv191 (2015).
50. Walker I I I, W. B. & Allen, M. L. RNA interference-mediated knockdown of IAP in *Lygus lineolaris* induces mortality in adult and pre-adult life stages. Entomol. Exp. Appl. 138(2), 83-92. doi: 10.1111/j.1570-7458.2010.01078.x (2011).
51. Mogilicherla, K., Howell, J. L. & Palli, S. R. Improving RNAi in the Brown Marmorated Stink Bug: Identification of target genes and reference genes for RT-qPCR. Sci Rep. 8(1), 3720. doi: 10.1038/s41598-018-22035-z (2018).
52. Rodrigues, T. B., Dhandapani, R. K., Duan, J. J. & Palli, S. R. RNA interference in the Asian Longhorned Beetle: Identification of Key RNAi Genes and Reference Genes for RT-qPCR. Sci Rep. 7(1), 8913. doi: 10.1038/s41598-017-08813-1 (2017).
53. Rodrigues, T. B., Rieske, L. K., Duan, J., Mogilicherla, K. & Palli, S. R. Development of RNAi method for screening candidate genes to control emerald ash borer, *Agrilus planipennis*. Sci Rep. 7(1), 7379. doi: 10.1038/s41598-017-07605-x (2017).
54. Das, S., Debnath, N., Cui, Y., Unrine, J. & Palli, S. R. Chitosan, carbon quantum dot, and silica nanoparticle mediated dsRNA delivery for gene silencing in *Aedes aegypti*: a comparative analysis. ACS Appl Mater Interfaces. 7(35), 19530-19535. doi: 10.1021/acsami.5b05232 (2015).
55. Shu, S., Sun, C., Zhang, X., Wu, Z., Wang, Z. & Li, C. Hollow and degradable polyelectrolyte nanocapsules for protein drug delivery. Acta Biomater. 6(1), 210-217. doi.org/10.1016/j.actbio.2009.06.020 (2010)
56. Shukla, J. N., Kalsi, M., Sethi, A., Narva, K. E., Fishilevich, E., Singh, S., Mogilicherla, K. & Palli, S. R. Reduced stability and intracellular transport of dsRNA contribute to poor RNAi response in lepidopteran insects. RNA Biol. 13(7), 656-669. doi: 10.1080/15476286.2016.1191728 (2016).
57. Ge, Y., Zhang, Y., He, S., Nie, F., Teng, G. and Gu, N. Fluorescence modified chitosan-coated magnetic nanoparticles for high-efficient cellular imaging. Nanoscale Res Lett. 4(4), 287. doi: 10.1007/s11671-008-9239-9 (2009).
58. Bai, H., Ramaseshadri, P. & Palli, S. R. Identification and characterization of juvenile hormone esterase gene from the yellow fever mosquito, *Aedes aegypti*. Insect Biochem Mol Biol. 37(8), 829-837. doi: 10.1016/j.ibmb.2007.05.010 (2007).

59. Hu, X., Richtman, N. M., Zhao, J. Z., Duncan, K. E., Niu, X., Procyk, L. A., Oneal, M. A., Kernodle, B. M., Steimel, J. P., Crane, V. C. & Sandahl, G. Discovery of midgut genes for the RNA interference control of corn rootworm. Sci Rep. 6, 30542. doi: 10.1038/srep30542 (2016).

60. Mysore, K., Hapairai, L. K., Sun, L., Harper, E. I., Chen, Y., Eggleson, K. K., Realey, J. S., Scheel, N. D., Severson, D. W., Wei, N. & Duman-Scheel, M. Yeast interfering RNA larvicides targeting neural genes induce high rates of *Anopheles* larval mortality. Malar J.16(1), 461. doi: 10.1186/s12936-017-2112-5 (2017).

61. Zhu, K. Y. and S. R. Palli, *Mechanisms, Applications, and Challenges of Insect RNA Interference*. Annu Rev Entomol, 2020. 65: p. 293-311.

62. Wynant, N., D. Santos, and J. Vanden Broeck, *Biological mechanisms determining the success of RNA interference in insects*. Int Rev Cell Mol Biol, 2014. 312: p. 139-67.

63. Shukla, J. N., et al., *Reduced stability and intracellular transport of dsRNA contribute to poor RNAi response in lepidopteran insects*. RNA Biol, 2016. 13(7): p. 656-69.

64. Singh, I. K., et al., *Comparative analysis of double-stranded RNA degradation and processing in insects*. Sci Rep, 2017. 7(1): p. 17059.

65. Christiaens, O., L. Swevers, and G. Smagghe, *DsRNA degradation in the pea aphid (Acyrthosiphon pisum) associated with lack of response in RNAi feeding and injection assay*. Peptides, 2014. 53: p. 307-14.

66. Yoon, J. S., D. Gurusamy, and S. R. Palli, *Accumulation of dsRNA in endosomes contributes to inefficient RNA interference in the fall armyworm, Spodoptera frugiperda*. Insect Biochem Mol Biol, 2017. 90: p. 53-60.

67. Spit, J., et al., *Knockdown of nuclease activity in the gut enhances RNAi efficiency in the Colorado potato beetle, Leptinotarsa decemlineata, but not in the desert locust, Schistocerca gregaria*. Insect Biochem Mol Biol, 2017. 81: p. 103-116.

68. Song, H., et al., *A double-stranded RNA degrading enzyme reduces the efficiency of oral RNA interference in migratory locust*. Insect Biochem Mol Biol, 2017. 86: p. 68-80.

69. Peng, Y., et al., *Identification and characterization of multiple dsRNases from a lepidopteran insect, the tobacco cutworm, Spodoptera litura (Lepidoptera: Noctuidae)*. Pestic Biochem Physiol, 2020. 162: p. 86-95.

70. He, B., et al., *Fluorescent nanoparticle delivered dsRNA toward genetic control of insect pests*. Adv Mater, 2013. 25(33): p. 4580-4.

71. Zhang, X., J. Zhang, and K. Y. Zhu, *Chitosan/double-stranded RNA nanoparticle-mediated RNA interference to silence chitin synthase genes through larval feeding in the African malaria mosquito (Anopheles gambiae)*. Insect Mol Biol, 2010. 19(5): p. 683-93.

72. Das, S., et al., *Chitosan, Carbon Quantum Dot, and Silica Nanoparticle Mediated dsRNA Delivery for Gene Silencing in Aedes aegypti: A Comparative Analysis*. ACS Appl Mater Interfaces, 2015. 7(35): p. 19530-5.

73. Christiaens, O., et al., *Increased RNAi Efficacy in Spodoptera exigua via the Formulation of dsRNA With Guanylated Polymers*. Front Physiol, 2018. 9: p. 316.

74. Liang, K., et al., *Self-assembled ternary complexes stabilized with hyaluronic acid-green tea catechin conjugates for targeted gene delivery*. J Control Release, 2016. 226: p. 205-16.

75. Mitter, N., et al., *Clay nanosheets for topical delivery of RNAi for sustained protection against plant viruses*. Nat Plants, 2017. 3: p. 16207.

76. Sajeesh, S., et al., *Long dsRNA-mediated RNA interference and immunostimulation: a targeted delivery approach using polyethyleneimine based nano-carriers*. Mol Pharm, 2014. 11(3): p. 872-84.

77. Dhandapani, R. K., et al., *Development of CS-TPP-dsRNA nanoparticles to enhance RNAi efficiency in the yellow fever mosquito, Aedes aegypti*. Sci Rep, 2019. 9(1): p. 8775.

78. Dahlman, J. E., et al., *In vivo endothelial siRNA delivery using polymeric nanoparticles with low molecular weight*. Nat Nanotechnol, 2014. 9(8): p. 648-655.

79. Zhao, Y., et al., *PolyMetformin combines carrier and anticancer activities for in vivo siRNA delivery*. Nat Commun, 2016. 7: p. 11822.

80. Cui, J., et al., *Ex vivo pretreatment of human vessels with siRNA nanoparticles provides protein silencing in endothelial cells*. Nat Commun, 2017. 8(1): p. 191.

81. Kwon, Y. J., *Before and after endosomal escape: roles of stimuli-converting siRNA/polymer interactions in determining gene silencing efficiency*. Acc Chem Res, 2012. 45(7): p. 1077-88.

82. Gao, Y., et al., *Highly Branched Poly(beta-amino esters) for Non-Viral Gene Delivery: High Transfection Efficiency and Low Toxicity Achieved by Increasing Molecular Weight*. Biomacromolecules, 2016. 17(11): p. 3640-3647.

83. Liu, X., et al., *Structurally flexible triethanolamine-core poly(amidoamine) dendrimers as effective nanovectors to deliver RNAi-based therapeutics*. Biotechnol Adv, 2014. 32(4): p. 844-52.

84. Yang, X. Z., et al., *Sheddable ternary nanoparticles for tumor acidity-targeted siRNA delivery*. ACS Nano, 2012. 6(1): p. 771-81.

85. Kulkarni, A., et al., *Pendant polymer:amino-beta-cyclodextrin:siRNA guest: host nanoparticles as efficient vectors for gene silencing*. J Am Chem Soc, 2012. 134(18): p. 7596-9.

86. Ali, E. E., et al., *Protein Binding Characteristics of the Principal Green Tea Catechins: A QCM Study Comparing Crude Extract to Pure EGCG*. Biochem Res Int, 2019. 2019: p. 6154170.

87. Shen, W., et al., *Green Tea Catechin Dramatically Promotes RNAi Mediated by Low-Molecular-Weight Polymers*. ACS Cent Sci, 2018. 4(10): p. 1326-1333.

88. Ding, J., et al., *"Stealth and Fully-Laden" Drug Carriers: Self-Assembled Nanogels Encapsulated with Epigallocatechin Gallate and siRNA for Drug-Resistant Breast Cancer Therapy*. ACS Appl Mater Interfaces, 2018. 10(12): p. 9938-9948.

What is claimed is:

1. A polyplex composition, comprising:
    a cation selected from the group consisting of celfectin (Cf) and epigallocatechin gallate (EGCG);
    a crosslinker selected from the group consisting of polyethylenimine (PEI), protamine sulfate (PS), poly(lactide-co-glycolide) (PLGA), and poly-L-lysine (PLL); and
    a double stranded RNA (dsRNA) molecule for initiating RNA interference (RNAi) in a mosquito;
    wherein the ratio of cation to crosslinker is from about 1:0.1 to about 1:100.

2. The composition of claim 1, wherein the dsRNA is provided in a viral vector.

3. The composition of claim 1, wherein the dsRNA encodes a polypeptide, or a fragment thereof, selected from the group consisting of inhibitor of apoptosis (IAP), vacuolar-sorting protein SNF7 (SNF7), snakeskin (SSK), steroid receptor co-activator (SRC), and combinations thereof.

4. The composition of claim 1, wherein the cation is EGCG and the crosslinker is PLL.

5. The composition of claim 4, wherein the ratio of cation to crosslinker is from about 1:1 to about 1:10.

6. The composition of claim 1, wherein the cation is PLGA and the crosslinker is PEI.

7. The composition of claim 6, wherein the ratio of cation to crosslinker is from about 1:0.1 to about 1:10.

8. A method of inducing RNAi in a mosquito, comprising: administering to an insect the composition of claim 1.

9. The method of claim 8, wherein the composition is administered at a dose of about 25 ng to about 2 μg.

10. The method of claim 8, wherein the composition is administered to the insect for about 1 to about 24 hours.

11. The method of claim 8, wherein the composition is administered orally.

12. The method of claim 11, wherein the composition is provided in a sucrose solution.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: IAP1 Forward Primer

<400> SEQUENCE: 1
cttctgccga gtggaaatcg g                                         21

<210> SEQ ID NO 2
<211> LENGTH: 21
<212> TYPE: DNA
<213> ORGANISM: Artificial Sequence
<220> FEATURE:
<223> OTHER INFORMATION: IAP1 Reverse Primer

<400> SEQUENCE: 2
atattccggt agcttctgtt g                                         21

<210> SEQ ID NO 3
<211> LENGTH: 21
<212> TYPE: DNA
<213> ORGANISM: Artificial Sequence
<220> FEATURE:
<223> OTHER INFORMATION: IAP1 qPCR Forward Primer

<400> SEQUENCE: 3
gtgtttggcc aagaaggaaa g                                         21

<210> SEQ ID NO 4
<211> LENGTH: 20
<212> TYPE: DNA
<213> ORGANISM: Artificial Sequence
<220> FEATURE:
<223> OTHER INFORMATION: IAP1 qPCR Reverse Primer

<400> SEQUENCE: 4
tgactgaagc gaggatgttg                                           20

<210> SEQ ID NO 5
<211> LENGTH: 20
<212> TYPE: DNA
<213> ORGANISM: Artificial Sequence
<220> FEATURE:
<223> OTHER INFORMATION: SNF7 Forward Primer

<400> SEQUENCE: 5
acgatgtcca cgagatgatg                                           20

<210> SEQ ID NO 6
<211> LENGTH: 17
<212> TYPE: DNA
<213> ORGANISM: Artificial Sequence
<220> FEATURE:
<223> OTHER INFORMATION: SNF7 Reverse Primer

<400> SEQUENCE: 6
caggcagatc ggttgct                                              17

<210> SEQ ID NO 7
<211> LENGTH: 24
<212> TYPE: DNA
<213> ORGANISM: Artificial Sequence

```
<220> FEATURE:
<223> OTHER INFORMATION: SRC Forward Primer

<400> SEQUENCE: 7
cgtcaaatgc agcagatcac ccaa                                              24

<210> SEQ ID NO 8
<211> LENGTH: 24
<212> TYPE: DNA
<213> ORGANISM: Artificial Sequence
<220> FEATURE:
<223> OTHER INFORMATION: SRC Reverse Primer

<400> SEQUENCE: 8
tgttggttgt tcgagggaga aggt                                              24

<210> SEQ ID NO 9
<211> LENGTH: 19
<212> TYPE: DNA
<213> ORGANISM: Artificial Sequence
<220> FEATURE:
<223> OTHER INFORMATION: S7RP qPCR Forward Primer

<400> SEQUENCE: 9
accgccgtct acgatgcca                                                    19

<210> SEQ ID NO 10
<211> LENGTH: 20
<212> TYPE: DNA
<213> ORGANISM: Artificial Sequence
<220> FEATURE:
<223> OTHER INFORMATION: S7RP qPCR Reverse Primer

<400> SEQUENCE: 10
atggtggtct gctggttctt                                                   20
```